United States Patent
Pahan

(10) Patent No.: US 11,524,052 B2
(45) Date of Patent: Dec. 13, 2022

(54) COMPOSITIONS AND METHODS FOR TREATING NEUROLOGICAL AND OTHER DISORDERS

(71) Applicant: Rush University Medical Center, Chicago, IL (US)

(72) Inventor: Kalipada Pahan, Skokie, IL (US)

(73) Assignee: Rush University Medical Center, Chicago, IL (US)

( * ) Notice: Subject to any disclaimer, the term of this patent is extended or adjusted under 35 U.S.C. 154(b) by 0 days.

(21) Appl. No.: 16/966,277

(22) PCT Filed: Dec. 28, 2018

(86) PCT No.: PCT/US2018/067876
§ 371 (c)(1),
(2) Date: Jul. 30, 2020

(87) PCT Pub. No.: WO2019/135992
PCT Pub. Date: Jul. 11, 2019

(65) Prior Publication Data
US 2021/0361740 A1  Nov. 25, 2021

Related U.S. Application Data

(60) Provisional application No. 62/612,906, filed on Jan. 2, 2018.

(51) Int. Cl.
*A61K 38/08* (2019.01)
*A61K 38/16* (2006.01)
*A61K 47/64* (2017.01)
*A61K 9/00* (2006.01)
*A61P 25/16* (2006.01)
*A61P 25/28* (2006.01)
*A61P 29/00* (2006.01)
*A61K 38/17* (2006.01)

(52) U.S. Cl.
CPC .......... *A61K 38/177* (2013.01); *A61K 9/0043* (2013.01); *A61K 47/64* (2017.08); *A61P 25/16* (2018.01); *A61P 25/28* (2018.01)

(58) Field of Classification Search
CPC ...... A61K 38/08; A61K 38/16; A61K 38/177; A61K 47/64; A61K 9/0043; A61K 9/00; A61K 38/17; A61P 25/16; A61P 25/28; A61P 29/00; C07K 14/705
See application file for complete search history.

(56) References Cited

U.S. PATENT DOCUMENTS

| | | | |
|---|---|---|---|
| 7,033,830 B2 * | 4/2006 | Karras | C12N 15/113 435/375 |
| 2004/0038926 A1 * | 2/2004 | Karras | C12N 15/113 514/44 R |
| 2005/0181476 A1 | 8/2005 | Beyaert et al. | |
| 2010/0069297 A1 | 3/2010 | Fenton et al. | |

FOREIGN PATENT DOCUMENTS

| | | |
|---|---|---|
| EP | 3647321 A1 | 5/2020 |
| WO | 2009/000929 A2 | 12/2008 |

OTHER PUBLICATIONS

European Patent Office, Extended European Search Report issued in corresponding European application No. 18898010.6, dated Jul. 22, 2021, 10 pp.

McDonald, Claire L., et al., "Inhibiting TLR2 Activation Attenuates Amyloid Accumulation and glial activation in a mouse model of Alzheimer's disease", Brain, Behavior and Immunity, Nov. 1, 2016, vol. 58, pp. 191-200, XP055817820, US ISSN: 0889-1591, DOI: 10.1016/j.bbi.2016.07.143 (10 pp).

* cited by examiner

*Primary Examiner* — Julie Ha
(74) *Attorney, Agent, or Firm* — Taft Stettinius & Hollister LLP; Joseph Bennett-Paris

(57) ABSTRACT

Methods for treating neurological and other disorders, including autoimmune disorders are described. Also described is a method of treating a disorder in which Toll-like Receptor 2 (TLR2) activation by binding to myeloid differentiation primary response 88 (MyD88) plays a role in disease pathogenesis. Further a method is described that includes the administration of a composition, including a peptide sequence, that inhibits the activation of TLR2 by MyD88.

7 Claims, 39 Drawing Sheets

Specification includes a Sequence Listing.

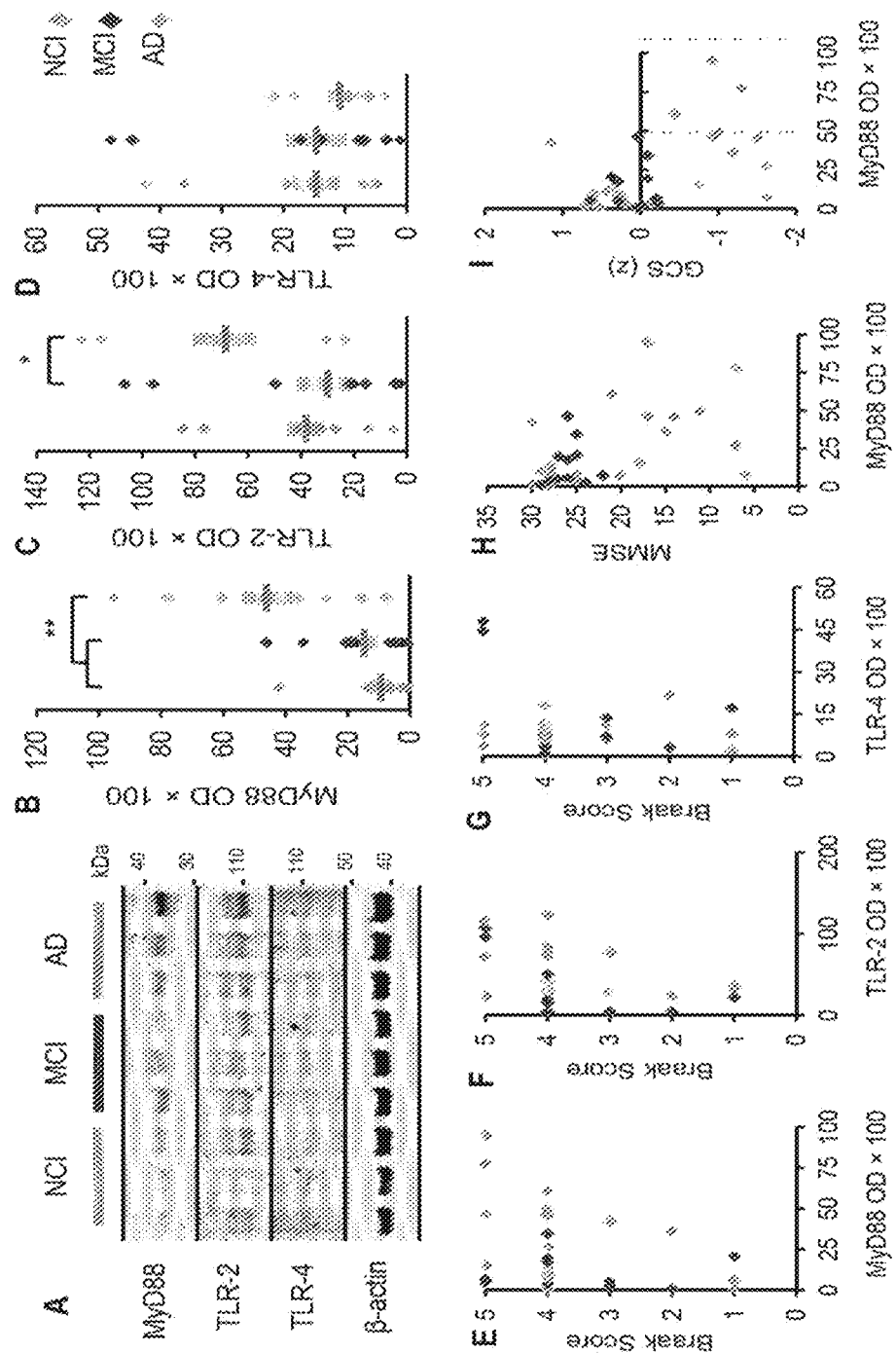
Figure 1(A-I)

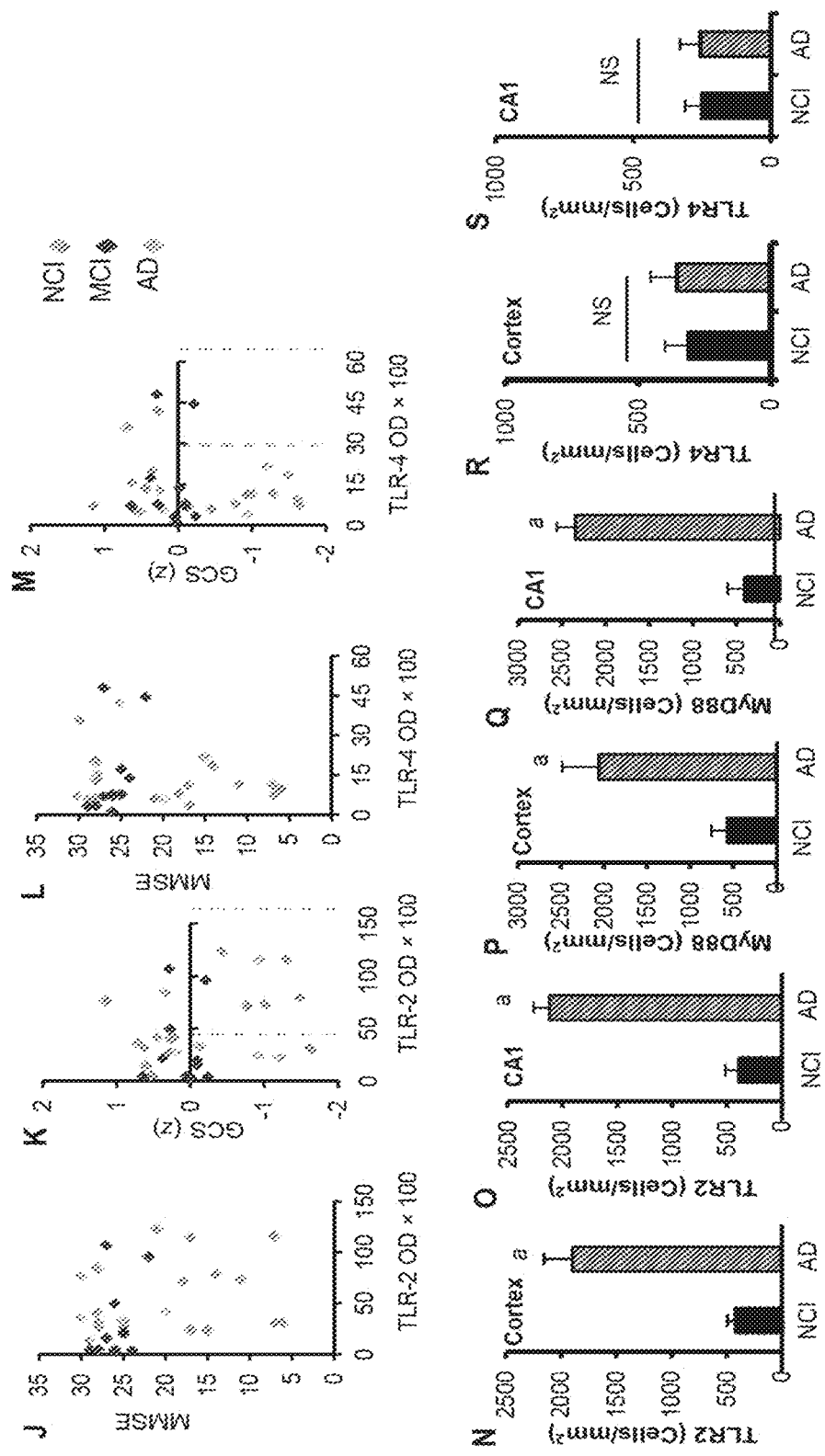
Figure 1(J-S)

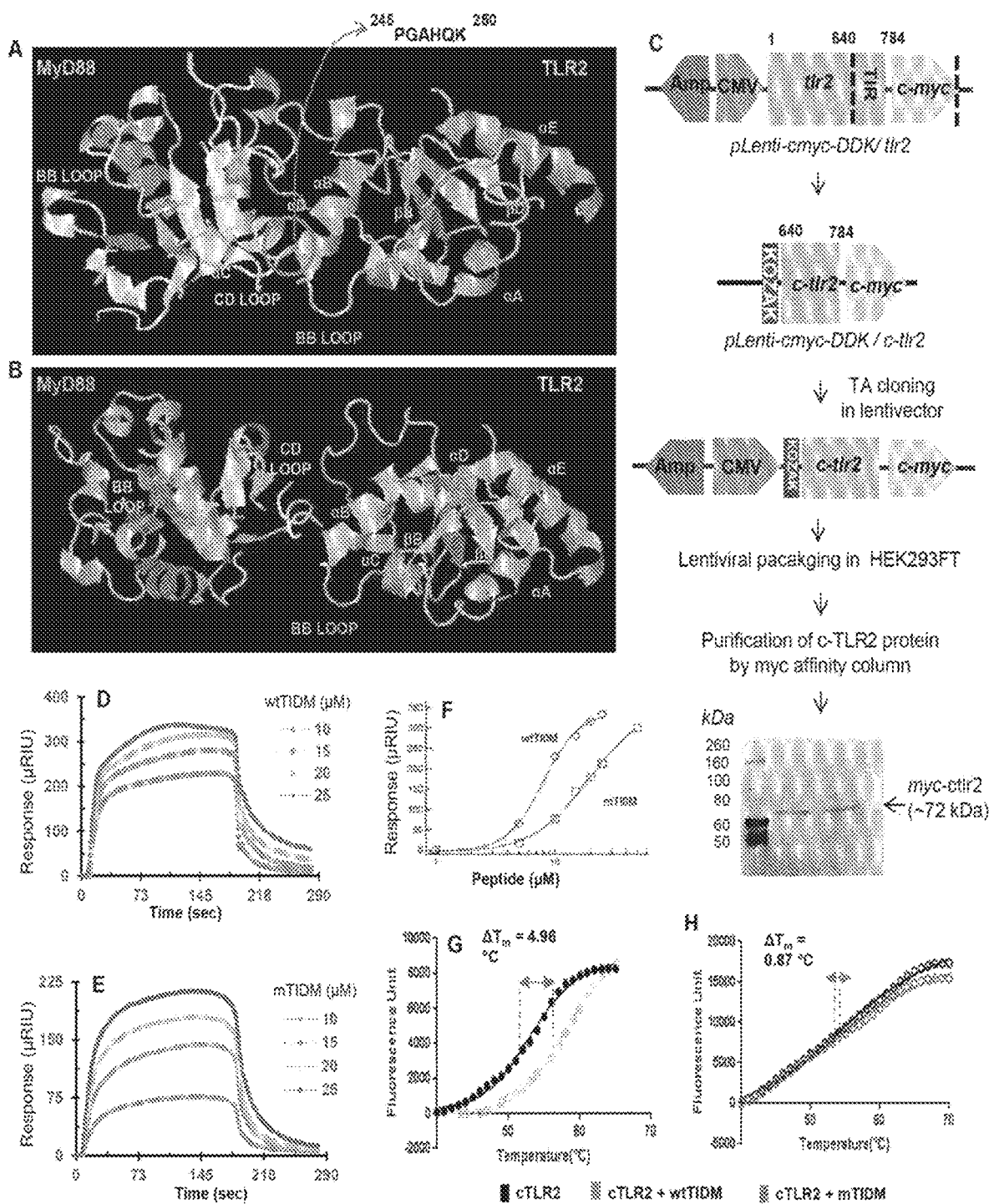
Figure 2 (A-H)

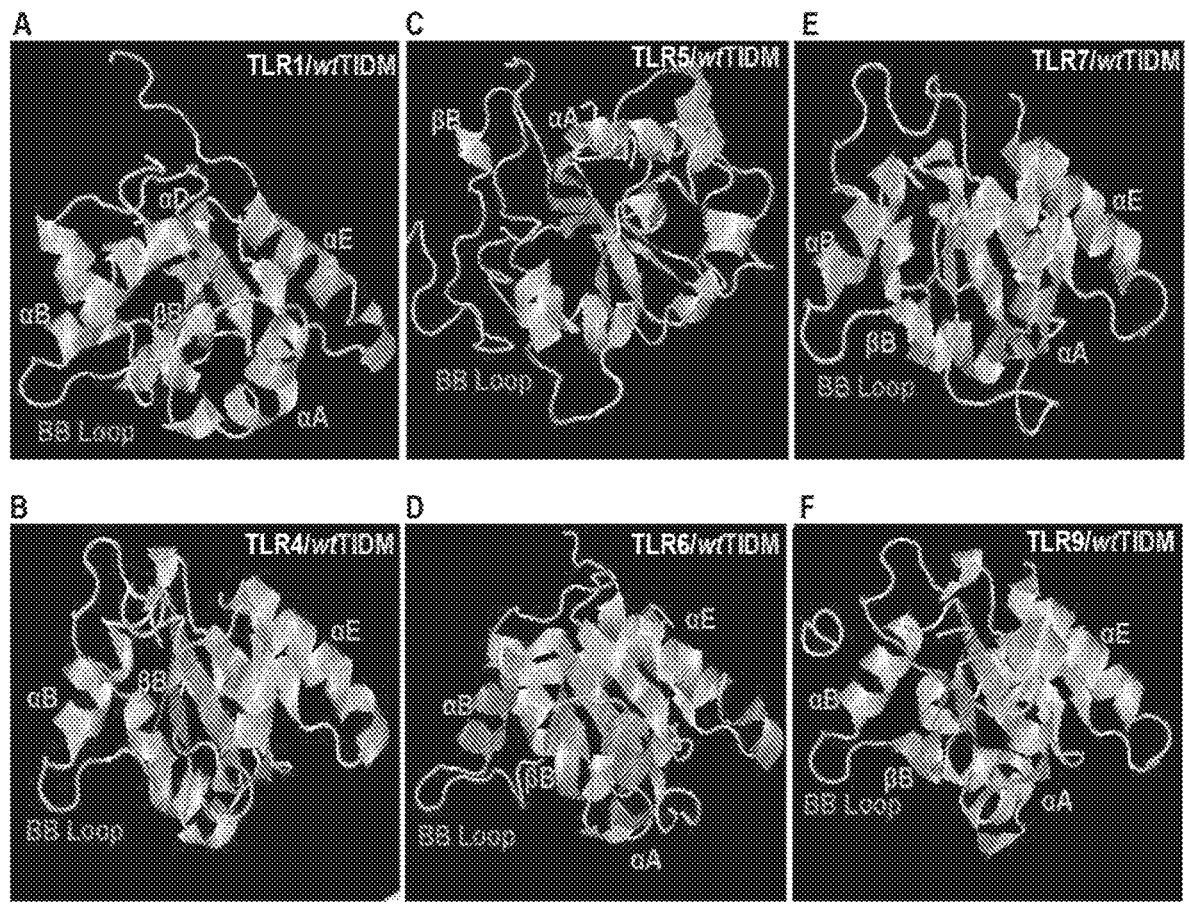
Figure 3(A-F)

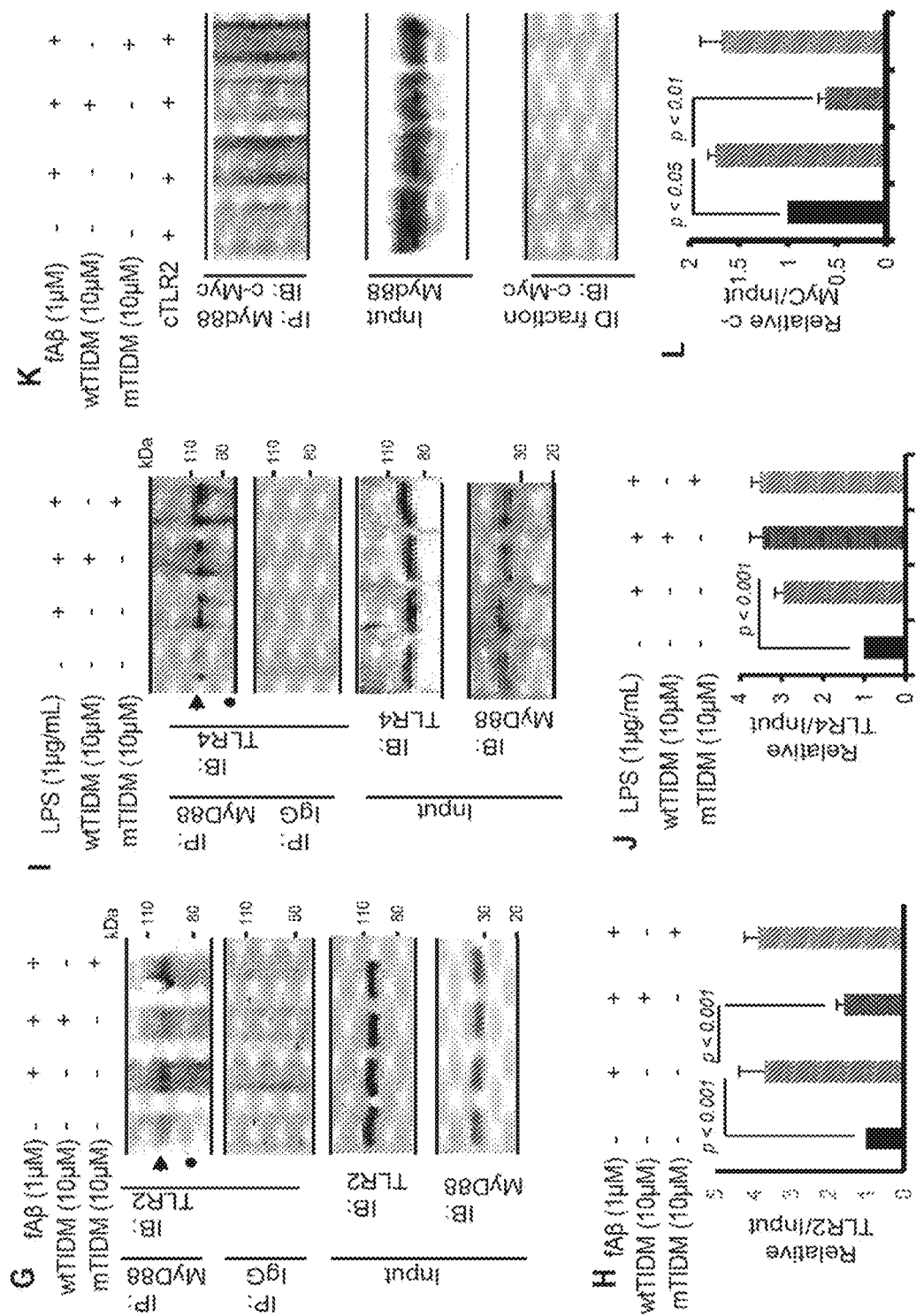
Figure 3(G-L)

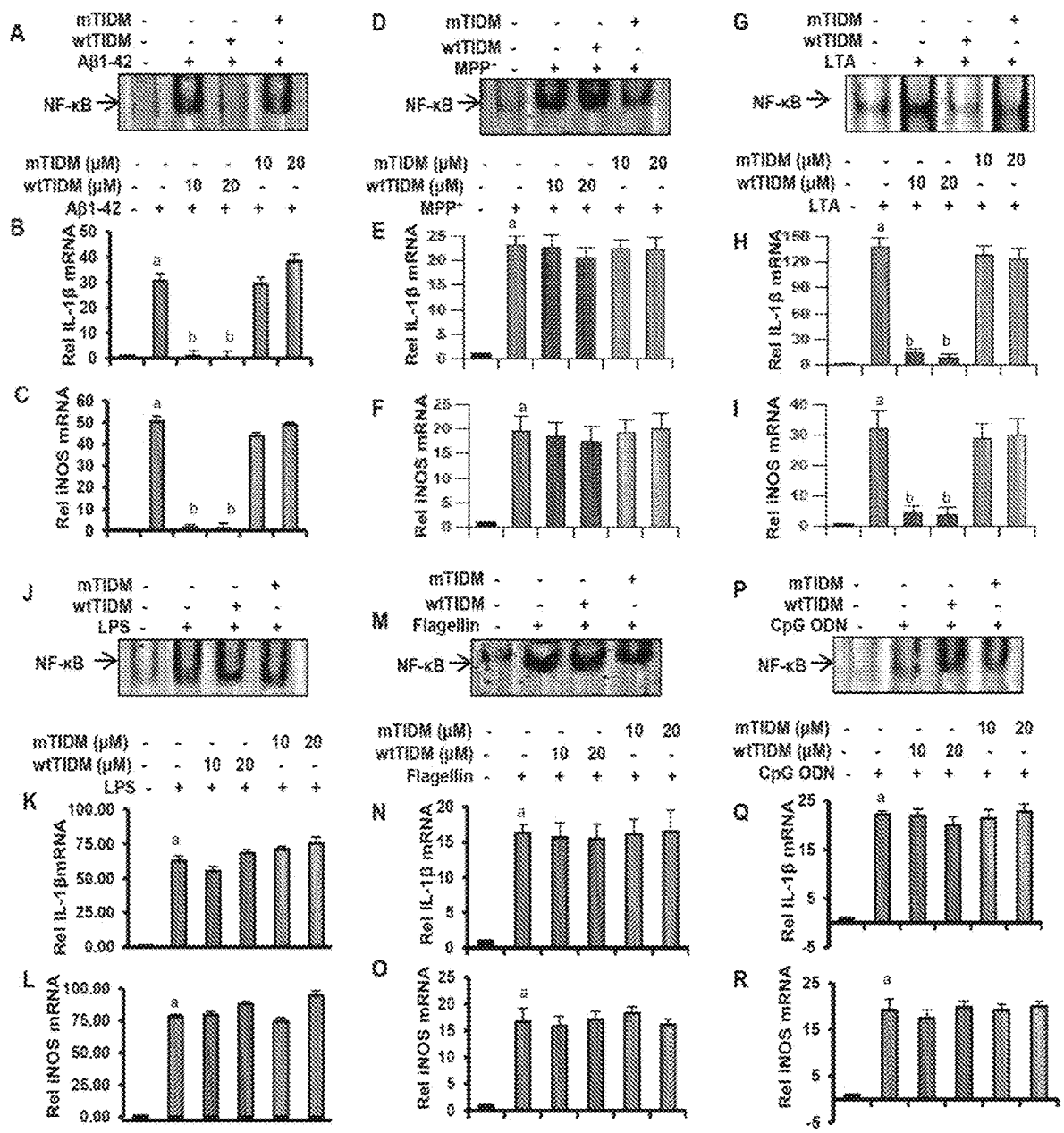
Figure 4(A-R)

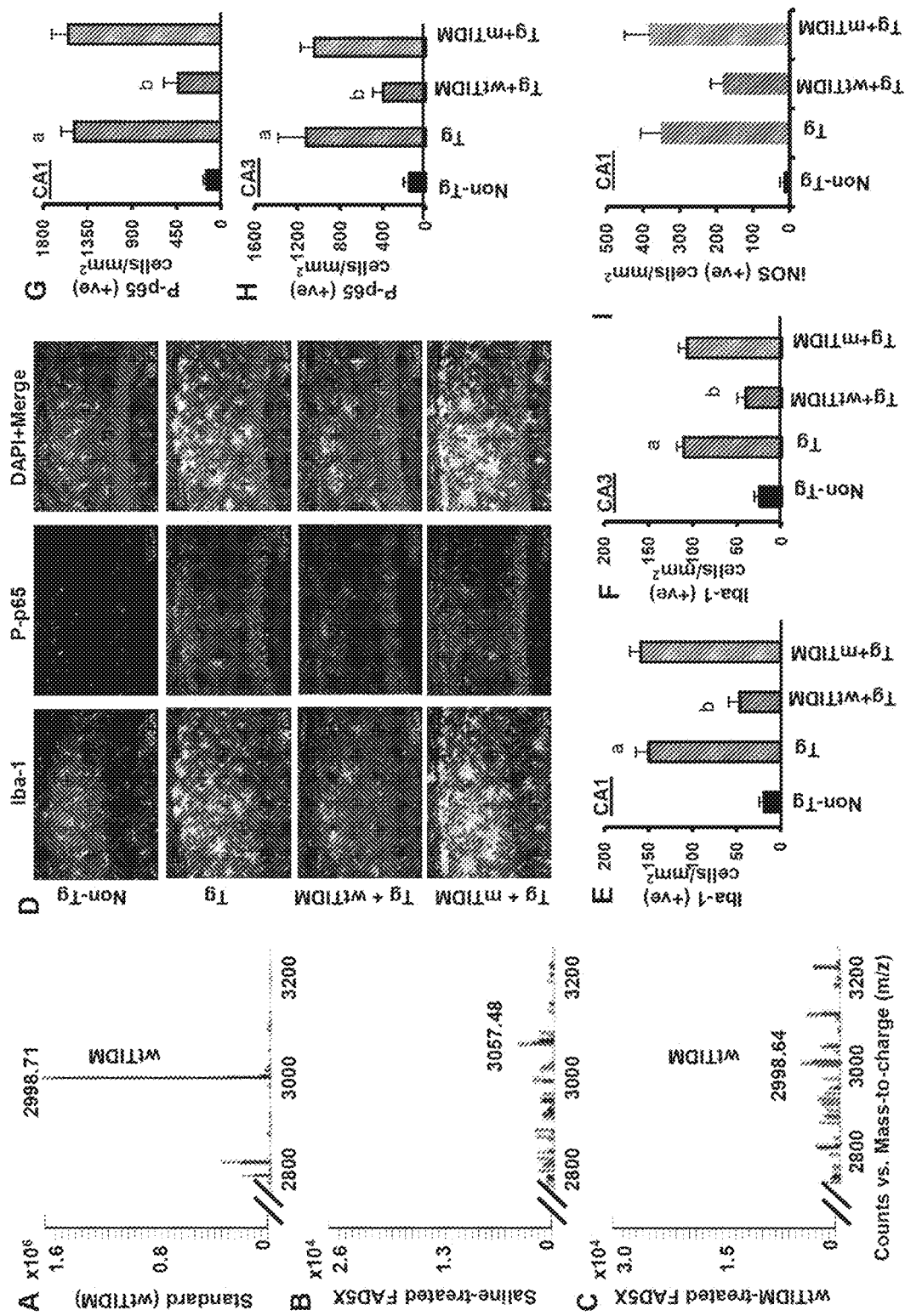
Figure 5(A-I)

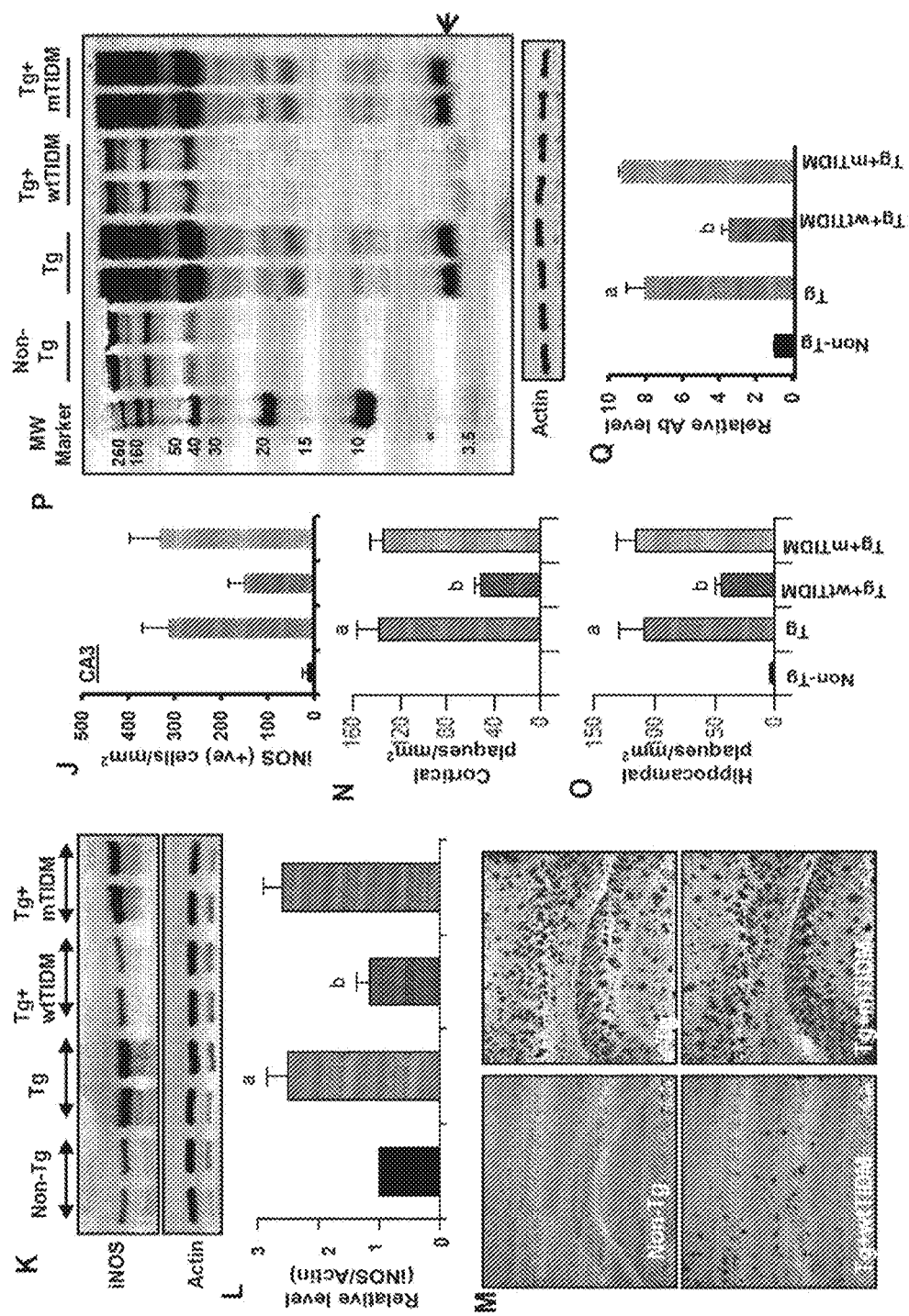
Figure 5(J-Q)

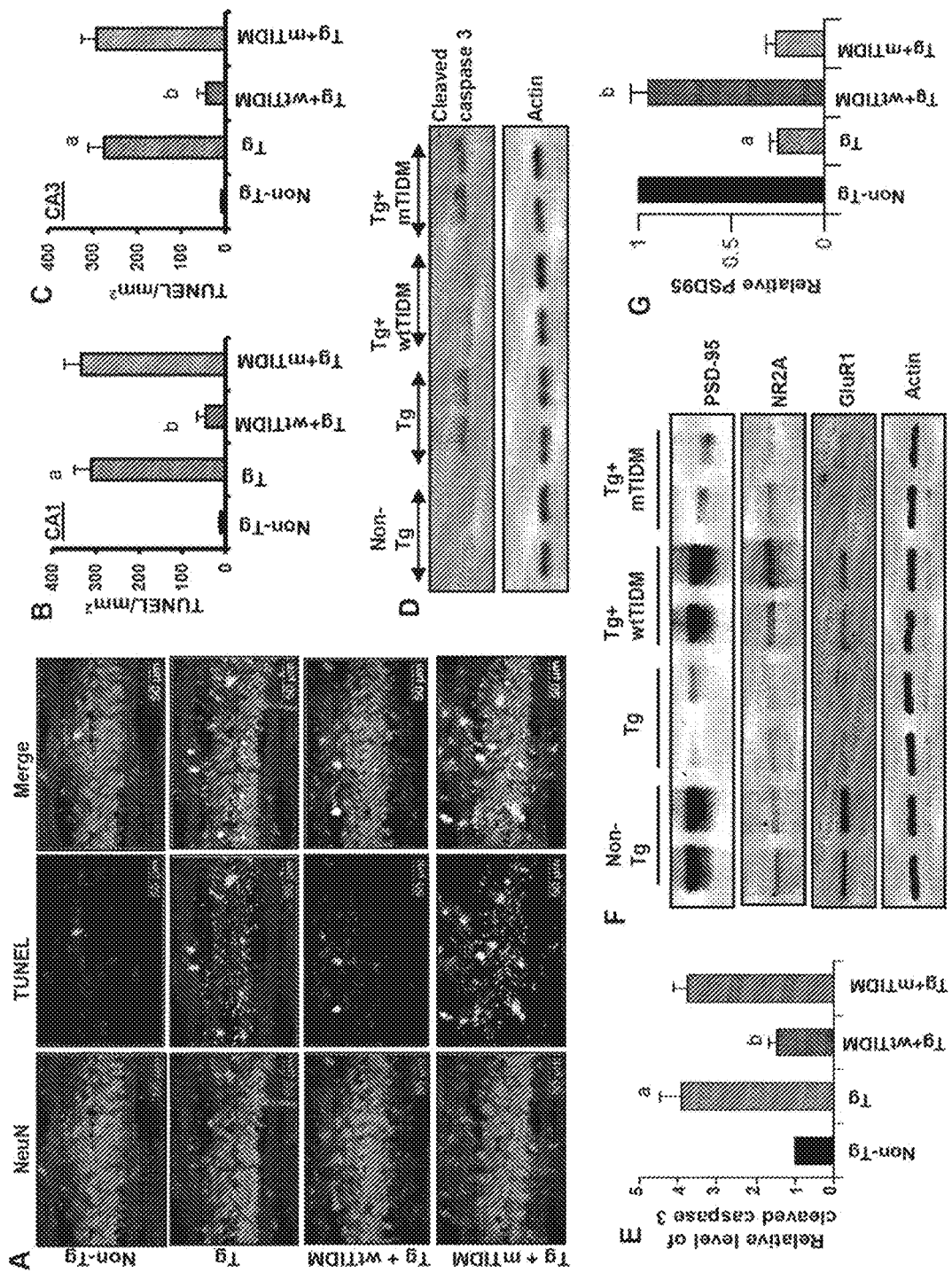
Figure 6(A-G)

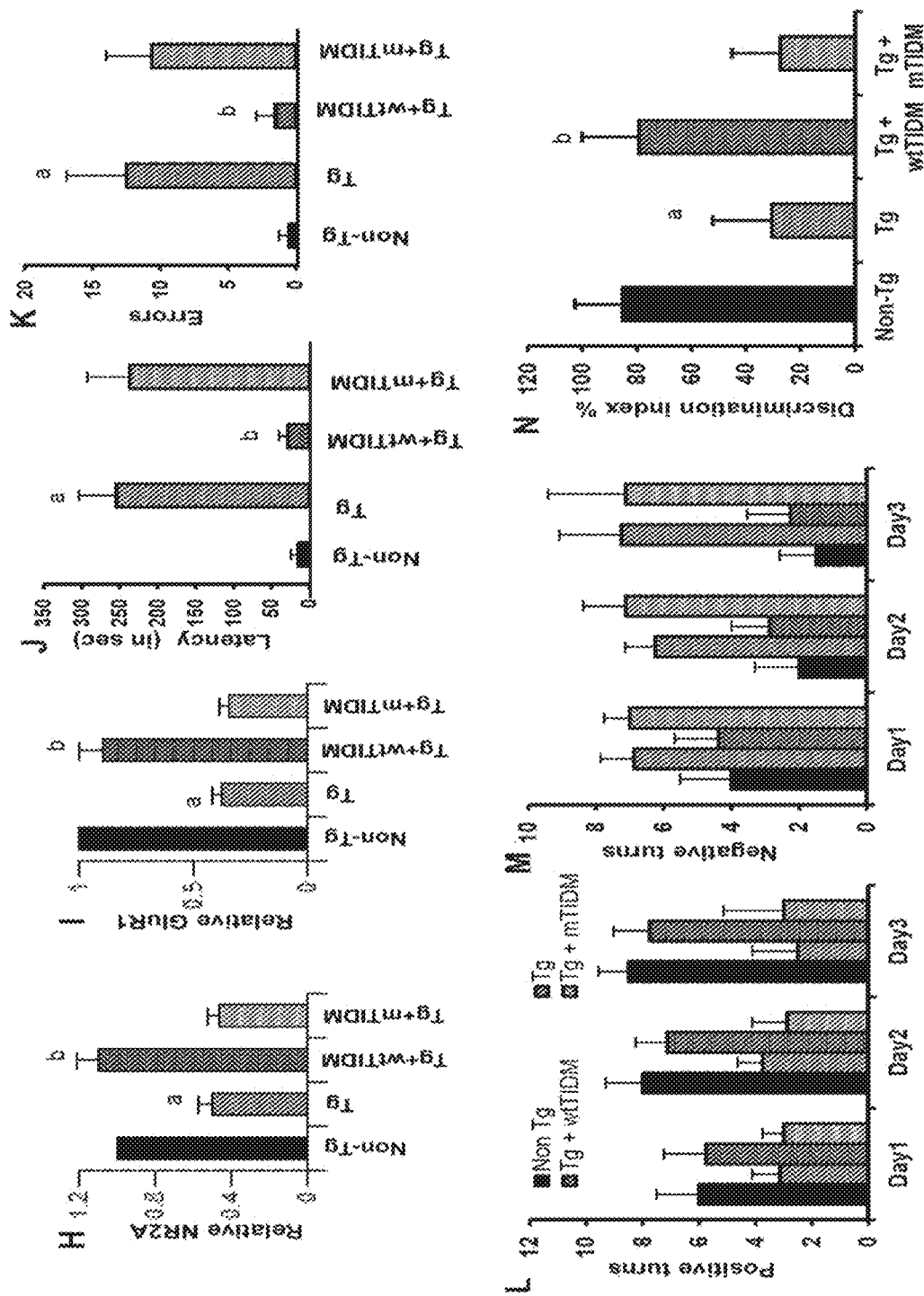
Figure 6(H-N)

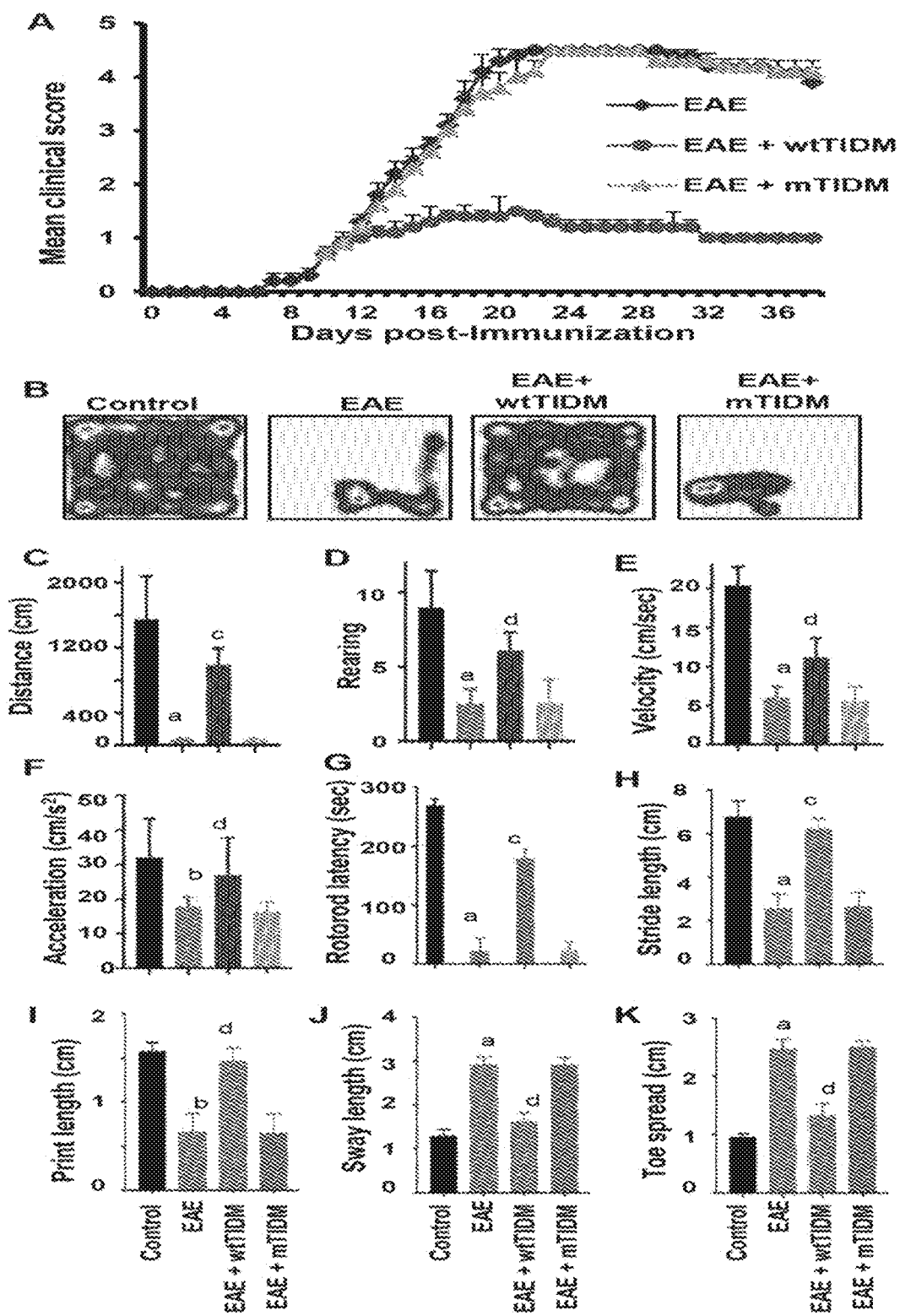
Figure 7(A-K)

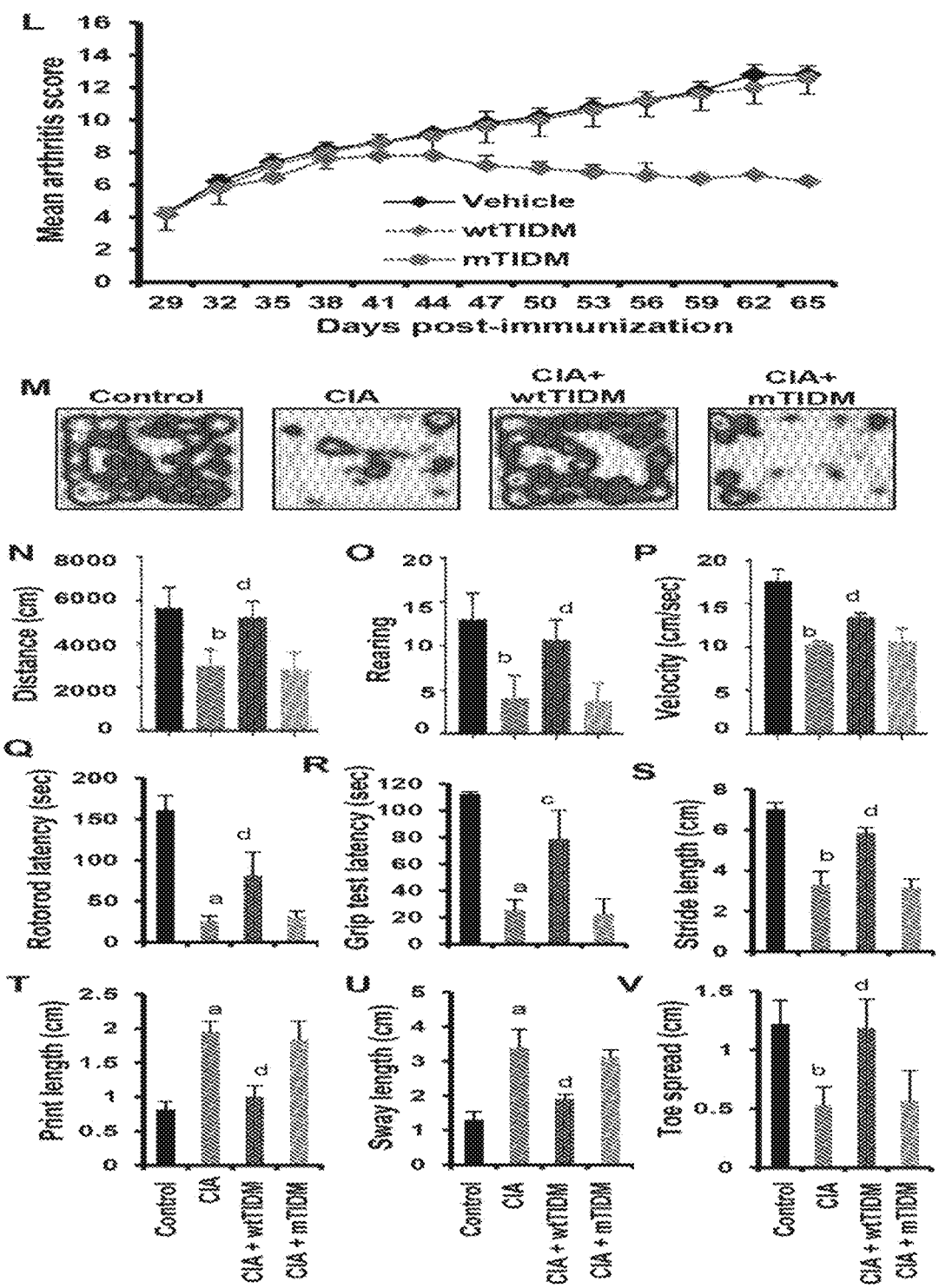
Figure 7(L-V)

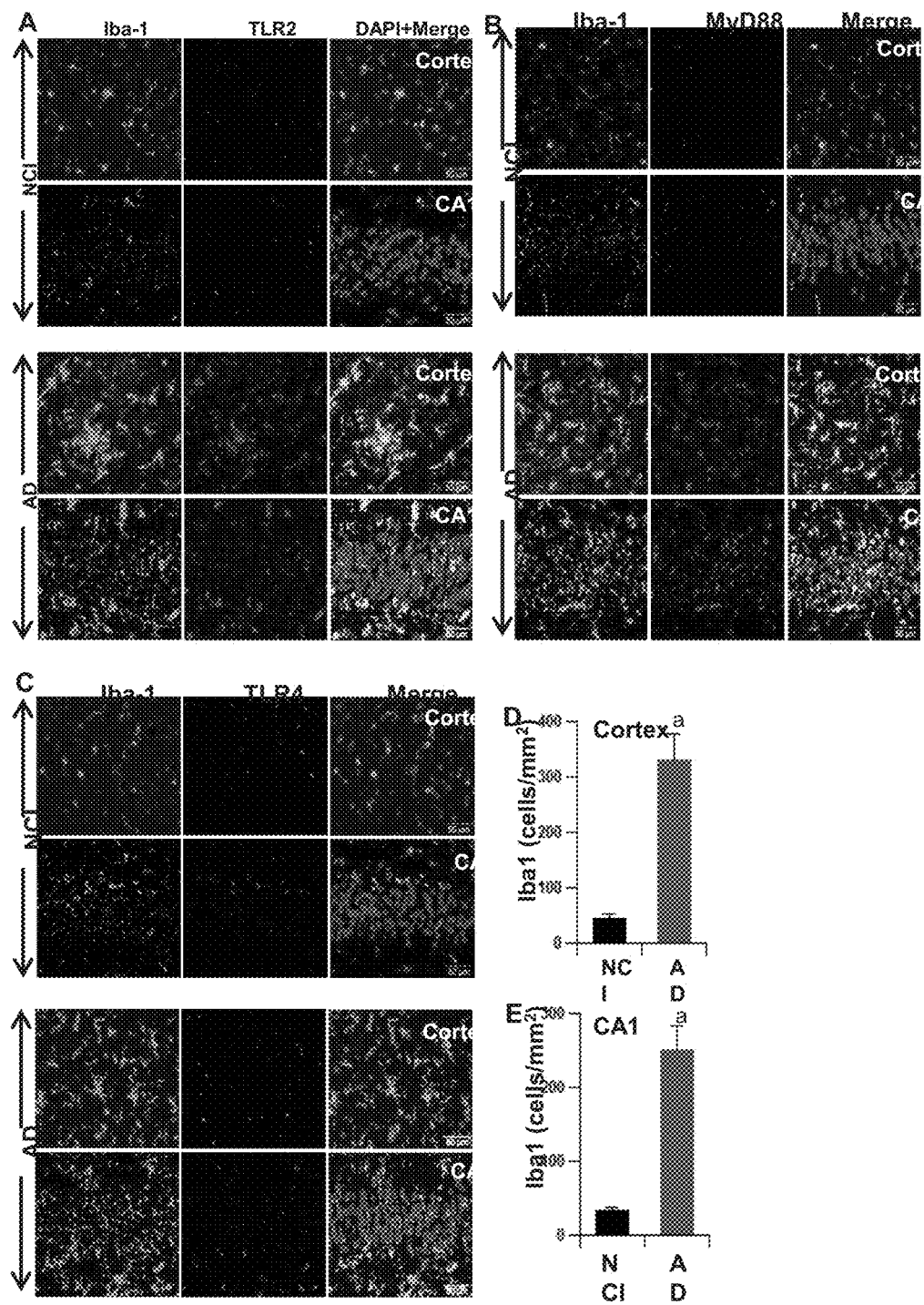
Figure 8 (A-D)

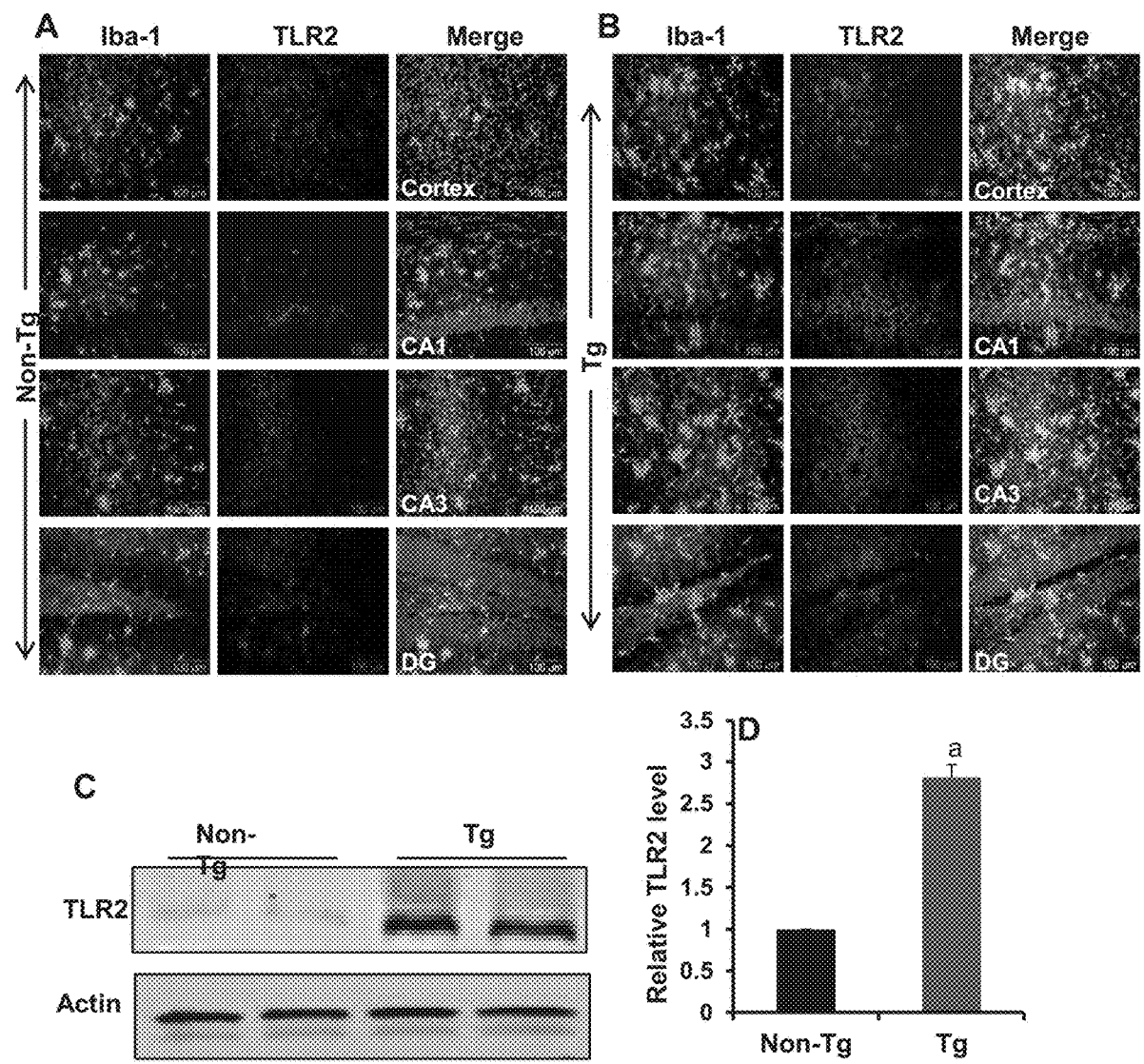
Figure 9 (A-D)

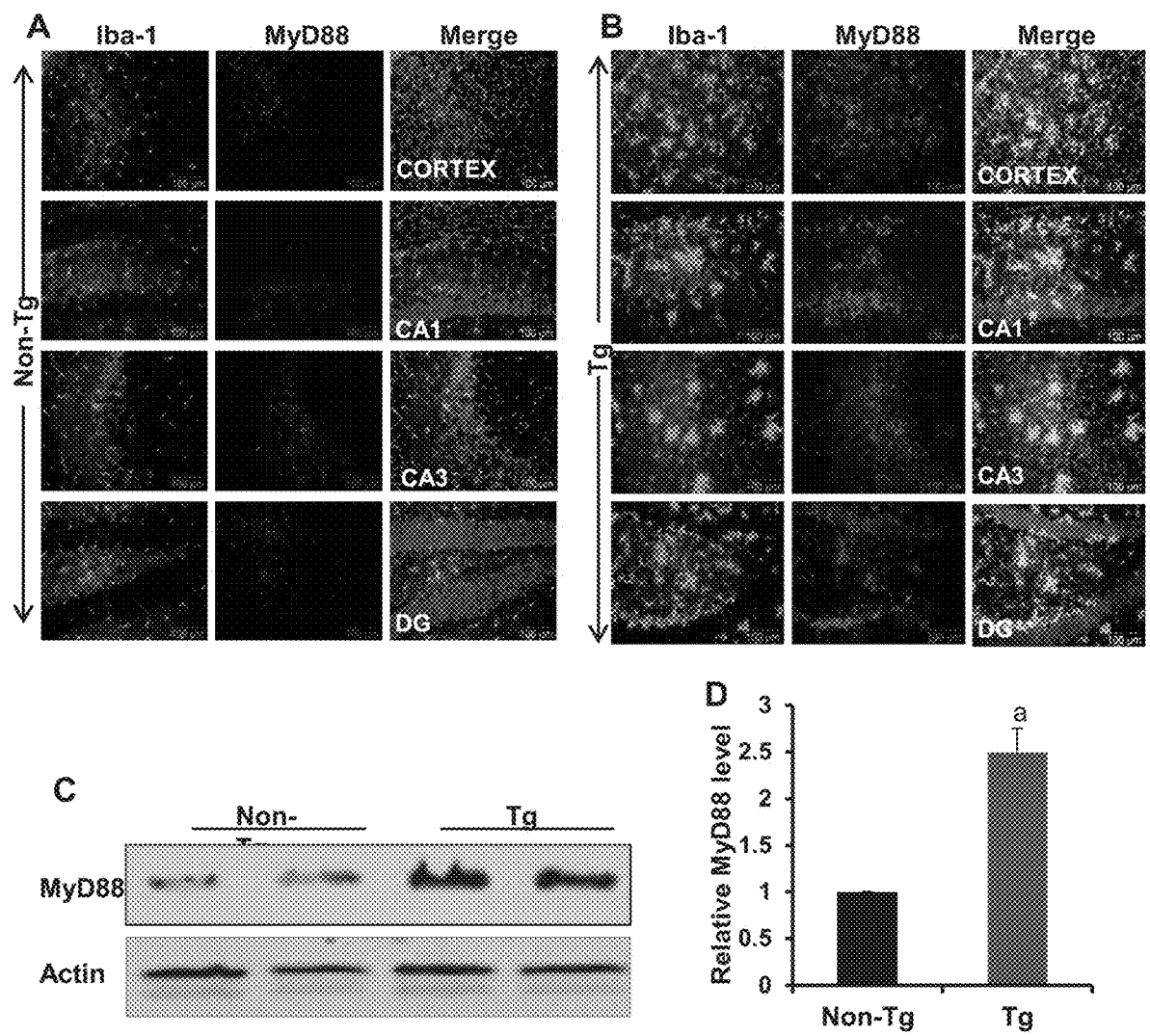
Figure 10 (A-D)

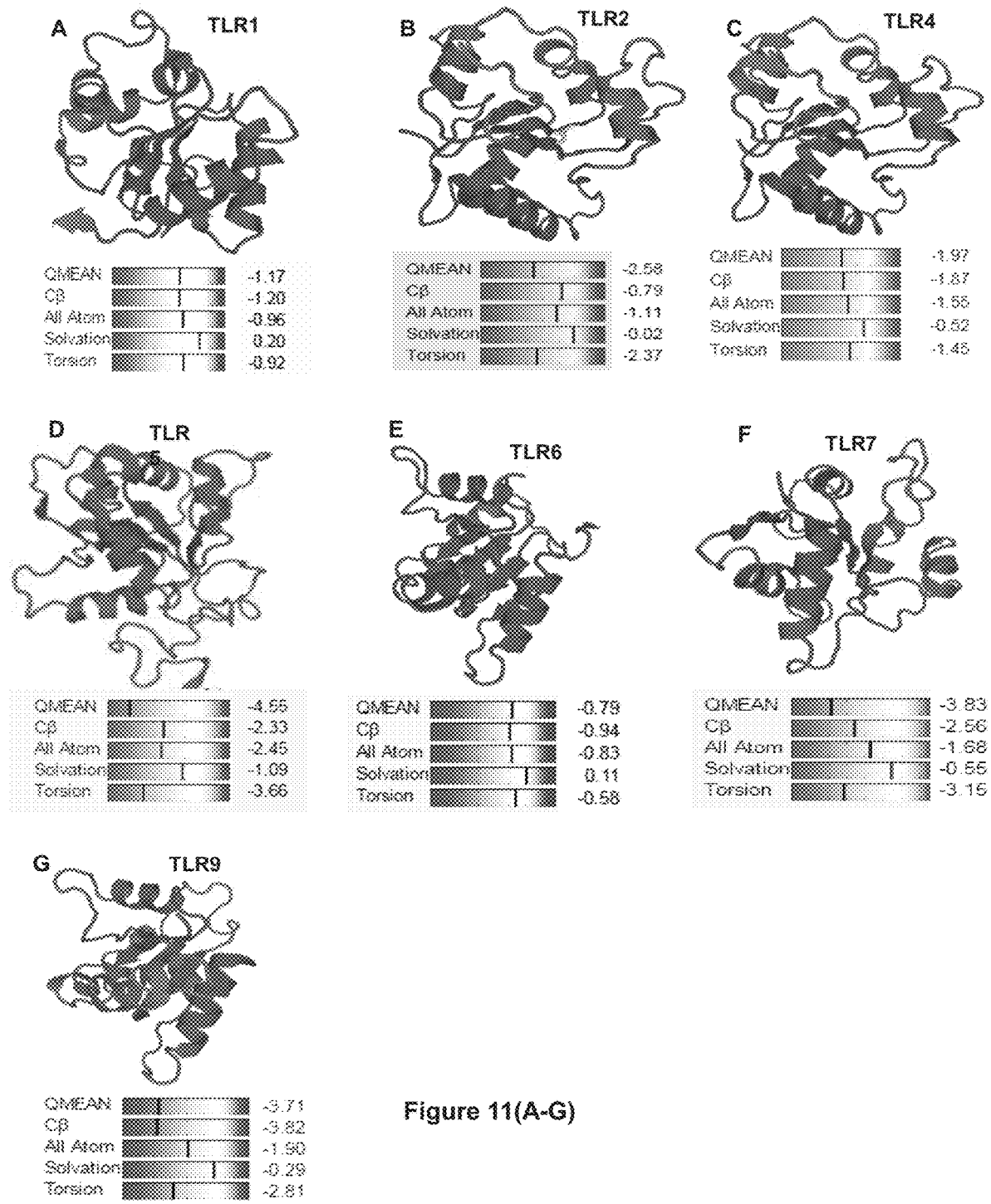
Figure 11(A-G)

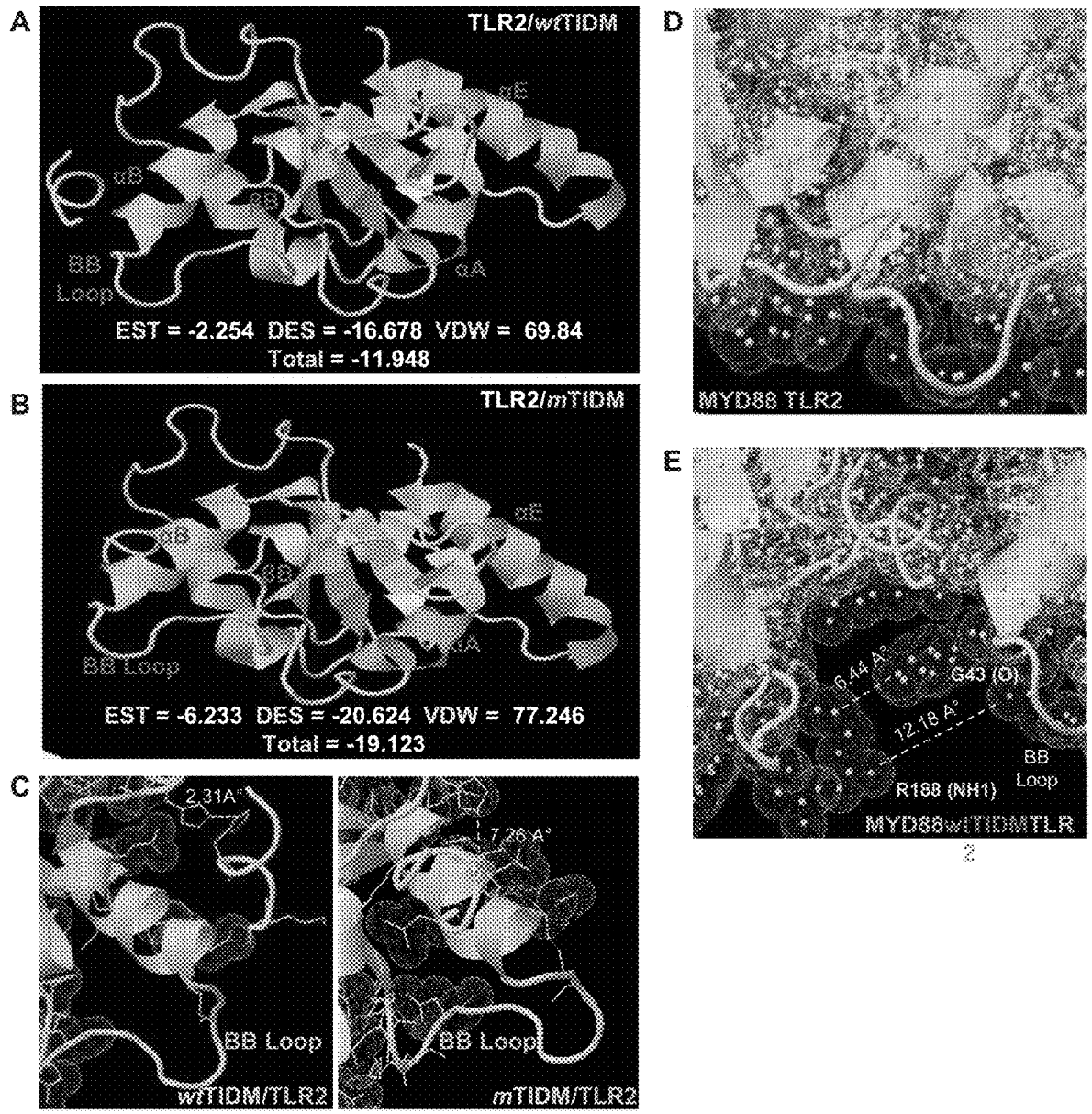
Figure 12 (A-E)

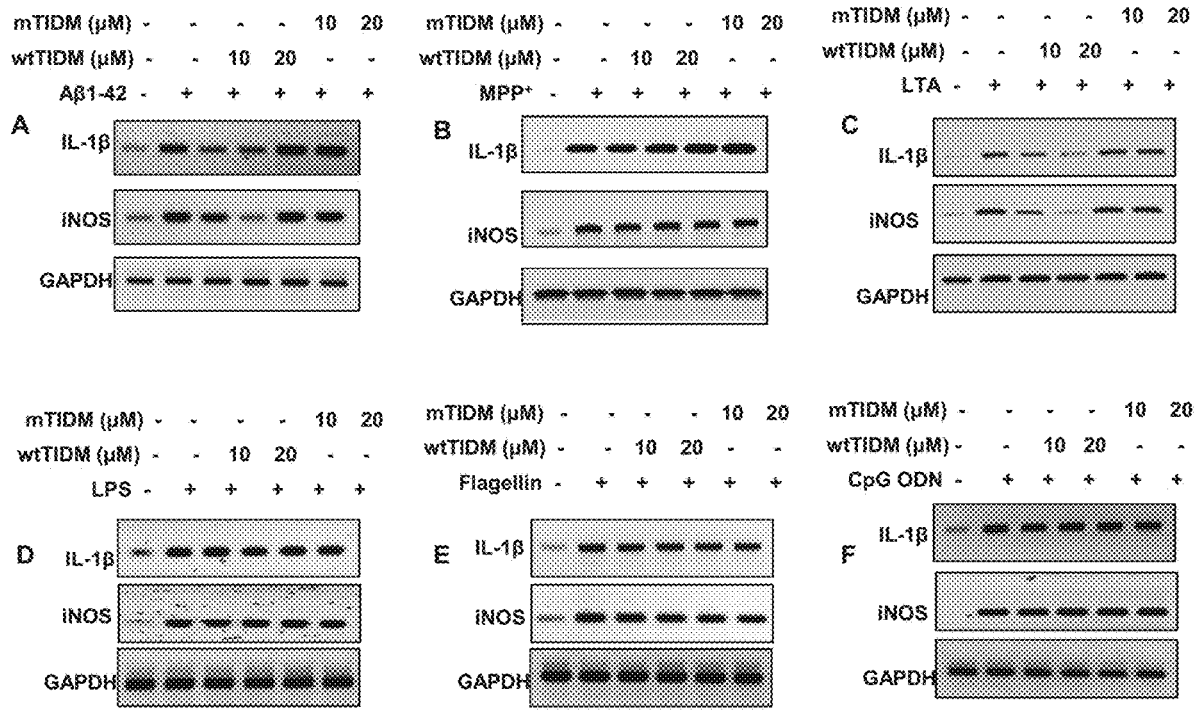
Figure 13(A-F)

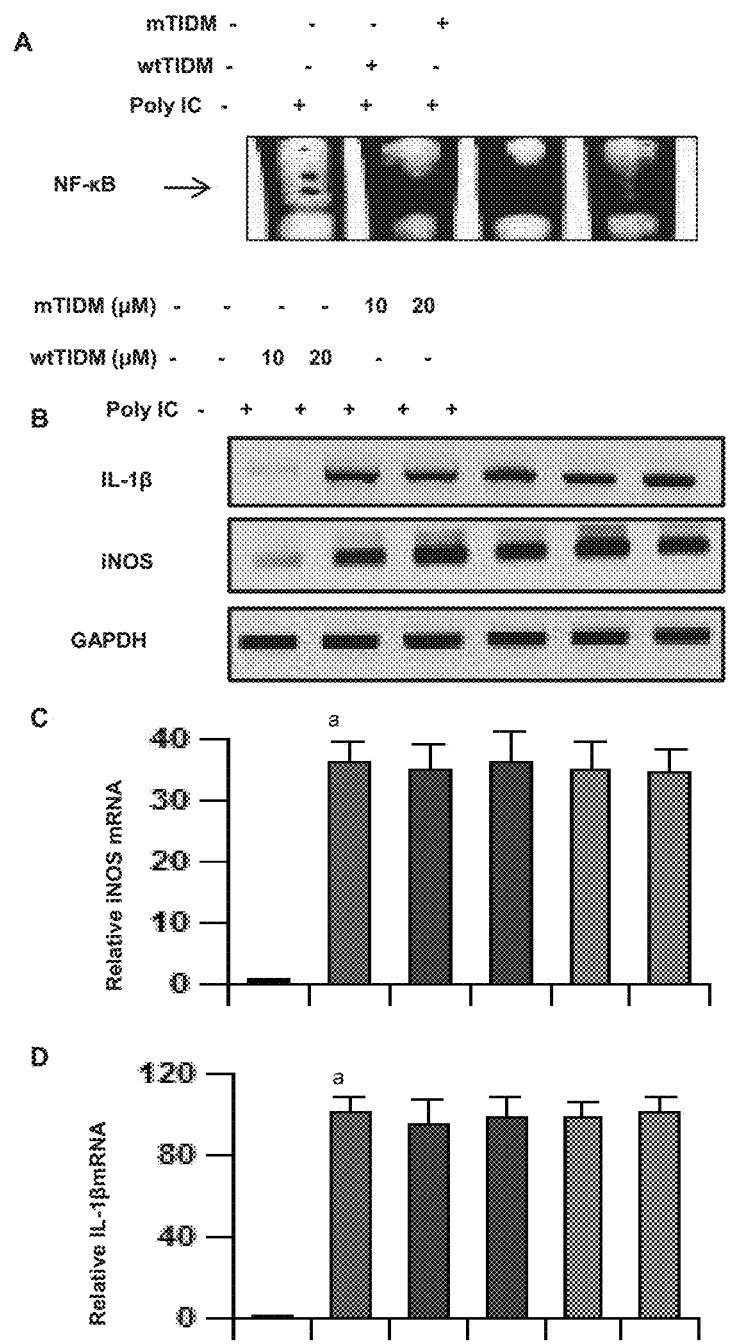
Figure 14(A-D)

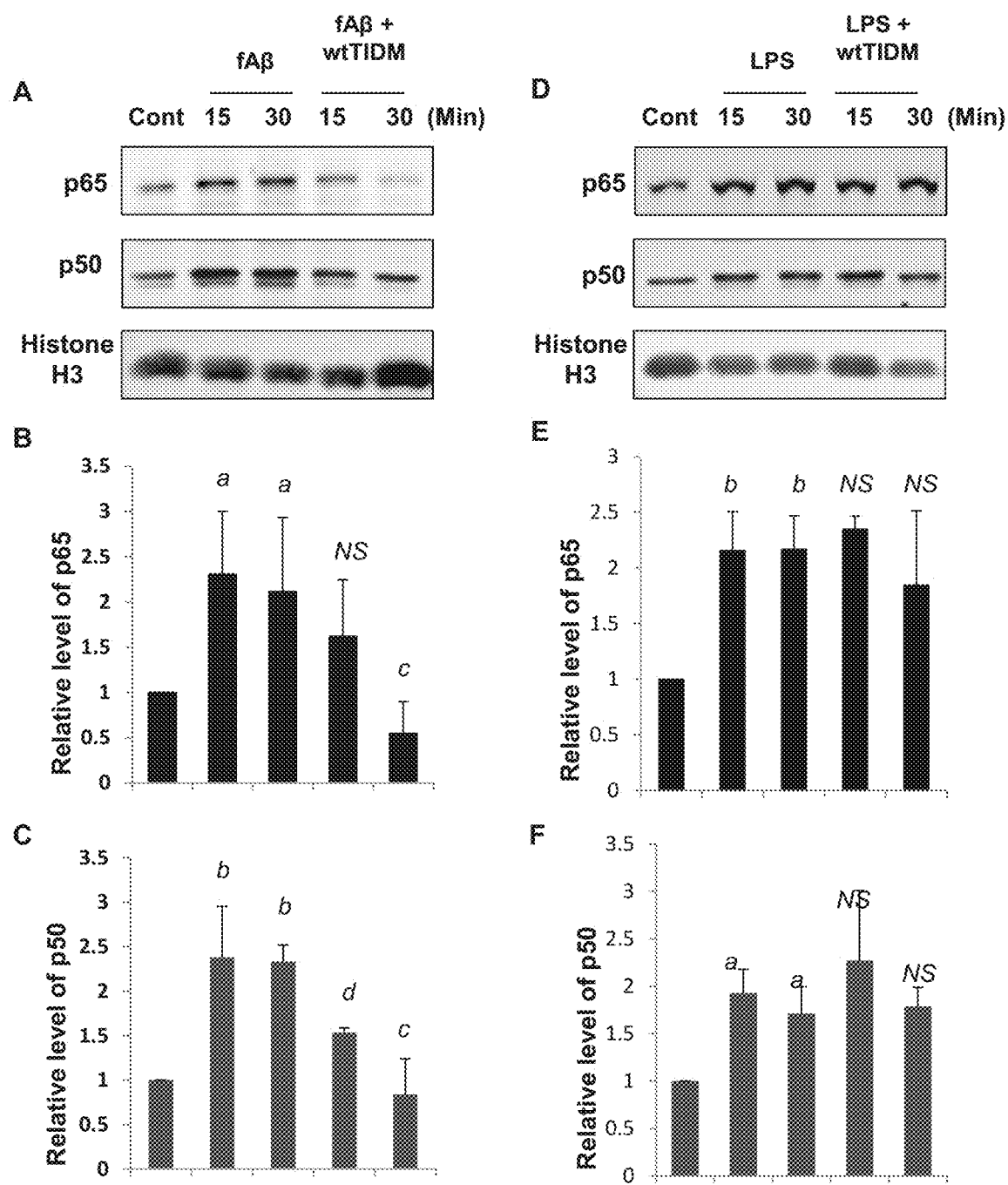
Figure 15 (A-F)

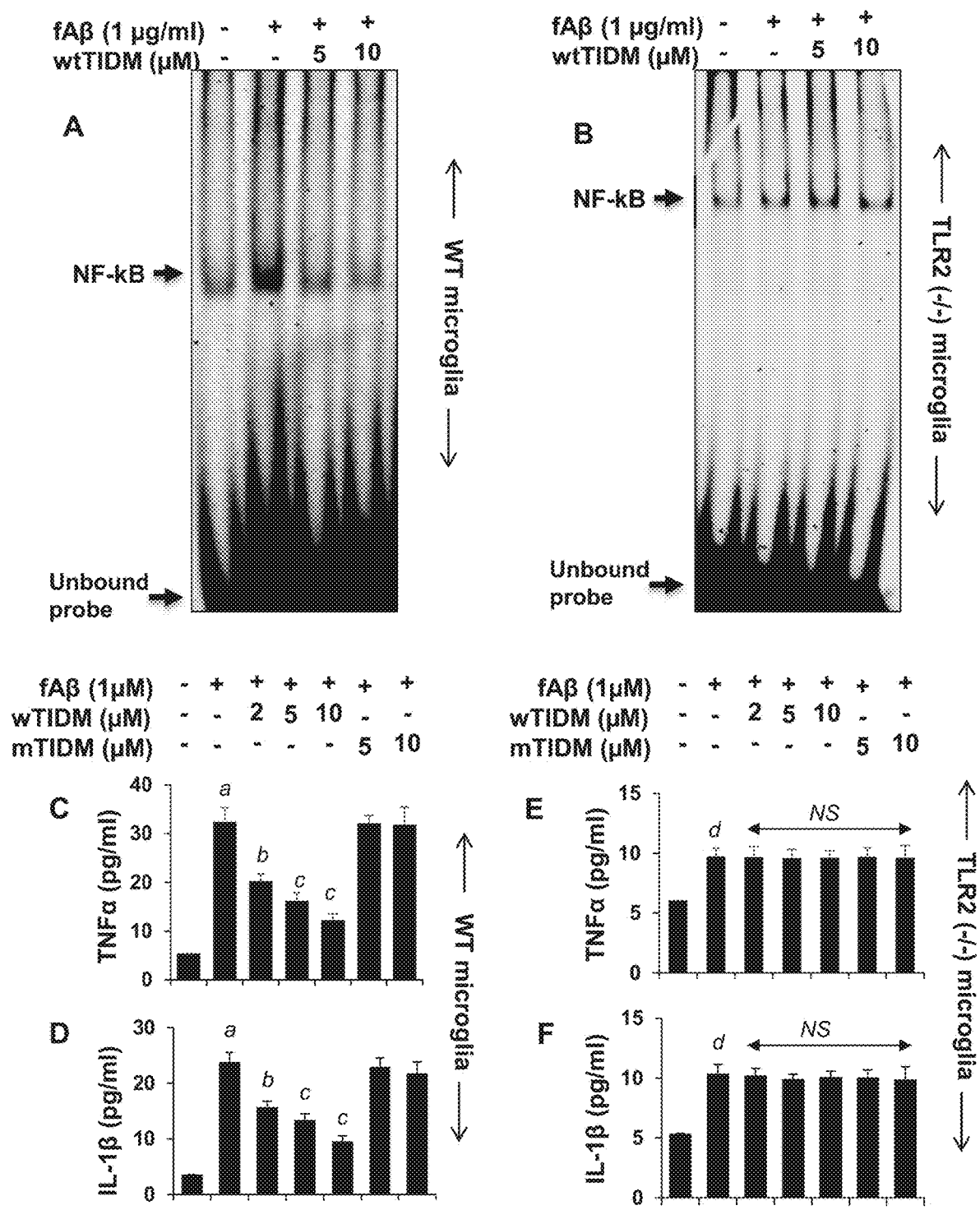
Figure 16 (A_F)

SL, Stride length; SWL, Sway length; PL, Print length; TS, Toe spread

Figure 25 (A-D)

SL, Stride length; SWL, Sway length; PL, Print length; TS, Toe spread

Figure 26 (A-D)

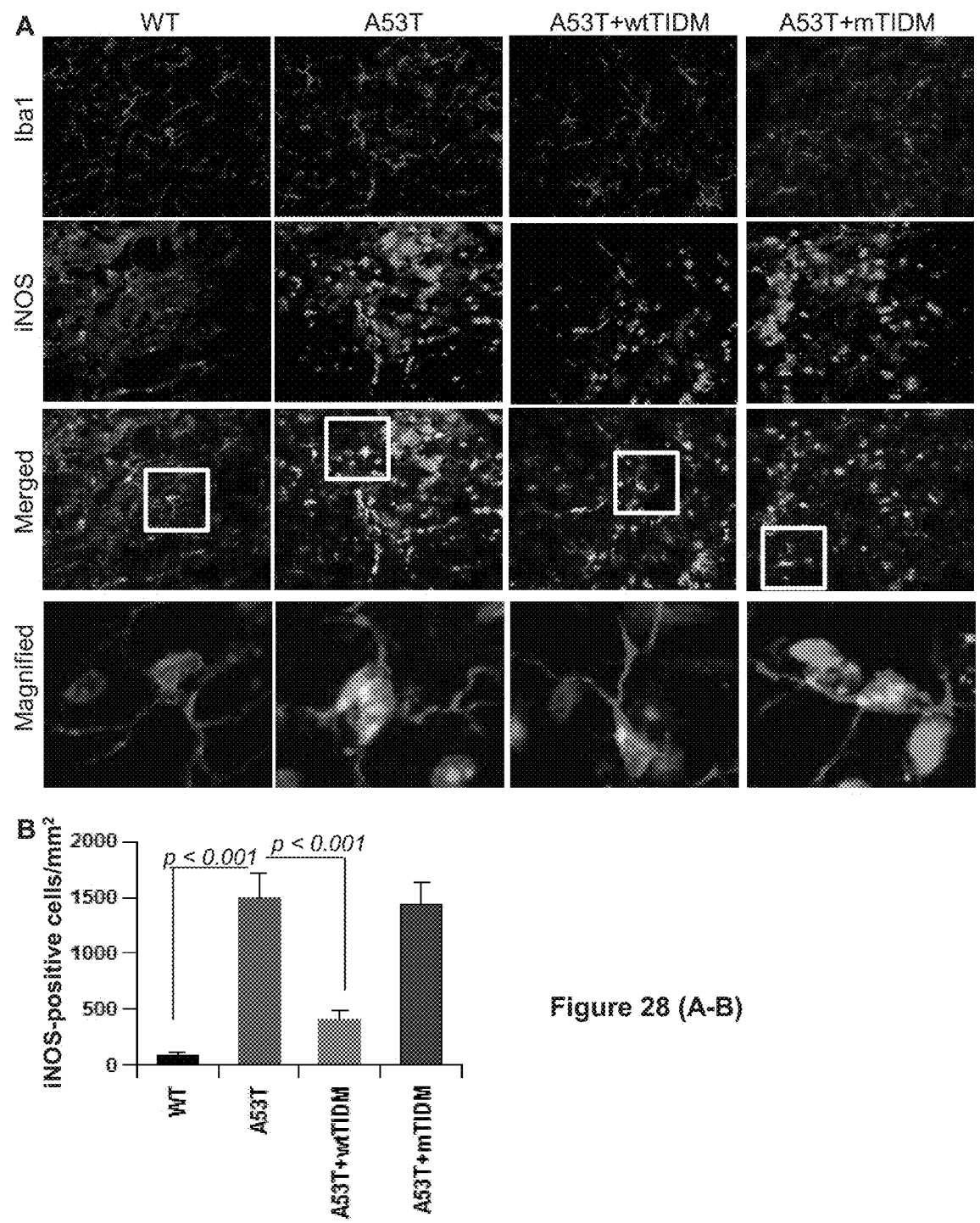
Figure 28 (A-B)

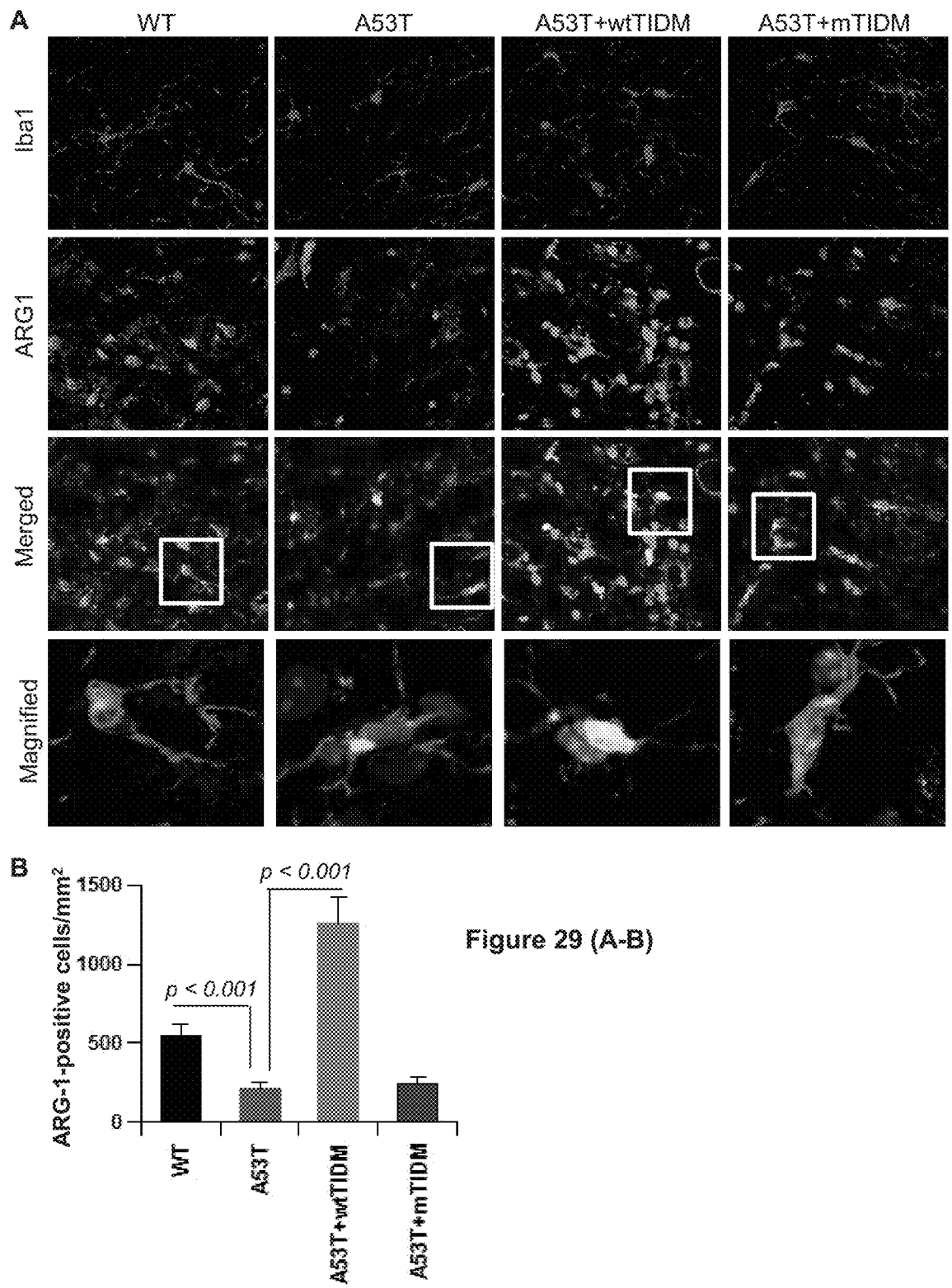
Figure 29 (A-B)

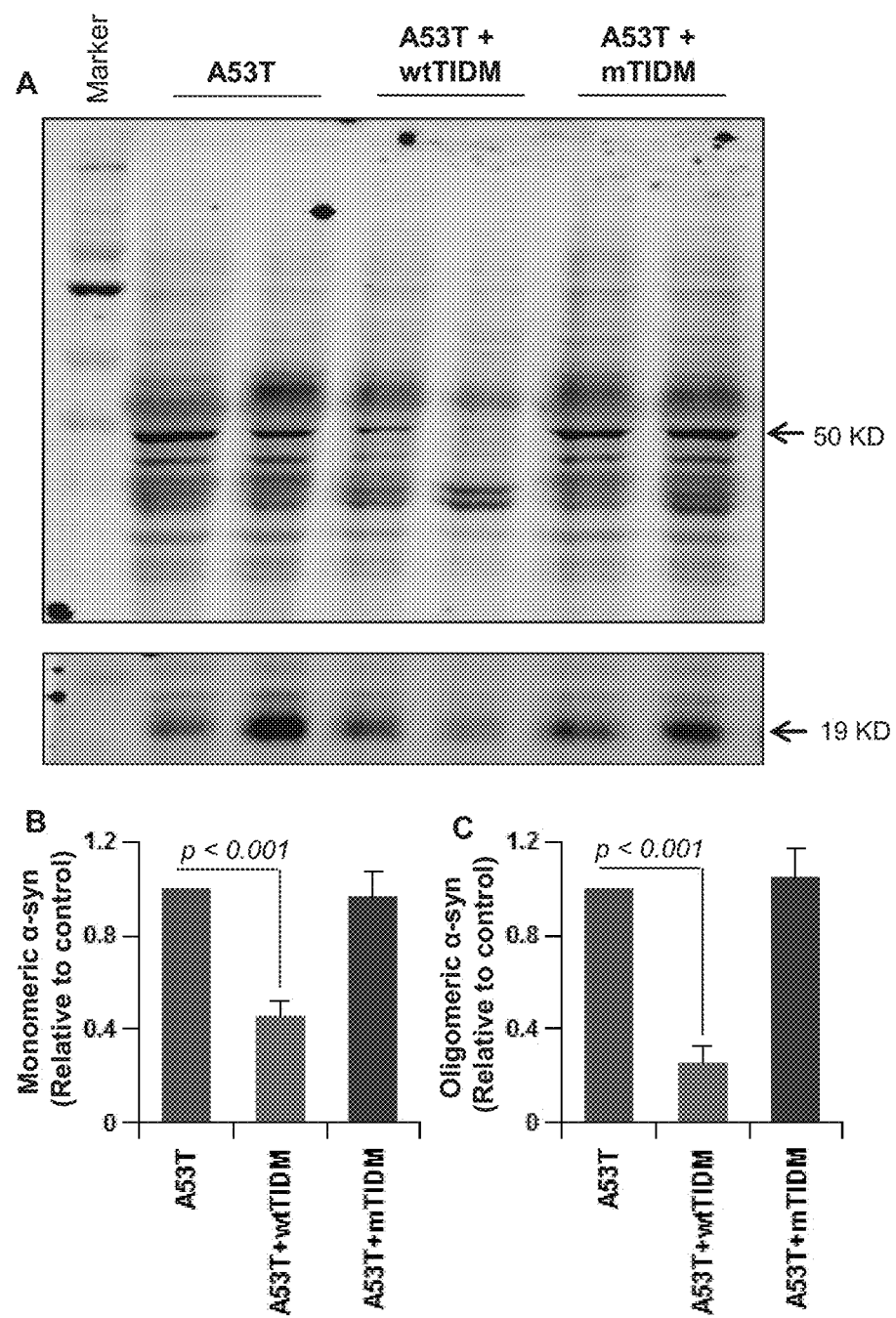
Figure 30 (A-C)

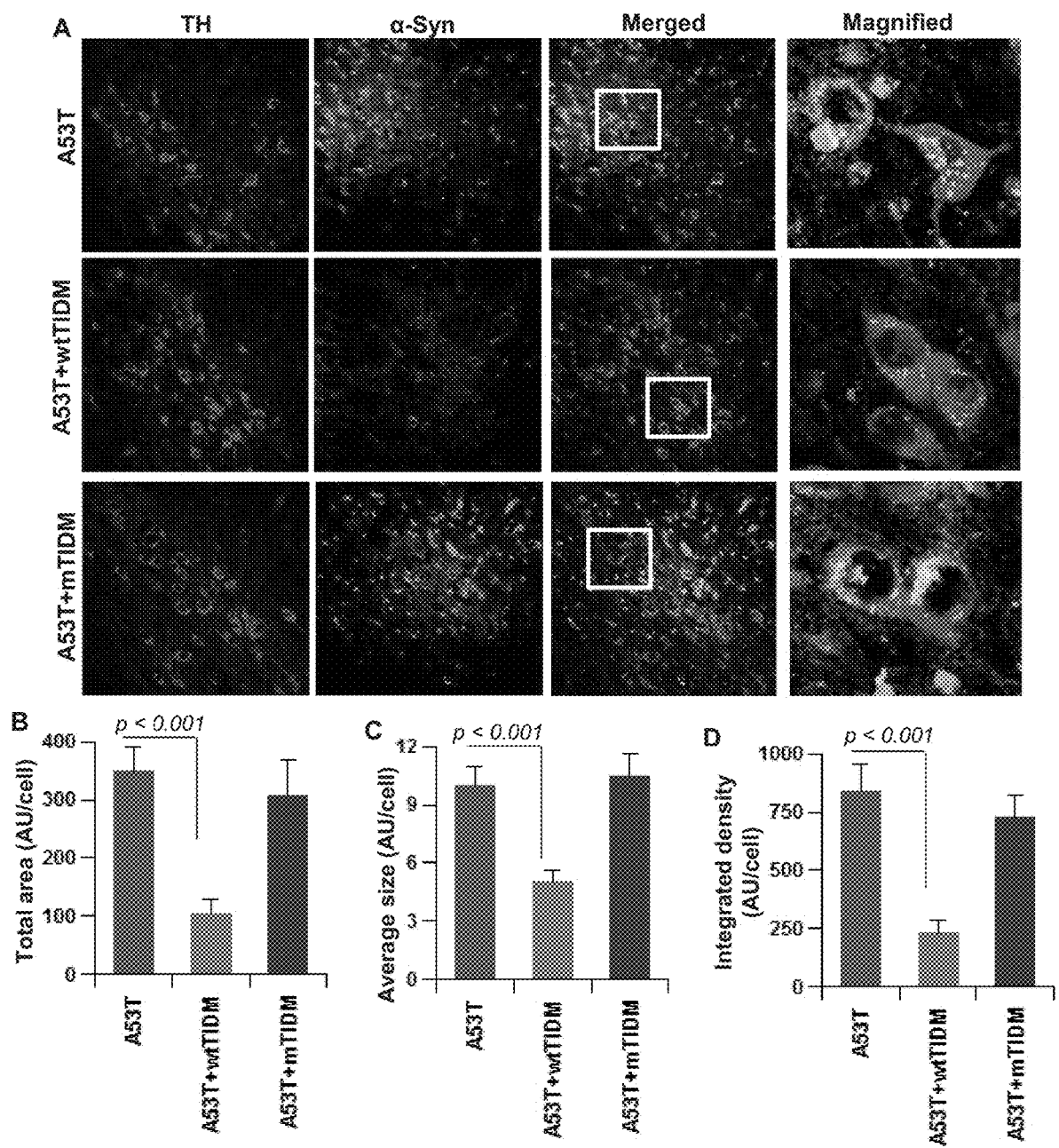
Figure 31 (A-D)

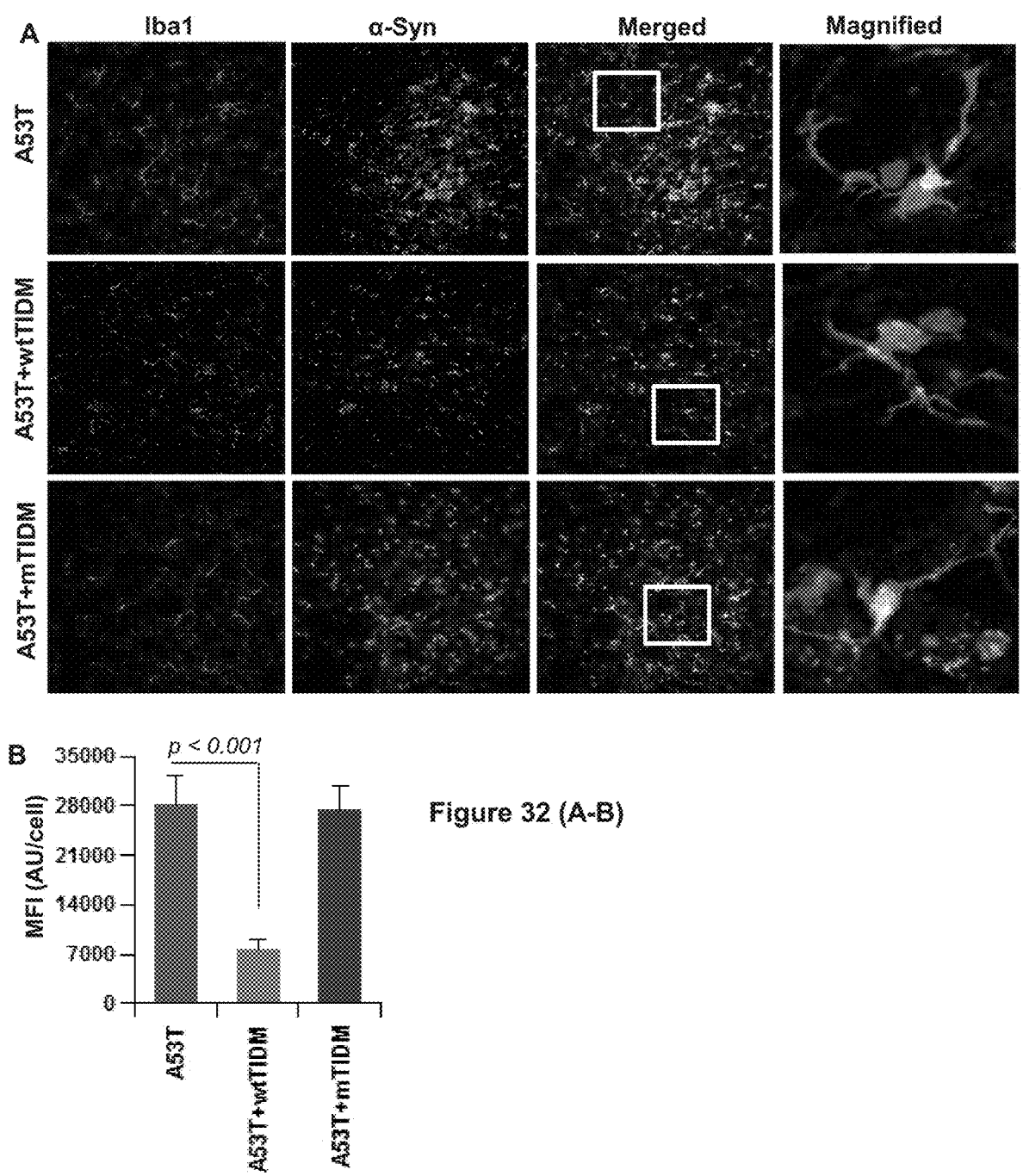
Figure 32 (A-B)

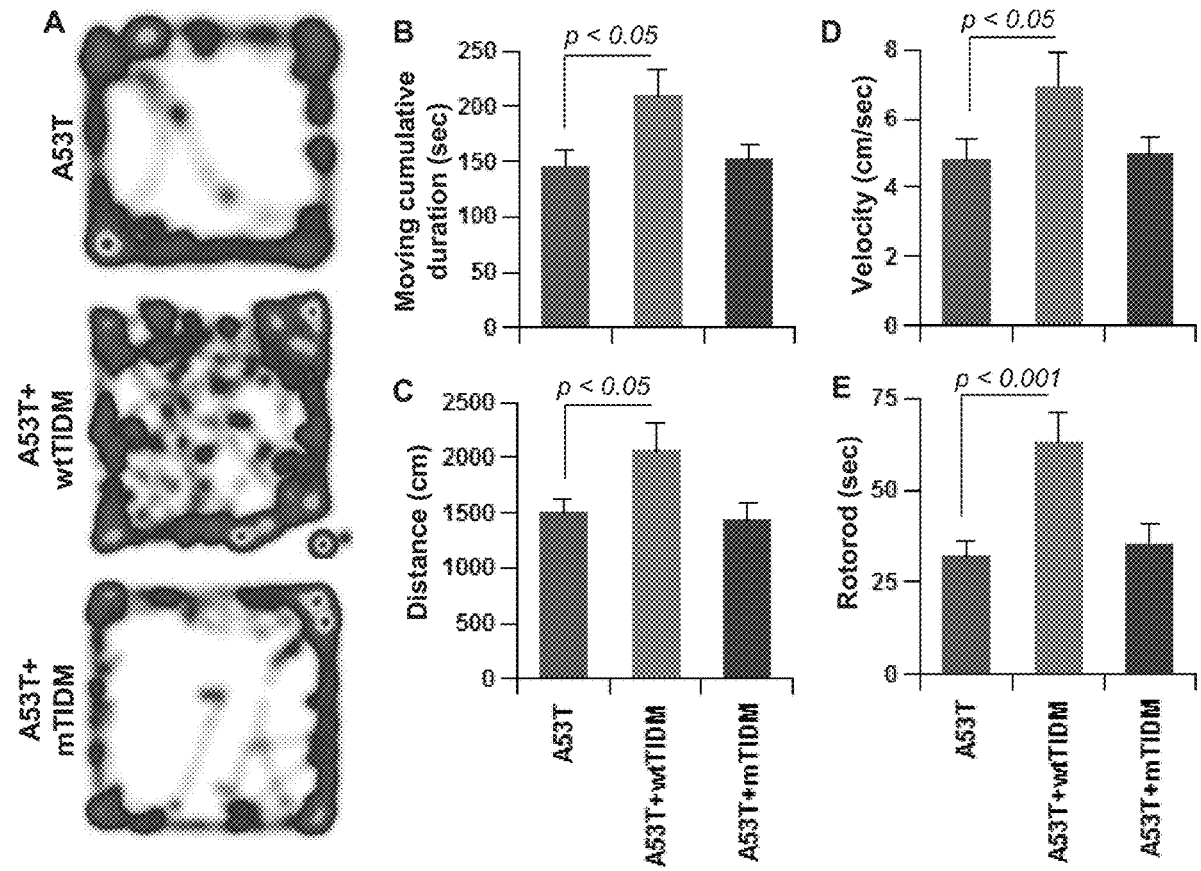
Figure 33 (A-D)

```
                          SEQUENCE LISTING

<160> NUMBER OF SEQ ID NOS: 3

<210> SEQ ID NO 1
<211> LENGTH: 6
<212> TYPE: PRT
<213> ORGANISM: Artificial Sequence
<220> FEATURE:
<223> OTHER INFORMATION: TLR2-interacting domain of MyD88 (TIDM)

<400> SEQUENCE: 1

Pro Gly Ala His Gln Lys
1               5

<210> SEQ ID NO 2
<211> LENGTH: 23
<212> TYPE: PRT
<213> ORGANISM: Homo sapiens

<400> SEQUENCE: 2

Asp Arg Gln Ile Lys Ile Trp Phe Gln Asn Arg Arg Met Lys Trp Lys
1               5                   10                  15

Lys Pro Gly Ala His Gln Lys
            20

<210> SEQ ID NO 3
<211> LENGTH: 23
<212> TYPE: PRT
<213> ORGANISM: Artificial Sequence
<220> FEATURE:
<223> OTHER INFORMATION: Mutated (m) TIDM

<400> SEQUENCE: 3

Asp Arg Gln Ile Lys Ile Trp Phe Gln Asn Arg Arg Met Lys Trp Lys
1               5                   10                  15

Lys Pro Gly Trp His Gln Asp
            20
```

COMPOSITIONS AND METHODS FOR TREATING NEUROLOGICAL AND OTHER DISORDERS

RELATED APPLICATIONS

The present patent application claims the benefit of the filing date of U.S. Provisional Patent Application No. 62/612,906, filed Jan. 2, 2018, the contents of which is hereby incorporated by reference.

STATEMENT AS TO RIGHTS TO INVENTIONS MADE UNDER FEDERALLY SPONSORED RESEARCH AND DEVELOPMENT

This invention was made with Government support of grants from U.S. Army Medical Research and Materiel Command (W81XWH-12-1-0065) and NIH (AG050431), the Zenith Fellows Award (ZEN-17-438829) from Alzheimer's Association, and a merit award (1I01BX003033) from US Department of Veterans Affairs. The Federal Government has certain rights in this invention.

TECHNICAL FIELD

The present invention generally relates to methods for treating neurological and other disorders, including autoimmune disorders. One aspect of the invention relates to a method of treating a disorder in which Toll-like Receptor 2 (TLR2) activation by binding to myeloid differentiation primary response 88 (MyD88) plays a role in disease pathogenesis. In one embodiment the method includes the administration of a composition, including a peptide sequence, that inhibits the activation of TLR2 by MyD88.

BACKGROUND

Alzheimer's disease (AD) is the most common human neurodegenerative disorder that leads to memory loss. It is widely believed that AD is a multifactorial disorder affected by a mix of genetic, environmental, and lifestyle factors (1-3). Neuropathologically, AD is characterized by the presence of senile plaques and neurofibrillary tangles (NFT) (4-6). A number of studies (7-13) also suggest that glial activation and associated inflammation play an important role in disease pathogenesis and that regulation of neuroinflammation may have therapeutic interest in attenuating neurodegeneration in AD.

Toll-like receptors (TLRs) serve as important links between innate and adaptive immunity primarily by responding to bacteria, bacterial products, viruses, viral products, and flagellin (14, 15). Currently, 11 different TLRs have been reported to exist in human and all the major CNS cell types are known to express TLRs (15, 16). However, microglia are the only cells in the CNS that express nearly all the TLRs known to date (16). Aside from TLR3, every TLR requires MyD88 for downstream signaling (14, 15). The inventor (17) and others (18, 19) have shown that fibrillar Aβ peptides require TLR2 for microglial inflammation.

SUMMARY OF THE PREFERRED EMBODIMENTS

In one aspect, the present invention provides a method for treating a disorder in a patent, where the disorder is one in which TLR2-MyD88 signaling plays a role in disease pathogenesis. In one embodiment, the method includes administering to the patient in need of such treatment a therapeutically effective amount of a composition including of a peptide containing the TLR2-interacting domain of MyD88. The therapeutically effective amount is an amount that at least reduces TLR2-MyD88 signaling.

In one embodiment, wherein the TLR2-interacting domain of MyD88 includes the sequence PGAHQK (SEQ ID NO: 1). In another embodiment the TLR2-interacting domain of MyD88 contains between 6 and 10 amino acids, including the sequence PGAHQK (SEQ ID NO: 1). In yet another embodiment, the peptide further includes the Antennapedia homeodomain linked via its C-terminal to the N-terminal of a peptide comprising a TLR2-interacting domain of MyD88. In another embodiment, the peptide sequence is drqikiwfqnrrmkwkkPGAHQK (SEQ ID NO: 2). In yet another embodiment, the peptide is linked to a delivery vector providing at least one of intracellular delivery cell and access across the cross blood-brain barrier.

In certain embodiments, the disorder is a neurological disorder, for example Alzheimer's disease, Parkinson's disease, dementia with Lewy bodies, Huntington's disease or multiple system atrophy. In other embodiments, the disorder is an autoimmune disorder, for example multiple sclerosis or rheumatoid arthritis. In yet other embodiments, the disorder is a bacterial infection, fungal infection, parasitic infection, viral infection, sepsis or a brain abscess.

Another aspect of the invention provides a composition including the peptide sequence PGAHQK (SEQ ID NO: 1) linked to a delivery vector providing at least one of intracellular delivery cell and access across the cross blood-brain barrier. In one embodiment, the delivery vector is Antennapedia homeodomain. In another embodiment, the composition includes a peptide having the sequence drqikiwfqnrrmkwkkPGAHQK (SEQ ID NO: 2).

The composition may also include at least one pharmaceutically acceptable carrier. In some embodiments, the composition is administered intranasally. In other embodiments, the composition is administered by a route selected from the group consisting of the oral, subcutaneous, intra-articular, intradermal, intravenous, intraperitoneal and intramuscular routes.

BRIEF DESCRIPTION OF THE DRAWINGS

FIG. 1(A-S). Monitoring levels of TLR2, TLR4 and MyD88 in the CNS of cases clinically diagnosed as no cognitive impairment (NCI), mild cognitive impairment (MCI) and Alzheimer's disease (AD). (A) Pre-frontal cortex homogenates (25 µg) from NCI (light blue), MCI (dark blue) and AD (grey) were immunoblotted for TLR2, TLR4 and MyD88. Actin was used to normalize signals obtained by densitometric measurement (NIH ImageJ). Coomassie was used to verify protein loading. Twelve NCI, eleven MCI and ten AD cases were run in three independent experiments. MyD88 (B) was significantly elevated in AD relative to both NCI (p<0.001) and MCI (p<0.001). TLR2 (C) was significantly higher in AD compared with MCI subjects (p<0.05) by Kruskal-Wallis test. TLR4 (D) did not differ significantly across the three groups. MyD88 (E; 0.371, p=0.033) and TLR2 (F; 0.463, p=0.007) positively correlated with Braak score by Kruskal-Wallis test. No such correlation was found between TLR4 (G; −0.012, p=0.947) and Braak score. MyD88 negatively correlated with Mini-Mental State Examination (MMSE) scores (H; −0.538, p=0.001) and global cognitive z score (GCS) index (I; −0.475, p=−0.005). However, the negative correlation was not significant for TLR2 with MMSE (J; −0.278, p=0.117) and GCS (K; −0.177, p=0.326). TLR4 was also not negatively correlated with MMSE (L; −0.173, p=0.336) and GCS (M; 0.047, p=0.794). kDa, kilodalton; OD, optical density. Hippocampal sections of NCI and AD brains were double-labeled with Iba-1 (microglia) and TLR2, TLR4 or MyD88. Cells positive for TLR2 (N, cortex; O, CA1), MyD88 (P, cortex; Q, CA1) and TLR4 (R, cortex; S, CA1) were counted in two sections (two images per slide) of each of four different cases. ap<0.001 vs NCI by two-sample t-tests. NS, not significant.

FIG. 2(A-H). Designing a peptide for disruption of TLR2 and MyD88 interaction. (A) A rigid-body in silico docked pose of mouse TLR2 (blue) and MyD88 (green) (electrostatic energy=−7.750 KCal/mol; desolvation energy=−24.99 Kcal/mol; VDW energy=105.25 Kcal/mol; Total energy=−22.216 KCal/mol) shows strong interaction between 245 to 250 amino acid of the CD loop of MyD88 and the BB loop of TLR2. Therefore, peptide corresponding to this domain of MyD88 (TIDM) was used to dissociate the interaction between TLR2 and MyD88. B) TLR2-MyD88 interaction was complexed with wtTIDM peptide (electrostatic energy=−4.516 KCal/mol; desolvation energy=−24.027 KCal/mol; VDW energy=16.724 KCal/mol; Total energy=−26.871 KCal/mol). C) Generation of cMyc-tagged C-terminal TLR2 (cTLR2) recombinant protein. The in vitro binding affinity of increasing doses of wtTIDM (D) and mTIDM (E) with cTLR2 was examined using surface plasmon resonance analyses (n=2 replicates/dose in 3 independent experiments). F) Plot of the binding response values versus the concentrations of wtTIDM (circle) and mTIDM (square) peptides. G) Melting curve of cTLR2 protein (black) alone and with wtTIDM (green). Thermal shift analyses showed 4.96° C. shift (ΔTm) of melting temperature (n=2 replicates/dose in 3 independent experiments). H) Melting curve of cTLR2 protein (black) alone and with mTIDM peptides (red) indicated a ΔTm of 0.87° C. (n=2 replicates/dose in 3 independent experiments).

FIG. 3(A-L). Selective disruption of TLR2 and MyD88 interaction by wtTIDM. In silico analyses of interactions of wtTIDM with TLR1, TLR4, TLR5, TLR6, TLR7, and TLR9. A rigid body interaction analyses were performed in pydock in silico analysis tool. Complexes of TLR1-wtTIDM (A), TLR4-wtTIDM (B), TLR5-wtTIDM (C), TLR6-wtTIDM (D), TLR7-wtTIDM (E), and TLR9-wtTIDM (F) were displayed. G) BV-2 microglial cells preincubated with wtTIDM and mTIDM peptides for 1 h were stimulated with 1 μM fibrillar AD 1-42 under serum-free condition. After 1 h, cellular extracts were immunoprecipitated with anti-MyD88 antibody followed by western blot of immunoprecipitates for TLR2. As control, cellular extracts were immunoprecipitated with normal IgG. Input was also immunoblotted with TLR2 and MyD88. H) Bands were scanned and values (TLR2/Input) presented as relative to control (n=2 replicates/condition in 3 independent experiments). Results were analyzed by two-sample t-tests. I) BV-2 microglial cells preincubated with wtTIDM and mTIDM peptides for 1 h were stimulated with LPS under serum-free condition. After 1 h, cellular extracts were immunoprecipitated with anti-MyD88 antibody followed by western blot of immunoprecipitates for TLR4. As control, cellular extracts were immunoprecipitated with normal IgG. Input was also immunoblotted with TLR4 and MyD88. J) Bands were scanned and values (TLR4/Input) presented as relative to control (n=2 replicates/condition in 3 independent experiments). Results were analyzed by two-sample t-tests. K) BV-2 microglial cells were transduced with pLenti-cMyc-cTlr2 lentivirions and 48 h after transduction, cells were treated with wtTIDM and mTIDM for 1 h followed by stimulation with fibrillar Aβ1-42. After 1 h, cellular extracts were immunoprecipitated with anti-MyD88 antibody followed by western blot of immunoprecipitates for c-Myc. Immuno-depleted (ID) fractions were also immunoblotted for c-Myc as control. L) Bands were scanned and values (c-Myc/Input) presented as relative to control (n=2 replicates/condition in 3 independent experiments). Results were analyzed by two-sample t-tests.

FIG. 5(A-Q). After intranasal delivery, wtTIDM peptide enters into the hippocampus and suppresses glial activation and reduces plaques in the hippocampus of Tg mice. Tg mice (6-month old) received one dose of wtTIDM peptide (0.1 mg/kg body wt) via intranasal route. After 60 min of treatment, mice were perfused with sterile saline and hippocampi were homogenized and supernatant was analyzed for wtTIDM by electrospray ionization-coupled mass spectrometry (ESI-MS) (A, wtTIDM standard; B, untreated Tg; C, wtTIDM-treated Tg). Tg mice were treated with wtTIDM and mTIDM peptides (0.1 mg/kg body wt/2d) via intranasal route. After 30d, hippocampal sections were double-labeled for Iba-1 & P-p65 (D) and Iba-1 & iNOS (FIG. 16). Cells positive for Iba-1 (E, CA1; F, CA3), P-p65 (G, CA1; H, CA3) and iNOS (I, CA1; J, CA3) were counted in two sections (two images per slide) of each of six different mice (n=6) per group. ap<0.001 vs non-Tg; bp<0.001 vs Tg by two-sample t-tests. Hippocampal extracts of all groups of mice (n=4 per group) were immunoblotted for iNOS (K). Actin was run as loading control. Bands were scanned and values (L, iNOS/Actin) presented as relative to non-Tg control. ap<0.001 vs non-Tg; bp<0.001 vs Tg by two-sample t-tests. M) Hippocampal sections were immunolabeled with 82E1 mAb. Amyloid plaques (N, cortex; O, hippocampus) were counted in two sections (two images per slide) of each of six different mice per group. ap<0.001 vs non-Tg; bp<0.001 vs Tg by two-sample t-tests. P) Hippocampal extracts (n=4 per group) were analyzed for Aβ by Western blot using 6E10 mAb. Arrowhead indicates 4 kDa Aβ band. Bands were scanned and values (Aβ/Actin) presented as relative to non-Tg control (Q). ap<0.001 vs non-Tg; bp<0.001 vs Tg by two-sample t-tests.

FIG. 6(A-N). Intranasal delivery of wtTIDM, but not mTIDM, peptide inhibits neuronal apoptosis in vivo in the hippocampus and improves memory and learning in Tg mice. Tg mice (6-month old) were treated with wtTIDM and mTIDM peptides (0.1 mg/kg body wt/2d) via intranasal route. After 30 d of treatment, mice were sacrificed and hippocampal sections were double-labeled for TUNEL & NeuN (A). TUNEL-positive cells (B, CA1; C, CA3) were counted in two sections (two images per slide) of each of six different mice (n=6) per group. ap<0.001 vs non-Tg; bp<0.001 vs Tg by two-sample t-tests. Hippocampal extracts of all groups of mice (n=4) were immunoblotted for cleaved caspase 3 (D). Actin was run as loading control. E) Bands were scanned and values (cleaved caspase 3/Actin) are presented as relative to non-Tg control. Results are expressed as mean+SEM of four mice per group. ap<0.001 vs non-Tg; bp<0.001 vs Tg by two-sample t-tests. Protein levels of PSD-95, NR2 A and GluR1 were monitored in hippocampal extracts by Western blot (F). Bands were scanned and values (G, PSD-95/Actin; H, NR2 A/Actin; I, GluR1/Actin) are presented as relative to non-Tg control. Results are expressed as mean+SEM of four mice per group. ap<0.001 vs non-Tg; bp<0.001 vs Tg by two-sample t-tests. Mice were tested for Barnes maze (J, latency; K, number of errors made) and T maze (L, number of positive turns; M, number of negative turns). Short-term memory was also monitored by novel object recognition test, which is represented by discrimination index (N). Eight mice (n=8) were used in each group and results were analyzed by one-way ANOVA.

FIG. 7(A-V). The wtTIDM, but not mTIDM, peptide protects mice from experimental allergic encephalomyelitis (EAE) and collagen-induced arthritis (CIA). A) EAE was induced in male C57/BL6 mice by MOG35-55 immunization and from 10 dpi, mice were treated with wtTIDM and mTIDM peptides (0.1 mg/kg body wt/d) via intranasal route. Mice (n=6 per group in two independent experiments) were scored daily. As evident by one-way repeated-measures ANOVA, the wtTIDM peptide significantly protected EAE [$F2, 94=22.59$ (>Fc=3.093)]. On 22 dpi, general motor activities were monitored using the Ethovision XT 13.0 Open Field Activity System (Noldus) (B, heat-map images representing overall motor activities; C, distance travelled; D, rearing; E, velocity; F, acceleration) and rotorod (G). Foot print analysis (H, stride length; I, print length; J, sway length; K, toe spread) was also performed. L) CIA was induced in male DBA/1J mice by bovine type II collagen immunization and from 29 dpi, mice were treated with wtTIDM and mTIDM peptides (1 mg/kg body wt/d) via i.p. injection. Mice (n=6 per group in two independent experiments) were scored daily. One-way repeated-measures ANOVA shows that the wtTIDM peptide significantly protected CIA [$F2, 45=4.927$ (>Fc=3.093)]. On 60 dpi, general motor activities were monitored by Ethovision System (M, heat-map images representing overall motor activities; N, distance travelled; O, rearing; P, velocity), rotorod (Q) and grip strength (R). Foot print analysis (S, stride length; T, print length; U, sway length; V, toe spread) was also performed. Six mice (n=6 per group) were used in two independent experiments. ap<0.001 & bp<0.05 vs control; cp<0.001 & dp<0.05 vs EAE or CIA by two-sample t-tests.

FIG. 8(A-D) Monitoring TLR2, TLR4 and MyD88 in the CNS of cases clinically diagnosed as no cognitive impairment (NCI) and Alzheimer's disease (AD). Hippocampal sections of NCI and AD brains were double-labeled with Iba-1 (microglia) & TLR2 (A), Iba-1 & MyD88 (B) and Iba-1 & TLR4 (C). Results represent analysis of two sections from each of four different brains. Cells positive for Iba1 (D, cortex; E, CA1) were counted in two sections (two images per slide) of each of four different cases. ap<0.001 vs NCI by two-sample t-tests.

FIG. 9(A-D). Status of TLR2 in the CNS of non-Tg and Tg (5xFAD) mice. A-B) Hippocampal sections of six-month old non-Tg and Tg mouse brains were double-labeled with Iba-1 (microglia) and TLR2. Results represent analysis of two sections from each of six different mice. C) Hippocampal extracts of all groups of mice (n=4) were immunoblotted for TLR2. Actin was run as loading control. D) Bands were scanned using the NIH Image J software and values (TLR2/Actin) are presented as relative to non-Tg control. ap<0.001 vs non-Tg by two-sample t-tests.

FIG. 10(A-D). Status of MyD88 in the CNS of non-Tg and Tg (5xFAD) mice. A-B) Hippocampal sections of six-month old non-Tg and Tg mouse brains were double-labeled with Iba-1 (microglia) and MyD88. Results represent analysis of two sections from each of six different mice. C) Hippocampal extracts of all groups of mice (n=4) were immunoblotted for MyD88. Actin was run as loading control. D) Bands were scanned using the NIH Image J software and values (MyD88/Actin) are presented as relative to non-Tg control. ap<0.001 vs non-Tg by two-sample t-tests.

FIG. 11(A-G). Implementation of in silico homology modeling strategy to build the structure of TLR-interacting domain of different mouse TLRs. Initial structures of TIRs (A, TLR1; B, TLR2; C, TLR4; D, TLR5; E, TLR6; F, TLR7; G, TLR9) were modeled by Deep View 3.7β2, an online macromolecular analytical tool of Expert Protein Analytical System (ExPASy). The quality of each modeled structure was evaluated with Quality Measurement Analysis tool (QMEAN).

FIG. 12(A-E). Docking analyses of wtTIDM and mTIDM complexed with TIR domain of TLR2 protein. A) In silico structural analysis of TIR domain of TLR2 and wtTIDM peptide. The docked pose was derived from pydock rigid-body protein-protein docking tool. The most stable structure was obtained from j mol viewer and displayed. B) Similar analysis was performed with mTIDM. C) Further analyses revealed a strong electrostatic interaction between wtTIDM and TLR2 (~2.31 A°: left) and a weak interaction with mTIDM (~7.26 A°; right) (D) A closer look of a complex between BB loop of TLR2 (blue) and CD loop of MYD88 (green). VDW droplets were shown to be overlapped with each other. E) The VDW clouds of MYD88 (pink) moved far from these of TLR2 (blue) when complexed with wtTIDM (green).

FIG. 13(A-F). Effect of wtTIDM and mTIDM peptides on the expression of proinflammatory molecules in microglial cells. BV-2 microglial cells preincubated with 10 μM wtTIDM/mTIDM peptides for 1 h were stimulated with 1 μM fibrillar Aβ1-42 (A), 1 μM MPP+(B), 250 ng/ml LTA (C), 1 μg/ml LPS (D), 1 μM flagellin (E), and 1 μM CpG DNA (F). After 4 h of stimulation, the mRNA expression of IL-1β and iNOS was monitored by RT-PCR (n=2 replicates/condition in 3 independent experiments).

FIG. 14(A-D). Effect of wtTIDM and mTIDM peptides on polyIC-mediated activation of NF-κB activation and the expression of proinflammatory molecules in microglial cells. BV-2 microglial cells preincubated with 10 μM wtTIDM/mTIDM peptides for 1 h were stimulated with 50 μM polyIC. A) After 1 h of stimulation, the activation of NF-κB was monitored in nuclear extracts by EMSA. After 4 h of stimulation, the mRNA expression of IL-1β and iNOS was monitored by semi-quantitative RT-PCR (B) and real-time PCR (C, IL-1β; D, iNOS) (n=2 replicates/condition in 3 independent experiments). ap<0.001 vs control; bp<0.001 vs stimuli by two-sample t-tests.

FIG. 15(A-F). Effect of wtTIDM peptide on fibrillar Aβ- and LPS-induced nuclear translocation of p65 and p50 in microglial cells. BV-2 microglial cells preincubated with 10 μM wtTIDM peptide for 1 h were stimulated with either 1 μM fibrillar Aβ1-42 (A-C) or 1 μg/ml LPS (D-F) under serum-free condition. At different minute intervals, levels of p65 and p50 (A, fibrillar Aβ; D, LPS) were monitored in nuclear extracts by Western blot. Histone H3 was run as a loading control. Bands were scanned and values of p65/H3 (B & E) and p50/H3 (C & F) are presented as relative to control (n=2 replicates/condition in 3 independent experiments). $ap<0.05$, $bp<0.001$ vs control; $cp<0.01$ vs 30 min stimulation; $dp<0.05$ vs 15 min stimulation; NS, not significant by two-sample t-tests.

FIG. 16(A-F). The wtTIDM peptide remained unable to inhibit fibrillar Aβ1-42 peptide-mediated activation of NF-κB and the expression of proinflammatory molecules in TLR2 (−/−) microglia. Primary microglia isolated from WT (A) and TLR2 (−/−) (B) mice were treated with different concentrations of wtTIDM peptide for 1 h followed by stimulation with 1 μM fibrillar Aβ1-42 under serum-free condition. After 1 h of stimulation, the activation of NF-κB was monitored by EMSA. WT (C & D) and TLR2 (−/−) (E & F) microglia were treated with different concentrations of wtTIDM and mTIDM peptides for 1 h followed by stimulation with 1 μM fibrillar Aβ1-42 under serum-free condition. After 18 h of stimulation, levels of TNFα (C & E) and IL-1β (D & F) were monitored in supernatants by ELISA (n=2 replicates/condition in 3 independent experiments). $ap<0.001$ vs control; $bp<0.001$ vs stimuli by two-sample t-tests.

FIG. 28(A-B). Intranasal wtTIDM peptide attenuates microglial inflammation in the nigra of A53T α-syn Tg mice. A53T mice (male; 9-month old; n=6 per group) were treated with TIDM peptides via intranasal route at a dose of 0.1 mg/kg body wt/d for 30d followed by double-label immunofluorescence analysis of nigral sections for Iba-1 and inducible nitric oxide synthase (iNOS) (A). Magnified images of selected area are shown at the bottom row. The iNOS (+ve) cells were counted in two sections of each of six mice per group and presented as cells/mm2.

FIG. 29(A-B). Intranasal wtTIDM peptide stimulates microglial expression of arginase-1 in the nigra of A53T α-syn Tg mice. A53T mice (male; 9-month old; n=6 per group) were treated with TIDM peptides via intranasal route at a dose of 0.1 mg/kg body wt/d for 30d followed by double-label immunofluorescence analysis of nigral sections for Iba-1 and arginase-1 (ARG1) (A). Magnified images of selected area are shown at the bottom row. The ARG-1 (+ve) cells were counted in two sections of each of six mice per group and presented as cells/mm2.

FIG. 30(A-C). Intranasal wtTIDM peptide reduces α-synucleinopathy in the nigra of A53T α-syn Tg mice. A53T mice (male; 9-month old; n=6 per group) were treated with TIDM peptides via intranasal route at a dose of 0.1 mg/kg body wt/d for 30d followed by Western blot analysis of nigral extracts for α-syn (A). Bands were scanned and presented as relative to A53T control (B, monomeric α-syn; C, oligomeric α-syn). Results are mean+SEM of six mice per group.

FIG. 31(A-D). Intranasal wtTIDM peptide reduces α-synucleinopathy in the nigra of A53T α-syn Tg mice. A53T mice (male; 9-month old; n=6 per group) were treated with TIDM peptides via intranasal route at a dose of 0.1 mg/kg body wt/d for 30d followed by double-label immunofluorescence analysis of nigral sections for TH and α-syn (mjfr1 Ab) (A). Magnified images of selected area are shown at the leftmost column. Total area (B), average size (C) and integrated density (D) of α-syn-positive cell bodies were calculated. Five cells from each of two nigral sections of six mice per group were analyzed.

FIG. 32(A-B). Intranasal wtTIDM peptide reduces α-synucleinopathy in the nigra of A53T α-syn Tg mice. A53T mice (male; 9-month old; n=6 per group) were treated with TIDM peptides via intranasal route at a dose of 0.1 mg/kg body wt/d for 30d followed by double-label immunofluorescence analysis of nigral sections for microglial marker Iba-1 and α-syn (mjfr1 Ab) (A). Magnified images of selected area are shown at the leftmost column. Mean fluorescence intensity (MFI) of (α-syn+Iba-1)-positive cell bodies was calculated. Five cells from each of two nigral sections of six mice per group were analyzed.

FIG. 33(A-E). Intranasal wtTIDM peptide improve locomotor activities of A53T α-syn Tg mice. A53T mice (male; 9-month old; n=6 per group) were treated with TIDM peptides via intranasal route at a dose of 0.1 mg/kg body wt/d for 30d followed by monitoring locomotor activities by the Ethovision XT 13.0 Open Field Activity System (Noldus) (A, track plot; B, moving cumulative duration; C, distance; D, velocity; E, rotorod). Results are mean+SEM of six mice per group.

DETAILED DESCRIPTION OF THE PREFERRED EMBODIMENTS

Definitions

Figure 4S:
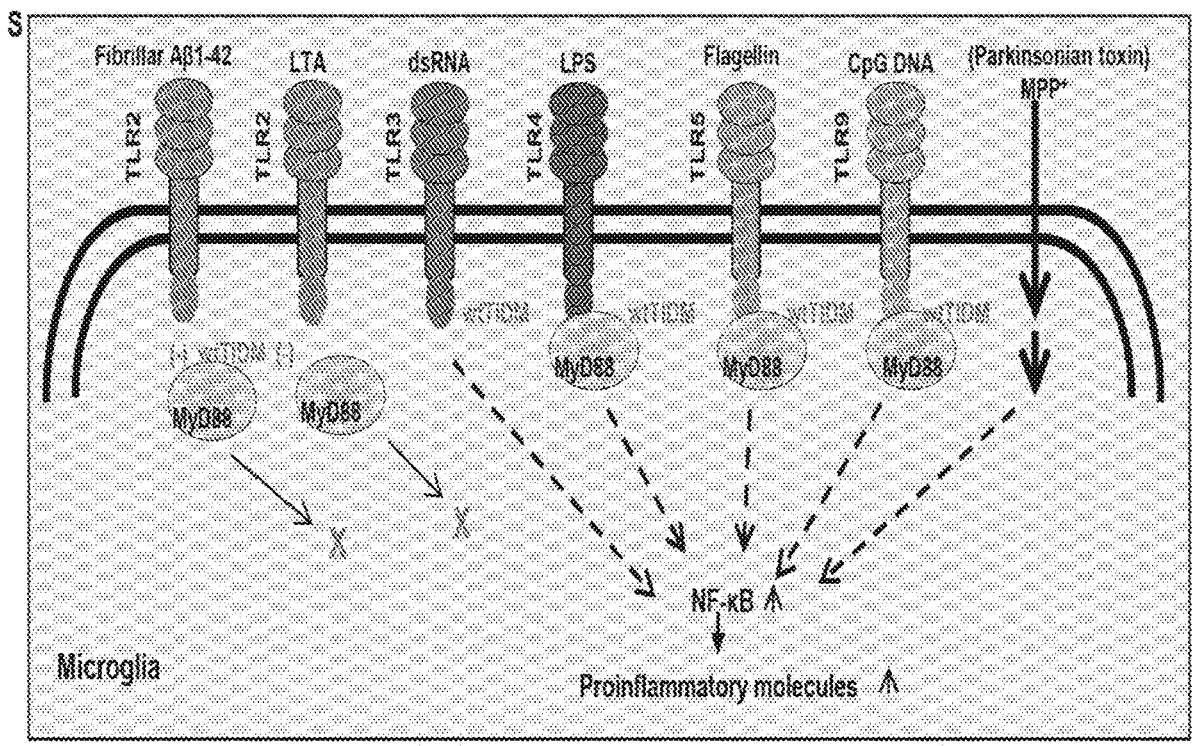
FIG. 4(A-R). Effect of wtTIDM and mTIDM peptides on the induction of NF-κB activation and the expression of proinflammatory molecules in microglial cells. BV-2 microglial cells preincubated with 10 μM wtTIDM/mTIDM peptides for 1 h were stimulated with 1 μM fibrillar Aβ1-42 (A-C), 1 μM MPP+ (D-F), 250 ng/ml LTA (G-I), 1 μg/ml LPS (J-L), 1 μM flagellin (M-O), and 1 μM CpG DNA (P-R) under serum-free condition. After 1 h of stimulation, the activation of NF-κB was monitored in nuclear extracts by EMSA (A, fibrillar AD; D, MPP+; G, LTA; J, LPS; M, flagellin, P; CpG DNA). After 4 h of stimulation, the mRNA expression of IL-1β (B, E, H, K, N, & Q) and iNOS (C, F, I, L, O, & R) was monitored by real-time PCR (B-C, fibrillar Aβ; E-F, MPP+; H-I, LTA; K-L, LPS; N-O, flagellin; Q-R, CpG DNA) (n=2 replicates/dose in 3 independent experiments). ap<0.001 vs control; bp<0.001 vs stimuli by two-sample t-tests.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as", "for example") provided herein, is intended merely to better illuminate the invention and does not pose a limitation on the scope of the invention unless otherwise claimed. No language in the specification should be construed as indicating any non-claimed element as essential to the practice of the invention.

The term "patient" refers of a human or veterinary patient. The term "therapeutic effect" as used herein means an effect which induces, ameliorates or otherwise causes an improvement in the pathological symptoms, disease progression or physiological conditions associated with or resistance to succumbing to a disorder, for example the neurological, autoimmune or other disclosed herein, of a human or veterinary patient. The term "therapeutically effective amount" as used with respect to a drug means an amount of the drug which imparts a therapeutic effect to the human or veterinary patient.

Compositions and methods providing selective disruption of TLR2/MyD88 interaction inhibit inflammation and attenuate neurological and other disease pathology.

The applicant has demonstrated that levels of TLR2 and MyD88 increased in vivo in the frontal cortex and hippocampus of AD patients and 5xFAD mice. No option is available for specific targeting of induced TLR2. The applicant has designed a peptide corresponding to the TLR2-interacting domain of MyD88 (TIDM) that specifically inhibited induced TLR2 signaling and fibrillar Aβ-mediated microglial inflammation without modulating double-stranded RNA-, bacterial LPS-, flagellin-, CpG DNA-, and 1-methyl-4-phenylpyridinium (MPP+)-mediated microglial activation. Moreover, intranasal administration of TIDM peptide resulted in reduction in hippocampal microglial activation, lowering of Aβ load, suppression of neuronal apoptosis, and improvement of memory and learning in 5×FAD mice, highlighting therapeutic promise of TIDM peptide in AD.

The present invention generally relates to compositions and methods of treating disorders in which elevated TLR2 activation plays a role in disease pathogenesis. One embodiment of the method includes administration of a therapeutically effective amount of a composition including a peptide sequence corresponding to the TLR2-interacting domain of MyD88 (TIDM) that binds to the BB loop of only TLR2, but not other TLRs, and disrupts the association between TLR2 and MyD88. The composition inhibits signaling pathways transduced by TLR2 only.

One embodiment provides a method for treating a disorder in a patent, the method comprising administering to the patient in need of such treatment a therapeutically effective amount of a composition comprising of a peptide comprising a TLR2-interacting domain of MyD88. The therapeutically effective amount is an amount that at least reduces TLR2-MyD88 signaling. The disorder is one in which TLR2-MyD88 signaling plays a role in disease pathogenesis. For example, the disorder may be a neurological disorder, such as Alzheimer's disease, Parkinson's disease, dementia with Lewy bodies, Huntington's disease or multiple system atrophy. In another embodiment, the disorder is an autoimmune disorder, such as multiple sclerosis or rheumatoid arthritis. In yet another embodiment, the disorder is a bacterial infection, fungal infection, parasitic infection, viral infection, sepsis or a brain abscess.

In one embodiment, the peptide including the TLR2-interacting domain of MyD88 includes the sequence PGAHQK (SEQ ID NO: 1). In other embodiments, the peptide contains between 6 and 10 amino acids including SEQ ID NO: 1. For example, the peptide may contain 6, 7, 8, 9 or 10 amino acids including SEQ ID NO: 1. In other embodiment, the peptide includes fewer than 12, 13, 14 or 15 amino acids.

In another embodiment, the peptide is linked to a delivery vector providing at least one of intracellular delivery cell and access across the cross blood-brain barrier. The delivery vector may be a peptide of other composition. In one embodiment, the delivery vector is Antennapedia homeodomain. For example, the Antennapedia homeodomain is linked via its C-terminal of to the N-terminal of a peptide comprising a TLR2-interacting domain of MyD88. In one preferred embodiment, the peptide sequence is drqikiwfqnrrmkwkkPGAHQK (SEQ ID NO: 2).

Deciphering the mechanism of the disease process of AD and developing an effective neuroprotective therapeutic approach to slow down or halt the disease progression are of paramount importance. TLRs are known to resolve innate immune response by perceiving pathogen-associated molecular patterns and endogenous damage-associated molecular patterns (15). Microglia in the CNS express most of the TLRs known to date and earlier the inventor has shown that out of different TLRs, fibrillar Aβ1-42 requires TLR2 to stimulate microglial inflammation (17). Accordingly, several studies have extended this finding either by demonstrating a direct interaction between TLR2 and Aβ or via CD14 (18, 19, 33). Here, the inventor describes an important role of TLR2 in Alzheimer's disease. Higher levels of TLR2 were detected in hippocampus and prefrontal cortex of persons with AD dementia compared to persons with MCI or NCI. Although some studies reported the involvement of TLR4 in Aβ-mediated microglial activation, the inventor did not find higher levels of TLR4 in the CNS of persons with AD dementia indicating the specificity of our finding. TLR2 polymorphism has been reported to influence the susceptibility of AD (34) and PBMC of AD patients also express increased level of TLR2 (35). Consistent to TLR2, it also observed upregulation of MyD88 in the CNS of persons with AD dementia and interestingly, both TLR2 and MyD88 positively correlated with Braak score. MyD88 also correlated negatively with cognitive function.

Although TLR2 is an important member of innate immunity, there was no specific inhibitor for targeting TLR2. Therefore, through structural analysis of the interaction between TLR2 and MyD88, we have designed a peptide corresponding to the TLR2-interacting domain of MyD88 (TIDM) from the CD loop. Since the BB loop of TLR2 interacts with the CD loop of MyD88, wtTIDM peptide disrupts the association between TLR2 and MyD88. Interestingly, wtTIDM peptide docks in a way that it specifically targets the BB loop of TLR2, but not other TLRs, thereby inhibiting signaling pathways transduced by TLR2 only. Since wtTIDM peptide specifically targets TLR2 and fibrillar Aβ1-42 requires TLR2 for microglial activation (17, 18), wtTIDM peptide inhibits microglial NF-κB activation and inflammation induced by only LTA (a known agonist of TLR2) and fibrillar Aβ1-42, but not by MPP+, poly IC (an agonist of TLR3), LPS (an agonist of TLR4), flagellin (an agonist of TLR5), and CpG DNA (an agonist of TLR9), indicating the selective inhibition of TLR2 pathway by wtTIDM peptide. Moreover, consistent to the disruption of TLR2:MyD88 interaction, wtTIDM peptide does not function in the absence of TLR2.

Unmodified peptides usually have short half-lives due to rapid proteolysis in blood, kidneys, or liver and/or accelerated renal clearance, which are the major challenges of most peptide therapy. However, it has been shown that *Drosophila* antennapedia homeodomain-derived cell-penetrating peptide (Antennapedia homeodomain), penetratin, being rich in positively charged residues, helps cargo peptides to translocate into the cells, therefore avoiding rapid proteolysis (36, 37). Moreover, unmodified peptides do not enter into the CNS and the inventor has seen that penetratin can breach the tight endothelial network and carry peptides across the BBB (23, 38). Therefore, the efficacy of penetratin-containing wtTIDM peptide was tested in Tg mice and demonstrated that wtTIDM peptide reduced microglial inflammation, decreased neuronal apoptosis and protected cognitive function from AD toxicity. Our conclusions are based on the following. First, after intranasal administration, TIDM peptide entered into the hippocampus. Second, wtTIDM, but not mTIDM, peptide inhibited hippocampal activation of NF-κB and microglial inflammation in Tg mice. Third, wtTIDM, but not mTIDM, peptide protected hippocampal neurons and NMDA and AMPA receptor proteins from Alzheimer's toxicity in Tg mice. Fourth, wtTIDM, but not mTIDM, peptide also improved spatial learning and memory in Tg mice. Furthermore, the inventor did not notice any drug-related side effect (e.g. hair loss, appetite loss, weight loss, untoward infection, etc.) in any of the TIDM-treated mice used during the course of the study. However, one study has shown that genetic knockdown of TLR2 accelerates the cognitive decline in APP Tg mice (39). It is definitely possible as complete knockdown of TLR2 wipes out basal as well as induced TLR2 signaling pathways. Moreover, TLR2 has been shown to function via both MyD88-dependent and -independent pathways (40, 41) and the beauty of the current finding is that TIDM peptide targets only the MyD88-dependent induced TLR2 signaling pathway without inhibiting basal TLR2 activity.

Whether plaques are directly related to the loss of memory in AD or not, amyloid plaque is one of the pathological hallmarks in AD and it is also important to see that wtTIDM, but not mTIDM, peptide treatment reduced hippocampal plaque load in Tg mice. However, at present, it is not known how wtTIDM peptide treatment is coupled to plaque reduction. Beta-secretase 1 (BACE1) is the key enzyme that initiates the formation of Aβ and it has been shown that inhibition of NF-κB prevents Aβ-induced BACE1 promoter transactivation and that overexpression of wild-type or Swedish mutated βAPP does not modify the transactivation of BACE1 promoter constructs lacking NF-κB-responsive element (42). Since wtTIDM peptide suppresses fibrillar Aβ-induced activation of NF-κB, it is possible that wtTIDM peptide reduces the plaque burden in Tg mice via attenuation of the NF-κB-BACE1 pathway.

There is no effective therapy for halting the progression of AD. Administration of different inhibitors of cholinesterase such as Aricept®, Exelon®, Razadyne®, Cognex® etc. has been the standard treatment for AD (43). However, it is often associated with a number of side effects and unsatisfactory outcomes. Here, the inventor has demonstrated that levels of TLR2 and MyD88 are upregulated in the CNS of AD patients, that TLR2 and MyD88 positively correlate with Braak score, that wtTIDM peptide targets only TLR2 without modulating other signaling pathways, and that after intranasal administration, wtTIDM peptide reaches the hippocampus, suppresses hippocampal NF-κB activation, inhibits microglial inflammation, lowers cerebral plaque load, attenuates neuronal apoptosis, and protects learning and memory in Tg mice. These results suggest that selective targeting of TLR2 by intranasal wtTIDM peptide may have therapeutic importance in AD. Moreover, wtTIDM peptide also improved functional impairment and suppressed disease processes of EAE and CIA in mice. Therefore, in addition to AD, TIDM peptide may also open up an opportunity for a number of other disorders.

Pharmaceutical Compositions and Modes of Administration

The methods of treatment disclosed herein may include any number of modes of administering the peptide composition or pharmaceutical compositions of the peptide composition. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixers, solid emulsions, solid dispersions or dispersible powders. For the preparation of pharmaceutical compositions for oral administration, the peptide composition may be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. GELUCIRE®). In the pharmaceutical composition, the agent may also be dispersed in a microparticle, e.g. a nanoparticulate, composition.

For parenteral administration, the peptide composition or pharmaceutical compositions of the peptide composition can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration the agent or pharmaceutical compositions of the agent can be in the form of an aqueous, lipid, oily or other kind of solution or suspension or even administered in the form of liposomes or nano-suspensions.

In the treatment methods contemplated by the present disclosure, the peptide composition may be used alone or in compositions together with a pharmaceutically acceptable carrier or excipient. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Other suitable pharmaceutically acceptable excipients are described in "Remington's Pharmaceutical Sciences," Mack Pub. Co., New Jersey, 1991, the contents of which are expressly incorporated herein by reference.

In certain embodiments, the peptide composition may be orally administered to humans and other animals. The composition may be formulated for administration and methods of formulation are well known in the art (see, for example, Remington: The Science and Practice of Pharmacy, Mack Publishing Company, Easton, Pa., 19th Edition (1995)).

In some embodiments, the formulations may be sustained-release formulations, meaning that they release the peptide composition steadily over an extended period of time. In other embodiments, the formulations may be delayed-release formulations, meaning that they release the peptide composition at a time later than that immediately following its administration.

Pharmaceutical compositions for use in accordance with the present disclosure can be in the form of sterile, non-pyrogenic liquid solutions or suspensions, coated capsules, lyophilized powders, or other forms known in the art.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, EtOAc, benzyl alcohol, benzyl benzoate, propylene glycol, 1,3 butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

EXAMPLES

Example 1—Human Subjects

Thirty-three cases with ante mortem clinical diagnosis of no cognitive impairment (NCI; n=12), mild cognitive impairment (MCI; n=11), and AD (n=10) obtained from the Rush Religious Order Study (RROS) (44, 45) were analyzed (table S1). All participants agreed to a detailed annual clinical evaluation and brain donation upon death.

Example 2—Clinical and Neuropathologic Evaluations

Clinical criteria for diagnosis of NCI, MCI and AD have been reported elsewhere (44, 46). Final clinical and neuropsychological testing, which included the Mini-Mental State Examination (MMSE) and a battery of 19 cognitive tests, was performed within 2 years prior to death. A global cognitive z score (GCS) comprising the 19 tests was available for all cases (47). Braak staging of neurofibrillary tangles (NFTs) (48) was performed as previously described (44). Subjects with pathological findings other than AD (e.g. stroke, Parkinson disease, Lewy body dementia) were excluded from the study. Tissue and clinical information is under the protection of the Health Information Privacy Administration rules.

Example 3—Tissue Samples and Western Blotting

Superior frontal cortex (Brodmann area 9) was dissected free of white matter at autopsy on dry ice to prevent thawing and was maintained at −80° C. until assay. Tissue was homogenized and processed as described earlier (22). Tissue extracts and cell lysates (30 µg) were electrophoresed on 8 or 10% Bis-Tris SDS polyacrylamide gels in a continuous buffer system, transferred to nitrocellulose membranes (Bio-Rad) with a semi-dry blotter (Pierce) and immunoblotted as described earlier (22, 49-51). Blots were converted to binary, analyzed using ImageJ (NIH) and normalized to loading control (β-actin).

Example 4—Preparation of C-Terminal TLR2 (cTLR2)

TLR2 full-length construct (pLenti-cmyc-DDK/tlr2) was purchased from Origene. The cTLR2 (640-784 amino acids) tagged with c-myc was cloned in lenti vector using TOPO TA cloning kit (K5310-00; Life technologies). Briefly, a kozak sequence was incorporated in the upstream of C-terminal TIR domain of TLR2. Next, cTLR2 was cloned in lentivector followed by packaging in lentivirus using HEK293FT cells. After 48 h, media was collected and concentrated with Lenti-X Concentrator (Cat #631231; Clontech). This concentrated lentiviral sup was used for viral transduction. The cTLR2 protein was isolated from HEK293 cell lysate by passing through Myc affinity column. Purified protein was desalted and concentrated by using 10 kD molecular cut-off filtration system.

Example 5—Surface Plasmon Resonance

To analyze the binding of TLR2 with TIDM peptides, surface plasmon resonance (SPR) experiments were carried out using a Reichert 4SPR instrument (Reichert Technologies, Buffalo, N.Y.). Binding assay was performed using a 500 kDa Carboxymethyl Dextran Gold Sensor Slide (Reichert Inc.) for capturing TLR2. Protein immobilization was at a flow rate of 30 pl/min in PBS for 3 min with 0.8 mg/mL solution of TLR2. For analyte association, different concentrations of wtTIDM and mTIDM peptides in PBS running buffer were injected for 2.5 min at a rate of 30 µl/min followed by a dissociation phase of 3 min. The sensor surface was regenerated after each dissociation cycle by allowing buffer to flow at 40 µl/min for a minimum of 15 min. Signals obtained for the TLR2-bound surface were subtracted by signals obtained for the reference cell according to standard procedure using the system software. The concentration dependence of the subtracted signal was analyzed to determine binding affinity of TLR2 with wtTIDM and mTIDM peptides.

Example 6—Thermal Shift Assays

Thermal shift assays were performed in an Applied Biosystems 7500 standard real-time thermal cycler machine as described before (52, 53). For each reaction, purified protein (0.5 µg to 1p g) was added to 18 µL of thermal shift buffer provided with the kit, and 1-2 µL of dye. Reaction was set 96 well PCR plate in the dark and then placed in the thermal cycler machine using the following two-stage program [(25° C. for 2 mins) 1 cycle; (27° C. for 15 sec, 26° C. for 1 min) 70 cycles; auto increment 1° C. for both stages]. The filter was set at ROX with no quencher filter and no passive filter.

Example 7—in Silico Structural Analysis

The inventor utilized Deep View 3.7β2, an online macromolecular analytical tool of Expert Protein Analytical System (ExPASy), to model structures of TIR domains of different TLRs (TLR1, TLR2, TLR4, TLR5, TLR6, TLR7, and TLR9). In order to evaluate the quality of modeled structures, the inventor used Quality Measurement Analysis tool (QMEAN), a composite scoring tool that estimates the global quality of the entire model as well as the local per-residue analysis of different regions within a model. Residue-level interaction was evaluated by CO atom potential and long-range interactions were validated by all-atom potential. A solvation potential was implemented to analyze the burial status of the residues. The local geometry of each structure was analyzed by a torsion angle potential over three consecutive amino acids. The docked pose of TIR domains with either wtTIDM or mTIDM peptide was derived from pydock rigid-body protein-protein docking tool.

Example 8—Animals and Intranasal Delivery of TIDM Peptides

B6SJL-Tg (APPSwFlLon, PSEN1*M146L*L286V) 6799Vas/J transgenic (5×FAD or termed here as Tg) mice were purchased from Jackson Laboratories (Bar Harbor, Me.). Six-month old male Tg mice were treated intranasally with wtTIDM or mTIDM peptides (0.1 mg/Kg body wt/2d) for 30d. Briefly, TIDM peptides were dissolved in 5 µl normal saline, mice were hold in supine position and saline was delivered into one nostril using a pipetman.

Example 9—Induction of Chronic EAE and Treatment by TIDM Peptides

Male C57BL/6 mice were immunized with 100 µg of MOG35-55 as described (54, 55). Mice also received two doses of pertussis toxin (150 ng/mouse) on 0 and 2 days post-immunization (dpi). Starting from 10 dpi, mice received wtTIDM or mTIDM peptides (0.1 mg/Kg body wt/d) intranasally.

Example 10—Induction of Collagen-Induced Arthritis (CIA) and Treatment by TIDM Peptides Male DBA/1J mice (8-9 week old) were immunized intradermally at the base of the tail with 100 µg of bovine type II collagen emulsified in Incomplete Freund's Adjuvant and *M. tuberculosis* H37RA. On 21 dpi, mice were boosted with an intraperitoneal injection of 100 µg of bovine type II collagen. Mice were treated wtTIDM or mTIDM peptides (1 mg/Kg body wt/d) i.p. starting from 29 dpi.

Example 11—Preparation of Fibrillar Aβ1-42

Figure 27:
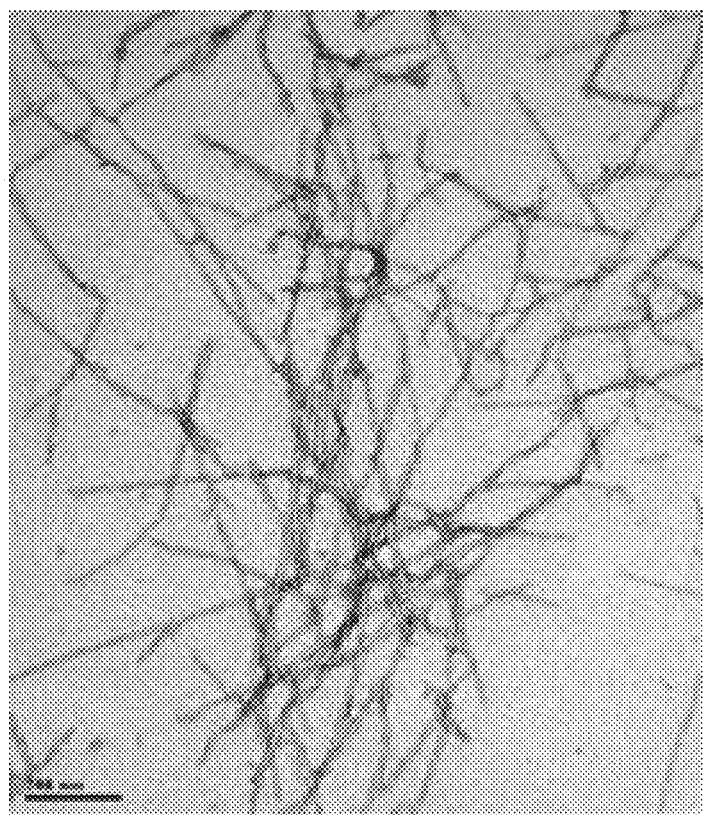
FIG. 27. Morphology of fibrillar Aβ1-42 peptides. Fibrillar Aβ1-42 peptides (Bachem Bioscience) were prepared by incubating freshly solubilized peptides at 50 µM in sterile distilled water at 37° C. for 5 days. Morphology of fibrillar Aβ1-42 peptides was examined by transmission electron microscopy.

Fibrillar Aβ1-42 (Anaspec, Fremont, Calif.) were prepared by incubating freshly solubilized peptides at 50 µM in sterile distilled water at 37° C. for 5 days (56). Please see FIG. 27 for morphology of fibrillar Aβ1-42.

Example 12—Semi-Quantitative RT-PCR Analysis

Total RNA was isolated from hippocampus using Ultraspec-II RNA reagent (Biotecx Laboratories, Inc., Houston, Tex.) following the manufacturer's protocol. To remove any contaminating genomic DNA, total RNA was digested with DNase. RT-PCR was carried out as described earlier (23, 57) using a RT-PCR kit (Clontech, Mountain View, Calif.).

Example 13—Real-Time PCR Analysis

DNase-digested RNA was analyzed by real-time PCR in the ABI-Prism7700 sequence detection system (Applied Biosystems, Foster City, Calif.) as described earlier (23, 57).

Example 14—Electrophoretic Mobility Shift Assay (EMSA)

Nuclear extracts were isolated and EMSA was carried out as described before (22, 23).

Example 15—Barnes Maze and T-Maze

Maze experiments were performed as described by us (52, 57). Briefly, for Barnes maze, mice were trained for 2 consecutive days followed by examination on day 3. After each training session, maze and escape tunnel were thoroughly cleaned with a mild detergent to avoid instinctive odor avoidance due to mouse's odor from the familiar object. On day 3, the maze was illuminated with high wattage light that generated enough light and heat to motivate animals to enter into the escape tunnel, allowing us to measure latency (duration before all four paws were on the floor of the escape box) and errors (incorrect responses before all four paws were on the floor of the escape box).

For T-maze, mice were also habituated in the T-maze for two days under food-deprived conditions so that animals can eat food rewards at least five times during 10 minutes period of training. During each trial, mice were placed in the start point for 30 s and then forced to make a right arm turn which was always baited with color food chips. After each training session, T-maze was thoroughly cleaned with a mild detergent. On day 3, mice were tested for making positive turns and negative turns. The reward side is always associated with a visual cue. Number of times the animal eats the food reward would be considered as a positive turn.

Example 16—Novel Object Recognition Task

Novel object recognition task was performed to monitor the short term memory as described by others (58) and us (57). Briefly, during training, mice were placed in a square novel box (20 inches long by 8 inches high) surrounded with infrared sensor. Two plastic toys (between 2.5 and 3 inches)

that varied in color, shape, and texture were placed in specific locations in the environment 18 inches away from each other. The mice were able to explore freely the environment and objects for 15 min and then were placed back into their individual home cages. After 30 mins, mice were placed back into the environment with two objects in the same locations, but now one of the familiar objects was replaced with a third novel object. The mice were then again allowed to explore freely both objects for 15 min. The objects were thoroughly cleaned with a mild detergent.

Example 17—Immunohistochemistry

Mice were anesthetized with ketamine-xylazine injectables and perfused with PBS and then with 4% (w/v) paraformaldehyde in PBS followed by dissection of the brain from each mouse for immunofluorescence microscopy (23, 59). Briefly, samples were incubated in PBS containing 0.05% Tween 20 (PBST) and 10% sucrose for 3 h and then 30% sucrose overnight at 4° C. Brain was then embedded in O.C.T (Tissue Tech) at −80° C., and processed for conventional cryosectioning. Frozen sections (30 µm) were treated with cold ethanol (−20° C.) followed by two rinses in PBS, blocking with 3% BSA in PBST and double-labeling with two antibodies (table S3). After three washes in PBST, sections were further incubated with Cy2 and Cy5 (Jackson ImmunoResearch Laboratories, Inc.). The samples were mounted and observed under an Olympus IX81 fluorescence microscope. Counting analysis was performed using Olympus Microsuite V software with the help of touch counting module.

Example 18—Fragment End Labeling of DNA

It was performed using a commercially available kit (TdT FragEL™, Calbiochem) as described before (10, 22).

Example 19—ELISA for Aβ1-42 and Aβ1-40

Hippocampal tissues were homogenized in TBS, pelleted for 30 min×150,000 g. The pellet was resuspended in 3 volumes (wt/vol original tissue weight) of TBS+1% Triton X-100, pelleted for 30 min×150,000 g and the supernatant recovered and stored. Samples were assayed for protein concentration and diluted 10-fold prior to performing ELISA according to manufacturer's instruction (BioLegend).

Example 20—Statistical Analysis

Clinical and biochemical data of human tissues were compared across diagnoses using nonparametric tests (i.e., Kruskal-Wallis test or Fisher's exact test, with Dunn's correction for multiple comparisons), which are more robust to outliers, non-normality and unequal sample sizes. Two-tailed Spearman Rank-Order correlations assessed variable associations between cognitive test scores and protein optical densities. Correlations were unadjusted for demographic information (i.e., age, sex, etc.) as these metrics were not significantly different between clinical groups. Statistical tests were performed using SPSS 19 (IBM), and significance was set at α=0.05 (two-sided).

Mouse behavioral measures were examined by an independent one-way ANOVA using SPSS. Homogeneity of variance between test groups was examined using Levene's test. Post-hoc analyses were conducted using Tukey's or Games-Howell tests, where appropriate. Other data were expressed as means±SD of three independent experiments. Statistical differences between means were calculated by the Student's t-test (two-tailed). A p-value of less than 0.05 (p<0.05) was considered statistically significant.

Example 21—Study Approval

Human Investigations Committees of the Rush University Medical Center approved the RROS study. Animals were maintained, and experiments were conducted in accordance with National Institutes of Health guidelines and were approved by the Rush University Medical Center Institutional Animal Care and Use Committee.

Example 22—Upregulation of TLR2 in AD

To investigate the role of TLR2 in the pathogenesis of AD, the inventor monitored the level of TLR2 by immunoblot analysis in prefrontal cortex (PFC; Brodmann area 9) from 33 subjects who died with AD dementia (n=10), mild cognitive impairment (MCI; n=11) and age-matched individuals with no cognitive impairment (NCI; n=12) (table S1). In terms of age, sex, postmortem interval, brain weight, or Braak scores, no significant difference was found across the groups (table S1). For comparison, the inventor included TLR4. Since all the TLRs except TLR3 employ MyD88, the inventor also investigated MyD88. Levels of both TLR2 and MyD88 in PFC were significantly altered between groups, with AD cases expressing more TLR2 and MyD88 relative to NCI and MCI cases (FIG. 1A-C & table S2). In contrast, TLR4 level did not significantly differ across the groups (FIGS. 1A & D; table S2). The Spearman rank-order correlation showed that both TLR2 and MyD88 levels in prefrontal cortex were positively correlated with Braak staging (FIG. 1E-F & table S2). On the other hand, the inventor did not find any relationship between TLR4 and Braak score (FIG. 1G & table S2). Importantly, MyD88 was also negatively correlated with mini-mental state examination (MMSE) and global cognitive z score (GCS) (FIG. 1H-M & table S2).

To confirm these findings, the inventor performed double-label immunofluorescence analysis of hippocampal sections. As expected, the level of Iba-1 (microglial marker) was higher in the cortex and hippocampus of AD as compared to NCI (FIG. 8A-E). Similar to Western blot results, the inventor observed greater levels of TLR2 (FIG. 8A & FIG. 1N-O) and MyD88 (FIG. 8B & FIG. 1P-Q) in the cortex and hippocampus of AD brain compared with NCI. Again, there was no difference in TLR4 expression (FIG. 8C & FIG. 1R-S).

Example 23—Upregulation of TLR2 in 5×FAD Transgenic (Tg) Mice

Next, the inventor examined the status of TLR2 and MyD88 in the hippocampus of 5×FAD Tg mice. Similar to that observed in the CNS of AD subjects, the inventor noticed higher levels of TLR2 (FIG. 9A-B) and MyD88 (FIG. 10A-B) in cortex and different parts of hippocampus of Tg mice as compared to age-matched non-Tg mice. The inventor also found increased Iba-1 immunoreactivity and colocalization of many Iba-1-positive cells with TLR2 (FIG. 9B) and MyD88 (FIG. 10B) in the cortex and hippocampus of Tg mice. Western blot experiments also confirmed the increase in TLR2 (FIG. 9C-D) and MyD88 (FIG. 10C-D) in the hippocampus of Tg mice as compared to non-Tg mice.

Example 24—Designing of a Peptide Corresponding to the TLR2-Interacting Domain of Myd88 (TIDM) for Specific Targeting of TLR2

Since there is no specific inhibitor of TLR2, for the therapeutic purpose, the inventor attempted to target TLR2. After ligand binding, TLR2 functions through MyD88 (14, 15). Therefore, the inventor applied rigid-body protein-protein interaction tool to model the interaction between TLR-interacting domain (TIR) of TLR2 and MyD88. Since the crystal structures of TIRs of mouse TLRs were not available, the inventor adopted in silico homology modeling strategy to build 3D structures of TIRs from all different TLRs (FIG. 11A-G). Similar to previous finding (20), the docked pose of MyD88 and TIR complex as derived from the in silico modeling analyses revealed that the BB loop of TLR2 was engaged with the CD loop of MyD88 with a strong van der Waals (VDW) interaction (FIG. 2A). Therefore, the inventor designed the following peptide corresponding to the TLR2-interacting domain of MyD88 (TIDM) from the CD loop to disrupt the interaction between TLR2 and MyD88:

```
Wild type (wt) TIDM:
                                    (SED ID NO.: 2)
drqikiwfqnrrmkwkkPGAHQK Mutated (m) TIDM:
                                    (SEQ ID NO.: 3)
drqikiwfqnrrmkwkkPGWHQD
```

The inventor added the Antennapedia homeodomain (lowercase) (drqikiwfqnrrmkwkk) via its C-terminal to the N-terminal of these peptides to facilitate cell permeability. MyD88 segments are PGAHQK and PGWHQD, respectively. Mutations are A to W and K to D, respectively. Interestingly, when the interaction between TIR of TLR2 and MyD88 was modeled with wtTIDM peptide, the inventor observed that MyD88 was associated with a certain degree of rotation, leaving its CD loop far removed from the TLR2 BB loop (FIG. 2B). According to Pydock analysis, wtTIDM peptide was found to be docked in the interface of CD loop, αB helix and BB loop of TIR domain of TLR2 (FIG. 12A). That specific pose of wtTIDM peptide imposed its VDW surface to be distributed over the BB loop of TLR2 (FIG. 12A), which was not possible in case of mTIDM peptide (FIG. 12B). The inventor observed that there was a strong electrostatic interaction (2.31 A°) between NE1 atom of conserved histidine residue (H82) of CD loop and ND atom of histidine (H4) residue of wtTIDM peptide (FIG. 12C). The docked structures of mTIDM with TLR2 clearly indicated that there was a very weak electrostatic interaction (7.26 A°) between H82 residue of CD loop and H4 residue of mTIDM peptide (FIG. 12C; right panel). Moreover, mutation of wtTIDM from lysine to aspartate imposed a negative cloud, which also drove the C-terminal end of the mTIDM even further away from the BB loop and more towards the groove of the αB helix FIG. 12B). The inventor also measured the possibility of VDW interaction in that complex by measuring the distance of VDW droplets between two close residues of TLR2 and MyD88 (FIG. 12D). We observed that there was a significant VDW overlap between MyD88 and TLR2 in the absence of wtTIDM. However, when complexed with wtTIDM, the BB loop of TLR2 and the CD loop of MyD88 posed far away from each other, negating any possibility of VDW interaction (FIG. 12E). To compare the affinity of wtTIDM and mTIDM towards TLR2 from another angle, the inventor performed surface plasmon resonance (SPR) analysis. The inventor first cloned and purified the whole TLR2 protein. However, it was not stable and since the whole TLR2 protein is also not available, the inventor prepared only the C-terminal TIR domain of TLR2 protein (cTLR2) via viral cloning strategy and purified the protein by myc affinity column (FIG. 2C). Kinetic plots (FIG. 2D-E) clearly showed that increasing doses of both wtTIDM and mTIDM displayed binding with the cTLR2. However, wtTIDM displayed much stronger affinity than mTIDM towards cTLR2 (FIG. 2D-F). According to the plot of SPR response at equilibrium versus peptide concentration (FIG. 2F), the affinity of wtTIDM (Kd=8 µM) for cTLR2 was approximately 2.5 times stronger than mTIDM (Kd=19 µM). To further substantiate, the inventor performed a thermal-shift assay, which revealed that 10 µM of wtTIDM peptide strongly shifted the melting curve of cTLR2 (FIG. 2G). On the other hand, very little shift was observed for mTIDM (FIG. 2H). Together, these results suggest that wtTIDM is a potent small-molecule peptide that strongly interferes with the interaction between TLR2 and MyD88.

Next, the inventor examined if wtTIDM had similar affinity towards other TLRs. Interestingly, the in silico analyses revealed that wtTIDM peptide docked far from the BB loop of TLR1 (FIG. 3A), TLR4 (FIG. 3B), TLR5 (FIG. 3C), TLR6 (FIG. 3D), TLR7 (FIG. 3E), and TLR9 (FIG. 3F), suggesting that wtTIDM specifically targets the BB loop of TLR2, but not other TLRs.

Next, the inventor examined if wtTIDM peptide could disrupt the physical association between endogenous TLR2 and MyD88. Earlier the inventor delineated that fibrillar Aβ1-42 activates microglia via TLR2 (17). Here, by immunoblot analysis of MyD88 immunoprecipitates with antibodies against TLR2, the inventor found that fibrillar Aβ1-42 treatment increased the association between TLR2 and MyD88 in microglial cells and that this interaction was inhibited by wtTIDM, but not mTIDM, peptide (FIG. 3G-H). Input showed the presence of equal amount of TLR2 and MyD88 under different treatment condition (FIG. 3G). To understand the specificity, we examined the effect of wtTIDM peptide on the interaction between TLR4 and MyD88. LPS is a prototype agonist of TLR4. LPS treatment increased the association between TLR4 and MyD88 in microglial cells (FIG. 3I-J) and in contrast to the suppression of TLR2:MyD88 interaction (FIG. 3G-H), wtTIDM peptide had no effect on the interaction between TLR4 and MyD88 (FIG. 3I-J). Next, we examined if wtTIDM could interfere with the interaction between MyD88 and newly-formed Myc-tagged C-terminal TLR2 (cTLR2). Therefore, microglial cells were transduced with pLenti-cMyc-cTlr2 lentivirions and after 48 h of transduction, cells were treated with fibrillar Aβ1-42 in the presence or absence of wtTIDM/mTIDM for 1 h. Immunoblot analysis of MyD88 immunoprecipitates with antibodies against c-Myc showed that the interaction between newly-formed cTLR2 and MyD88 in A01-42-treated microglial cells was inhibited by wtTIDM, but not mTIDM, peptide (FIG. 3K-L).

Example 25—TIDM Peptide Inhibits Microglial Inflammation Induced by Fibrillar Aβ1-42 and Lipoteichoic Acid (LTA), but not 1-Methyl-4-Phenylpyridinium (MPP+), Double-Stranded RNA (Poly IC), Bacterial Lipopolysaccharide (LPS), Flagellin, and CpG DNA Microglia expressing different TLRs are activated under various pathological conditions, such as neurodegeneration, inflammation, viral and bacterial infection, etc. (7, 21). Therefore, the inventor investigated if TIDM peptide was capable of suppressing microglial activation induced by different stimuli. Microglial cells pretreated with different concentrations of wtTIDM and mTIDM peptides for 1 h were stimulated with fibrillar Aβ1-42 (an etiological reagent of AD), MPP+ (a Parkinsonian toxin), LTA (agonist of TLR2), poly IC (agonist of TLR3), LPS (agonist of TLR4), flagellin (agonist of TLR5), and CpG DNA (agonist of TLR9). As expected, fibrillar A3 (FIG. 4A), MPP+(FIG. 4D), LTA (FIG. 4G), poly IC (FIG. 14A), LPS (FIG. 4J), flagellin (FIG. 4M), and CpG DNA (FIG. 4P) induced the activation of NF-κB in microglial cells. However, wtTIDM peptides inhibited fibrillar Aβ- and LTA-mediated activation of NF-κB (FIG. 4A & 4G). In contrast, wtTIDM peptides remained unable to suppress the activation of NF-κB in microglial cells induced by MPP+(FIG. 4D), poly IC (FIG. 14A), LPS (FIG. 4J), flagellin (FIG. 4M), and CpG DNA (FIG. 4P). These results were specific as mTIDM peptides had no effect on the activation of NF-κB induced by any of the stimuli. Activation of classical NF-κB pathway involves the phosphorylation of IκBα followed by nuclear translocation of p65 and p50. Therefore, the inventor also investigated the effect of wtTIDM peptide on nuclear translocation of p65 and p50 in activated microglia. As expected, increased nuclear translocation of p65 and p50 was observed in microglial cells in response to fibrillar Aβ1-42 (FIG. 15A-C) and LPS (FIG. 15D-F). However, wtTIDM peptide treatment inhibited nuclear translocation of p65 and p50 in microglial cells stimulated with fibrillar Aβ1-42 (FIG. 15A-C), but not LPS (FIG. 15D-F), indicating the specificity of wtTIDM peptide. To confirm these results, the inventor also monitored the expression of IL-1β and iNOS, proinflammatory molecules that are driven by NF-κB activation. All the stimuli induced the expression of IL-1β and iNOS in microglial cells (FIG. 4B-C, 4E-F, 4H-I, 4K-L, 4N-O, 4Q-R, FIG. 13A-F, & FIG. 14B-D). Consistent to the effect of wtTIDM on NF-κB activation, wtTIDM peptides inhibited the expression of proinflammatory molecules induced only by fibrillar Aβ (FIG. 13A & FIG. 4B-C) and LTA (FIG. 13C & FIG. 4H-I), but not MPP+(FIG. 13B & FIG. 4E-F), poly IC (FIG. 14B-D), LPS (FIG. S6D & FIG. 4K-L), flagellin (FIG. 13E & FIG. 4N-O), and CpG DNA (FIG. 13F & FIG. 4Q-R). These results suggest that wtTIDM peptide specifically inhibits microglial inflammation induced by agonists of TLR2, but not other TLRs.

Example 26—the wtTIDM Peptide does not Inhibit Fibrillar Aβ1-42-Induced Activation of Microglia in the Absence of TLR2

Since wtTIDM peptide disrupted the physical association between TLR2 and MyD88, as a mechanistic proof-of-principal, the inventor examined the effect of wtTIDM peptide on Aβ1-42-induced activation of Tlr2−/− microglia. Similar to BV-2 microglial cells, fibrillar Aβ1-42 peptides strongly induced the activation of NF-κB in primary microglia isolated from WT mice, which was inhibited by wtTIDM peptide (FIG. 16A). On the other hand, fibrillar Aβ1-42 peptides weakly induced the DNA-binding activity of NF-κB in Tlr2−/− microglia (FIG. 16A). However, in contrast to WT microglia, wtTIDM peptide remained unable to inhibit fibrillar Aβ1-42-induced activation of NF-κB in Tlr2−/− microglia (FIG. 16A-B). To further confirm, we also measured levels of common proinflammatory cytokines (TNFα and IL-1β) in supernatants. Similar to NF-κB activation, the induction of TNFα and IL-1β production by fibrillar Aβ1-42 was low in Tlr2−/− microglia as compared to WT microglia (FIG. 16C-F). However, wtTIDM peptide inhibited fibrillar Aβ1-42 peptide-induced production of TNFα and IL-1β in WT, but not Tlr2−/−, microglia (FIG. 16C-F), suggesting that wtTIDM peptide needs TLR2 to exhibit its function.

Figure 17:
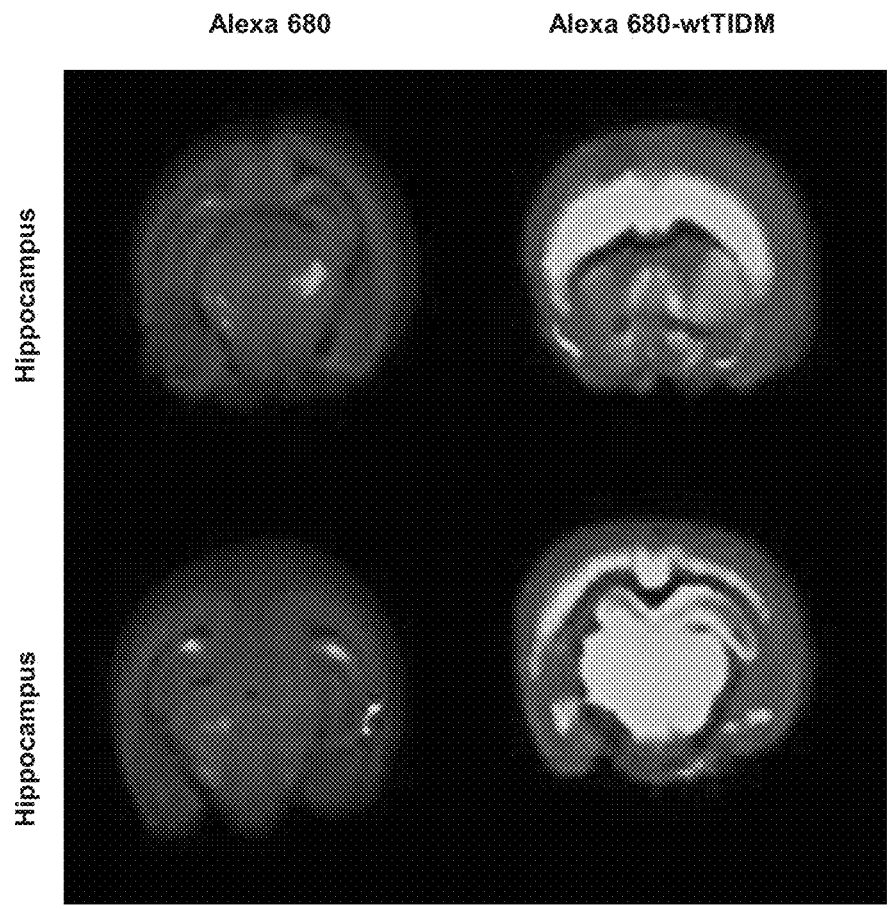
FIG. 17. After intranasal administration, wtTIDM peptide enters into the hippocampus of Tg mice. The wtTIDM peptide was labeled with Alexa 680-SE NIR dye (Life Technologies) following the manufacturer's protocol and Alexa 680-labeled peptide (2.5 μg) was administered to each mouse intranasally. Alexa 680-SE NIR dye was also administered as control. After 60 min, mice (n=3 in each group) were perfused with PBS and paraformaldehyde and hippocampal regions of the brain were scanned in Odyssey (ODY-0854, Licor-Inc) infra-red scanner at 700 and 800 nm channels. The red background came from 800 nm filter whereas the green signal was from Alexa 680-labeled NBD peptide at 700 nm channel.

Example 27—Intranasal Administration of wtTIDM Peptide Inhibits Inflammation, Reduces Plaque Load and Decreases Hyperphosphorylation of Tau in the Hippocampus of 5×FAD Tg Mice It is becoming clear that glial inflammation plays an important role in the loss of neurons in AD and other neurodegenerative disorders (7, 9, 22-24). Since wtTIDM peptide specifically inhibited fibrillar Aβ1-42-mediated microglial activation, the inventor decided to test its therapeutic translatability in 5×FAD Tg mice. The inventor first determined whether wtTIDM peptide could enter into the hippocampus. Tg mice were treated with TIDM peptides intranasally and after 60 min of administration, we detected wtTIDM peptide in the hippocampus of Tg mice by electrospray ionization-coupled mass spectrometry (FIGS. 5A & C). In contrast, the hippocampus of saline-treated Tg mice did not exhibit any peak for wtTIDM peptide (FIG. 5B). The level of wtTIDM peptide was 23.33±14.14 ng per gram brain tissue in the hippocampus of wtTIDM-treated Tg mice in comparison with nil in saline-treated Tg mice. By infrared scanning, we also detected TIDM peptide in hippocampus after intranasal treatment (FIG. 17). Therefore, after intranasal administration, TIDM peptide enters into the hippocampus.

Figure 18:
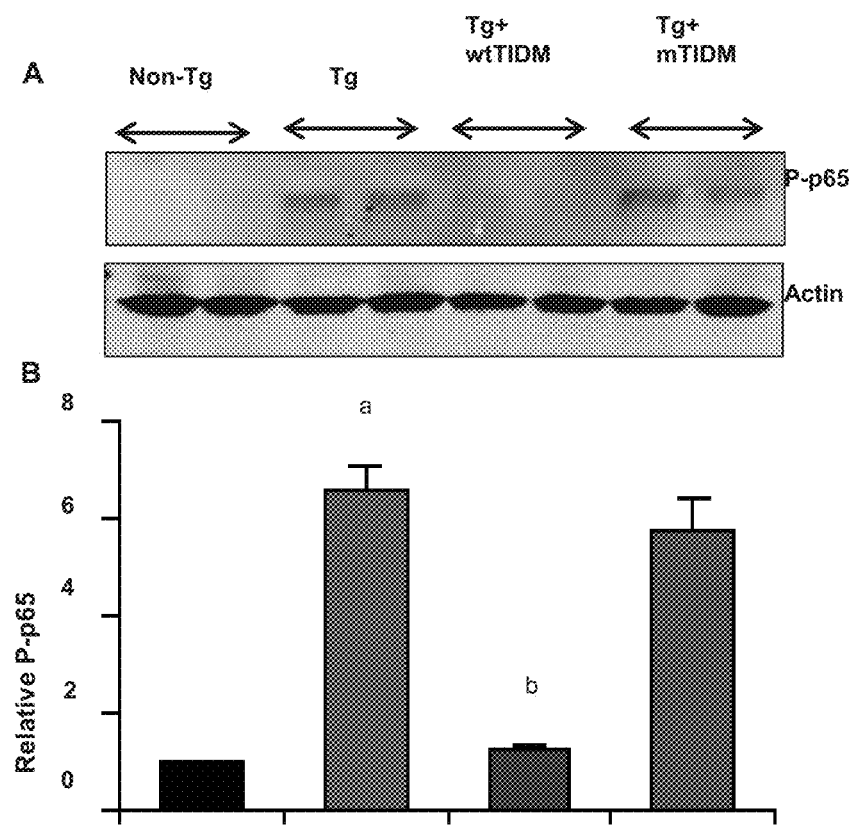
FIG. 18(A-B). After intranasal delivery, wtTIDM peptide suppresses the activation of NF-κB in the hippocampus of Tg mice. Tg mice (6-month old) were treated with wtTIDM and mTIDM peptides (0.1 mg/kg body wt/2d) via intranasal route. After 30d of treatment, hippocampal extracts of all groups of mice were immunoblotted for phospho-p65 (A). Actin was run as loading control. Bands were scanned and values (p-p65/Actin) are presented as relative to non-Tg control (n=4 in two independent experiments). $ap<0.001$ vs non-Tg; $bp<0.001$ vs Tg by two-sample t-tests.
Figure 19:
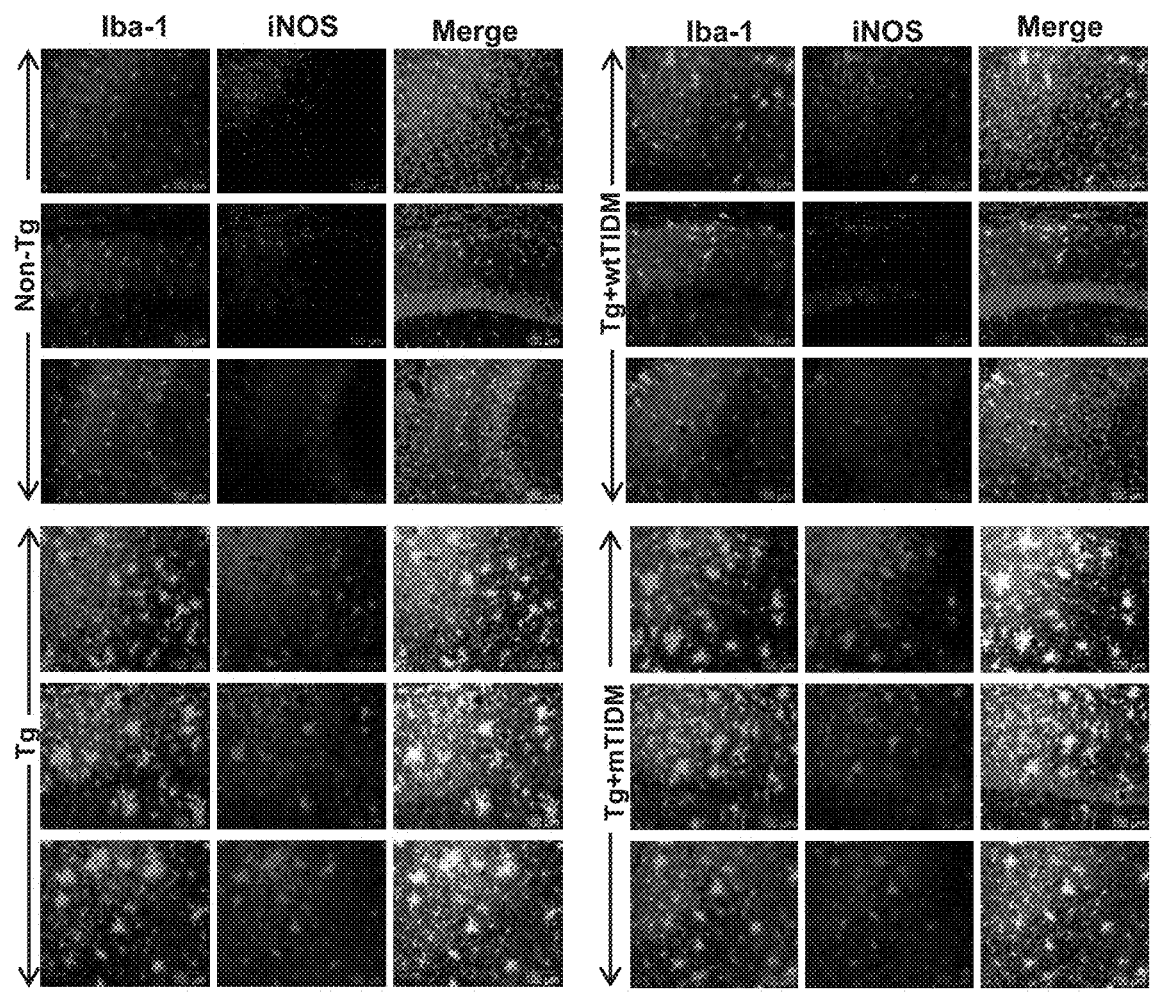
FIG. 19. Intranasal delivery of wtTIDM, but not mTIDM, peptide suppresses microglial expression of iNOS in the hippocampus of Tg mice. Tg mice (6-month old) were treated with wtTIDM and mTIDM peptides (0.1 mg/kg body wt/2d) via intranasal route. After 30d of treatment, mice were sacrificed and hippocampal sections were double-labeled for Iba-1 and iNOS. Results represent analysis of two sections from each of six different mice per group.

Next, the inventor investigated whether intranasal TIDM peptide was capable of modulating NF-κB activation in the hippocampus of Tg mice. As seen by double-label immunofluorescence of hippocampal sections, levels of Iba-1 and phospho-p65 were markedly higher in Tg mice as compared to non-Tg mice (FIG. 5D-H). However, intranasal treatment of Tg mice with wtTIDM, but not mTIDM, peptides led to the suppression of both Iba-1 and phospho-p65 in the hippocampus of Tg mice (FIG. 5D-H). This was also confirmed by Western blot analysis of hippocampal tissues (FIG. 18A-B). Moreover, activated microglia are known to express iNOS (21, 25). Accordingly, hippocampal microglia of Tg mice were also positive for iNOS (FIG. 19 & FIG. 5I-J). However, wtTIDM, but not mTIDM, peptide suppressed the expression of iNOS in the hippocampus of Tg mice (FIG. 19 & FIG. 5I-J). Western blot analysis also confirms inhibition of hippocampal iNOS expression by wtTIDM, but not mTIDM, peptide treatment (FIG. 5K-L).

Figure 20:
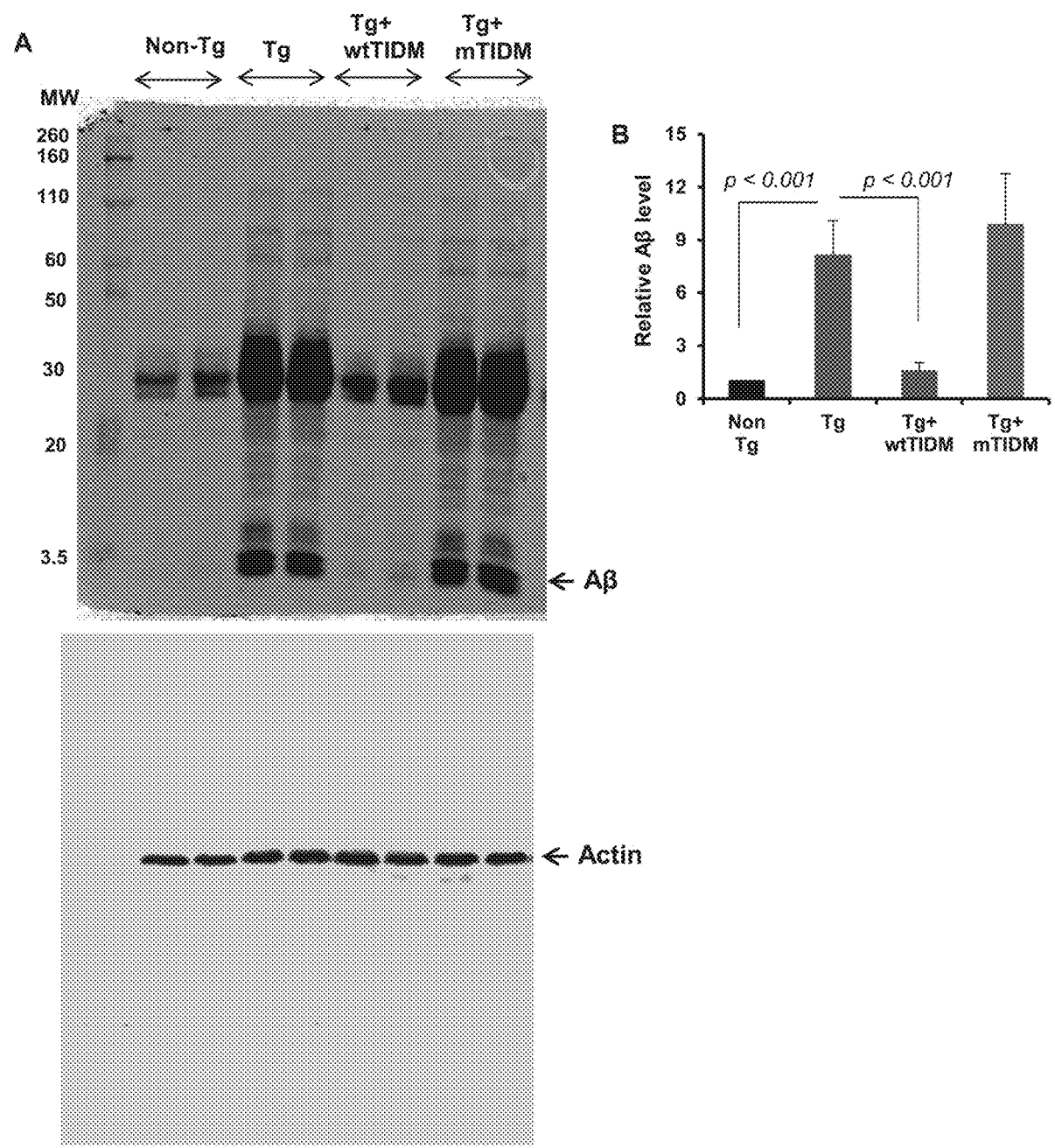
FIG. 20(A-B). Intranasal delivery of wtTIDM, but not mTIDM, peptide lowers the burden of amyloid plaques in the hippocampus of Tg mice. A) Tg mice (6-month old) were treated with wtTIDM and mTIDM peptides (0.1 mg/kg body wt/2d) via intranasal route. After 30d of treatment, hippocampal extracts of all groups of mice (n=4 per group) were analyzed for protein levels of Aβ by Western blot using 82E1 mAb. Actin was run as loading control. B) Bands were scanned and values (Aβ/Actin) presented as relative to non-Tg control. Results were analyzed by two-sample t-tests.
Figure 21:
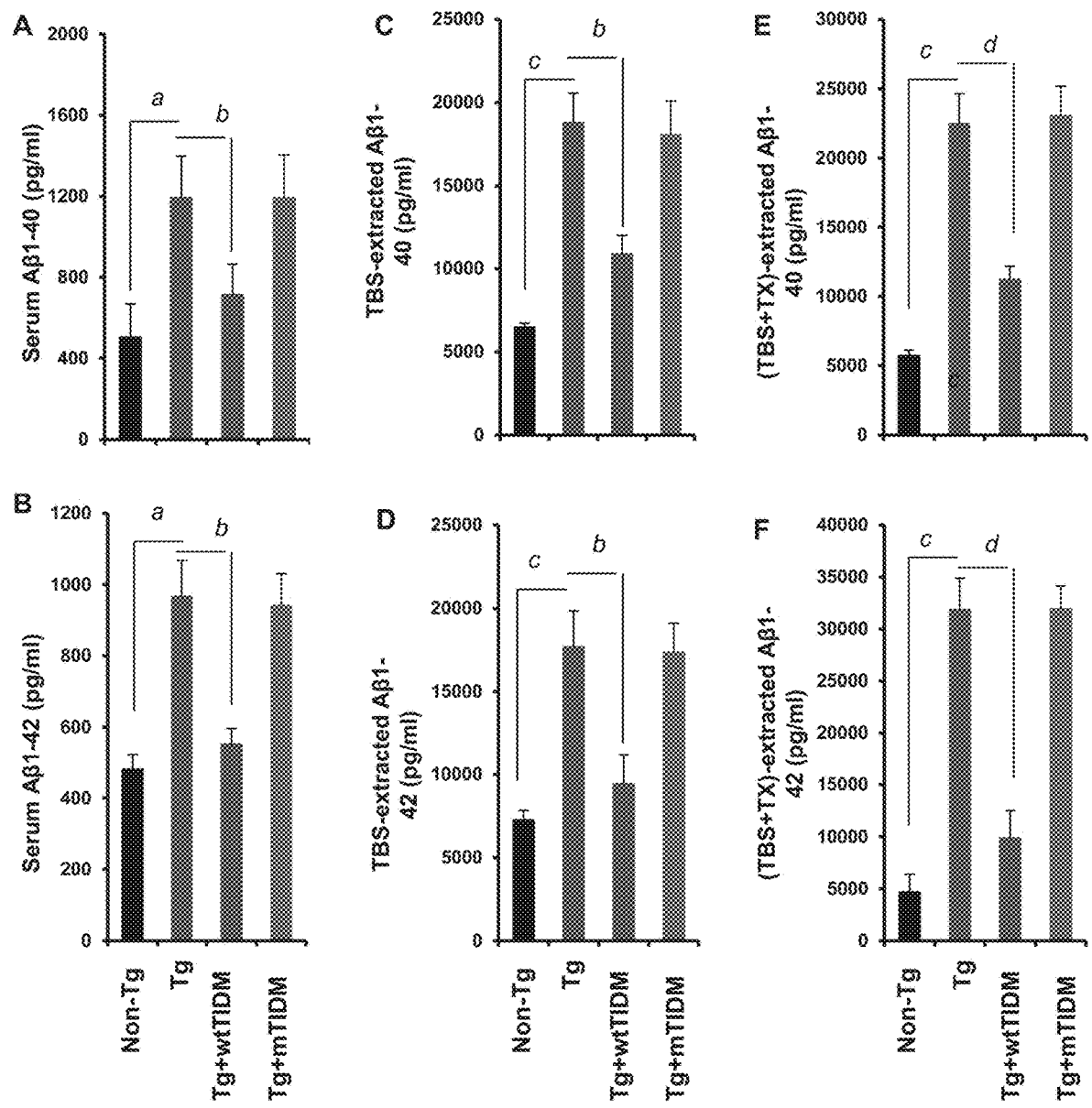
FIG. 21(A-F). Intranasal delivery of wtTIDM, but not mTIDM, peptide reduces the levels of Aβ1-40 and Aβ1-42 in serum and hippocampus of Tg mice. Tg mice (6-month old) were treated with wtTIDM and mTIDM peptides (0.1 mg/kg body wt/2d) via intranasal route. After 30d of treatment, ELISA quantification of Aβ1-40 (A, C & E) and Aβ1-42 (B, D & F) was performed in serum (A & B) and TBS (C & D) and (TBS+Triton X-100) (E & F) extracted hippocampal tissues. Six mice (n=6 per group) were used in two independent experiments. $ap<0.01$ & $cp<0.001$ versus non-Tg; $bp<0.01$ & $dp<0.001$ versus Tg by two-sample t-tests.

Amyloid plaque is an important feature of AD pathology, which is modeled in 5×FAD Tg mice (26, 27). Therefore, next, the inventor examined if wtTIDM treatment was capable of reducing the load of amyloid plaques from the hippocampus of Tg mice. Immunostaining of hippocampal sections with 82E1 mAb (FIG. 5M-O) as well as Western blot analysis of hippocampal tissues with 6E10 mAb (FIG. 5P-Q) and 82E1 mAb (FIG. 20A-B) showed markedly higher level of A3 peptides in the hippocampus of Tg mice as compared to non-Tg mice. Similarly, ELISA of serum (FIG. 21A-B), TBS-extracted hippocampal fractions (FIG. 21C-D) and (TBS+Triton X-100)-extracted hippocampal fractions (FIG. 21E-F) also demonstrated marked increase in Aβ1-40 and Aβ1-42 in Tg mice as compared to non-Tg mice. However, a significant decrease in A3 was seen with wtTIDM, but not mTIDM, treatment (FIG. 20A-B, FIG. 21A-F & FIG. 5M-Q). These results suggest that intranasal administration of wtTIDM is capable of reducing Aβ burden in the hippocampus of 5×FAD mice.

Figure 22:
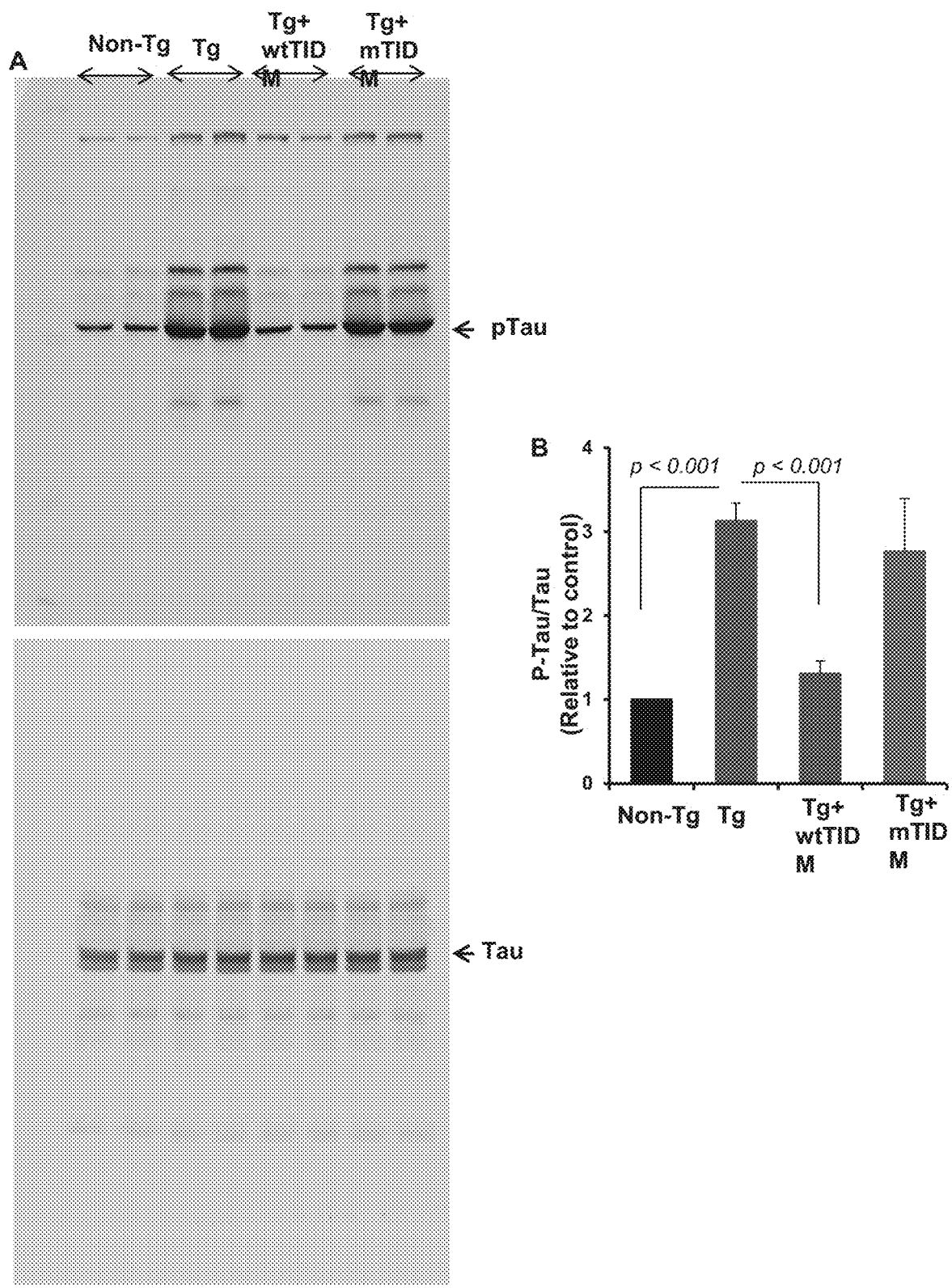
FIG. 22(A-B). Intranasal delivery of wtTIDM, but not mTIDM, peptide decreases the phosphorylation of tau in the hippocampus of Tg mice. A) Tg mice (6-month old) were treated with wtTIDM and mTIDM peptides (0.1 mg/kg body wt/2d) via intranasal route. After 30d of treatment, hippocampal extracts of all groups of mice (n=4 per group) were analyzed for phospho-tau and total tau by Western blot. B) Bands were scanned and values (P-Tau/Tau) presented as relative to non-Tg control. Results were analyzed by two-sample t-tests.

Hyperphosphorylation of tau is another prominent feature of AD pathology (28, 29). It has been shown that hyperphosphorylation at Ser396 of tau occurs in the hippocampus of 5×FAD mice at a much earlier stage than the appearance of learning and memory impairment (30). Therefore, the inventor examined the effect of TIDM peptide treatment on the status of tau phosphorylation in vivo in the hippocampus of Tg mice. Immunoblot analysis indicates a marked increase in phospho-tau in hippocampal extracts of Tg mice as compared to non-Tg mice (FIG. 22A-B). However, treatment of Tg mice with wtTIDM, but not mTIDM, peptide led to the suppression of phospho-tau in the hippocampus without affecting the total level of tau protein (FIG. 22A-B), indicating that wtTIDM peptide treatment is adequate in decreasing tau phosphorylation in the hippocampus of Tg mice.

Example 28—Reduction in Neuronal Apoptosis and Protection of Memory and Learning in 5×FAD Tg Mice by Intranasal Administration of wtTIDM Peptide Since neuroinflammation may be associated with neuronal apoptosis, next, the inventor examined if wtTIDM peptide treatment was able to reduce neuronal apoptosis in the hippocampus of Tg mice. A number of TUNEL-positive bodies co-localized with NeuN in the hippocampus of Tg mice as compared to non-Tg mice (FIG. 6A-C). However, wtTIDM, but not mTIDM, peptide attenuated neuronal apoptosis in the hippocampus (FIG. 6A-C). This result was confirmed by detection of cleaved caspase 3. As expected, the level of cleaved caspase 3 increased in the hippocampus of Tg mice (FIG. 6D-E). However, treatment of Tg mice with wtTIDM, but not mTIDM, peptide reduced the elevated level of cleaved caspase 3 in the hippocampus (FIG. 6D-E), suggesting that wtTIDM peptide treatment is capable of decreasing neuronal apoptosis in vivo in the hippocampus of Tg mice. Accordingly, levels of plasticity-related molecules (PSD-95, NR2 A and GluR1) decreased in the hippocampus of Tg mice as compared to non-Tg mice (FIG. 6F-I). However, consistent to the suppression of neuronal apoptosis, treatment of Tg mice with wtTIDM, but not mTIDM, peptide led to significant restoration of PSD-95, NR2 A and GluR1 proteins in vivo in the hippocampus (FIG. 6F-I).

Figure 23:
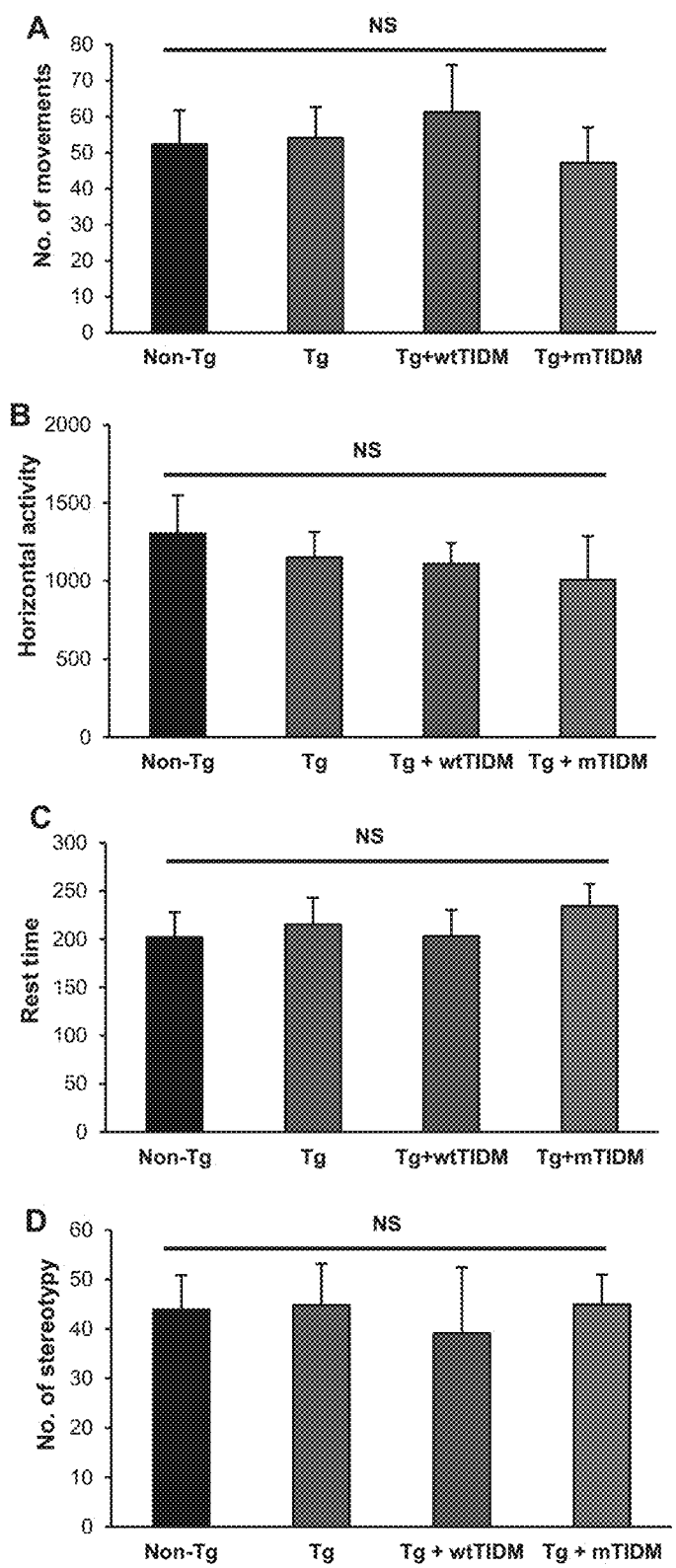
FIG. 23(A-D). Intranasal delivery of wtTIDM and mTIDM peptides does not modulate locomotor activities of Tg mice. Tg mice (6-month old) were treated with wtTIDM and mTIDM peptides (0.1 mg/kg body wt/2d) via intranasal route. After 30d of treatment, mice were tested for for general locomotor activities (A, number of movements; B, horizontal activity; C, rest time; D, number of stereotypy). Eight mice (n=8 in two independent experiments) were used in each group. NS, not significant.

The ultimate objective of neuroprotection in AD is to improve and/or protect memory. Major functions of the hippocampus are to generate and organize long-term memory and spatial learning. Therefore, the inventor examined if wtTIDM peptide protected memory and learning in Tg mice. As expected, Tg mice took much longer time to find the food reward hole and exhibited a greater latency [p<0.001 (=0.0000213)] with higher errors [p<0.001 (=0.0000251)] in the Barnes maze as compared to non-Tg mice. However, wtTIDM treatment significantly improved the memory functions of Tg mice as shown by latency [F3,28=93.153, p<0.001 (=0.0000112)] (FIG. 6J) and number of errors [F3,28=36.339, p<001 (=0.0000863)] (FIG. 6K). Memory functions of wtTIDM peptide-treated mice were also better in locating the reward hole with less latency [p<0.001 (=0.0000600)] and fewer errors [p<0.001 (=0.0000579)] when compared to mTIDM treated mice. Similarly, on T maze, untreated Tg mice also exhibited fewer number of positive turns [p<0.001 (=0.0000440)] and higher number of negative turns [p<0.001 (=0.000223)] than age-matched non-Tg mice (FIG. 6L-M). However, wtTIDM treatment displayed significant effect on successful positive turns [F3,28=31.475, p<0.001 (=0.0000411] (FIG. 6L) and also lesser number of errors [F3,28=26.653, p<0.001 (=0.0000235] (FIG. 6M) by Tg mice. Again, wtTIDM-treated mice exhibited a greater number of positive turns [p<0.001 (=0.0000954)] and less negative turns [p<0.001 (=0.000123)] as compared to mTIDM-treated Tg mice (FIG. 6L-M). The inventor also monitored short-term memory of Tg mice by Novel Object Recognition (NOR) test. Tg mice exhibited significant deficits [p<0.001 (=0.0000149)] in NOR test evidenced by discrimination index (FIG. 6N) compared to age-matched non-Tg mice. However, wtTIDM peptide-treated mice showed significant improvement (p<0.001) in short-term memory as compared to either untreated Tg or mTIDM-treated Tg mice (FIG. 6N). On the other hand, gross motor activities of Tg and non-Tg mice were almost similar (FIG. 23). Furthermore, either wtTIDM or mTIDM peptide did not modulate gross motor activities in Tg mice as evident from number of movements, horizontal activity, rest time, and stereotypy (FIG. 23A-D), suggesting that improvement of memory by wtTIDM peptide treatment is not due to any alteration in gross motor activities.

Figure 24:
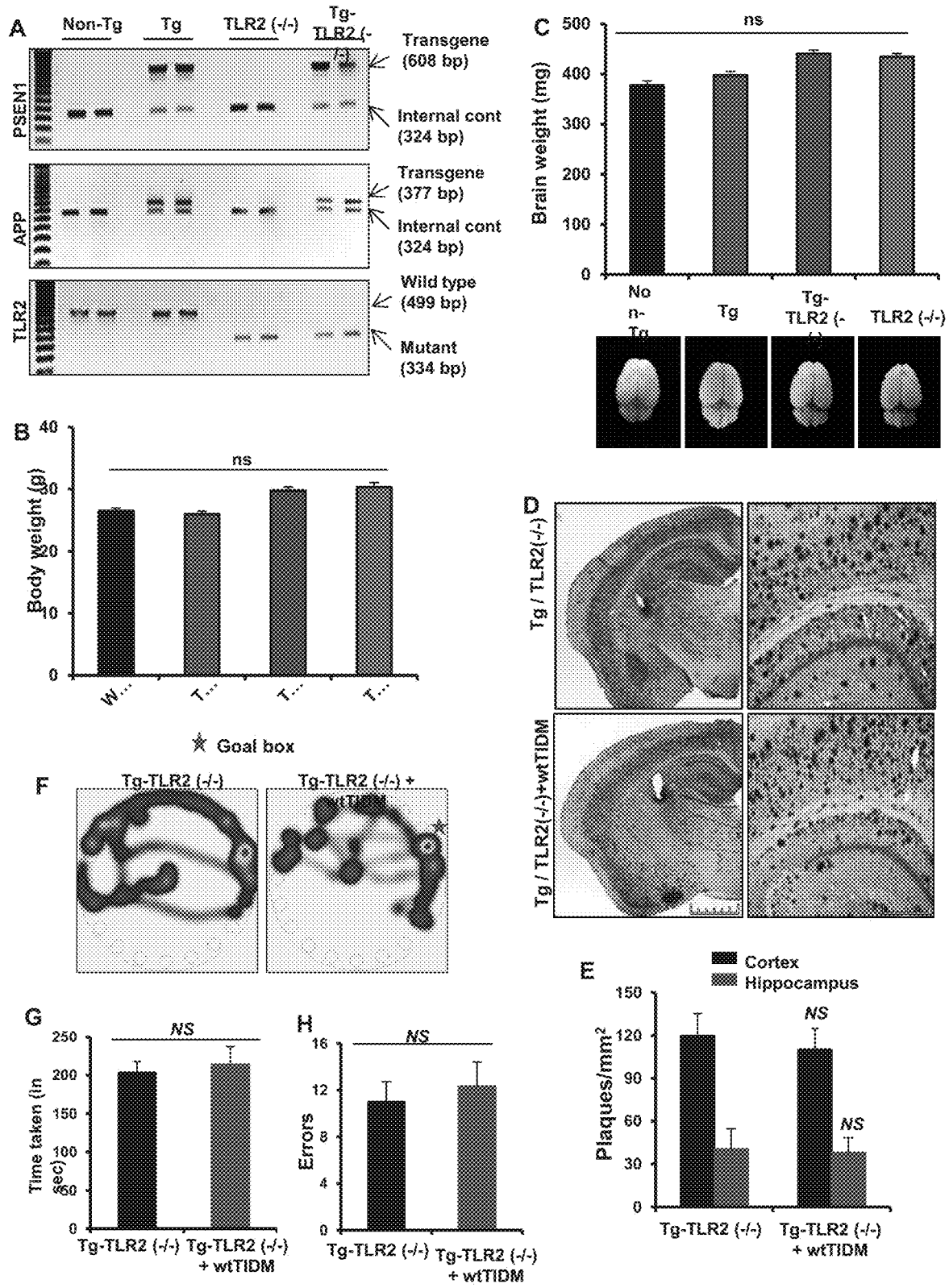
FIG. 24(A-H). Intranasal delivery of wtTIDM peptide does not reduce plaques and improve memory in FAD5× Tg mice lacking Tlr2 (Tg-Tlr2−/−). A) Tlr2−/− mice were bred with Tg (5×FAD mice) and representative PCR of Tlr2, App695 and Psen1 transgene DNA expression is shown for 6-month old non-Tg, Tg (5×FAD), Tg-Tlr2−/− (F7), and Tlr2−/− mice. Average body weight (B) and wet brain weight (C) of non-Tg, Tg, Tg-Tlr2−/−, and Tlr2−/− mice. For wet brain weight, the olfactory lobes and brainstem were removed. Tg-Tlr2−/− mice (6-month old) were treated with wtTIDM peptide (0.1 mg/kg body wt/2d) via intranasal route. After 30d of treatment, hippocampal sections were immunolabeled with 6E10 mAb (D). Amyloid plaques were counted in two sections (two images per slide) of each of four different mice per group (E). Mice were tested for Barnes maze (F, track plot; G, latency; H, number of errors made). Four mice (n=4) were used in each group. NS, not significant by two-sample t-tests.

Example 29—the wtTIDM Peptide Requires TLR2 to Reduce Plaques and Improve Memory in 5×FAD Tg Mice To confirm that wtTIDM peptide in fact requires TLR2 to exhibit its function in vivo, the inventor crossed Tlr2−/− mice with Tg mice to create 5×FAD mice null for Tlr2 (Tg-Tlr2−/−). The Tlr2 knockdown did not alter insertion or expression of the 5×FAD transgenes, and vice versa (FIG. S24A). Six month old WT, Tlr2−/−, Tg, and Tg-Tlr2−/− mice did not differ significantly with respect to gross body weight or wet brain weight (FIG. 24B-C). The inventor also did not find any overt phenotypic differences, including diet, fecal boli, social interaction, and agitation across genotypes at this age. Although wtTIDM peptide reduced plaque load and improved spatial learning and memory in Tg mice (FIGS. 5-6), it remained unable to do so in Tg-Tlr2−/− mice (FIG. 24D-G), indicating that wtTIDM peptide is ineffective in the absence of Tlr2.

Figure 25:
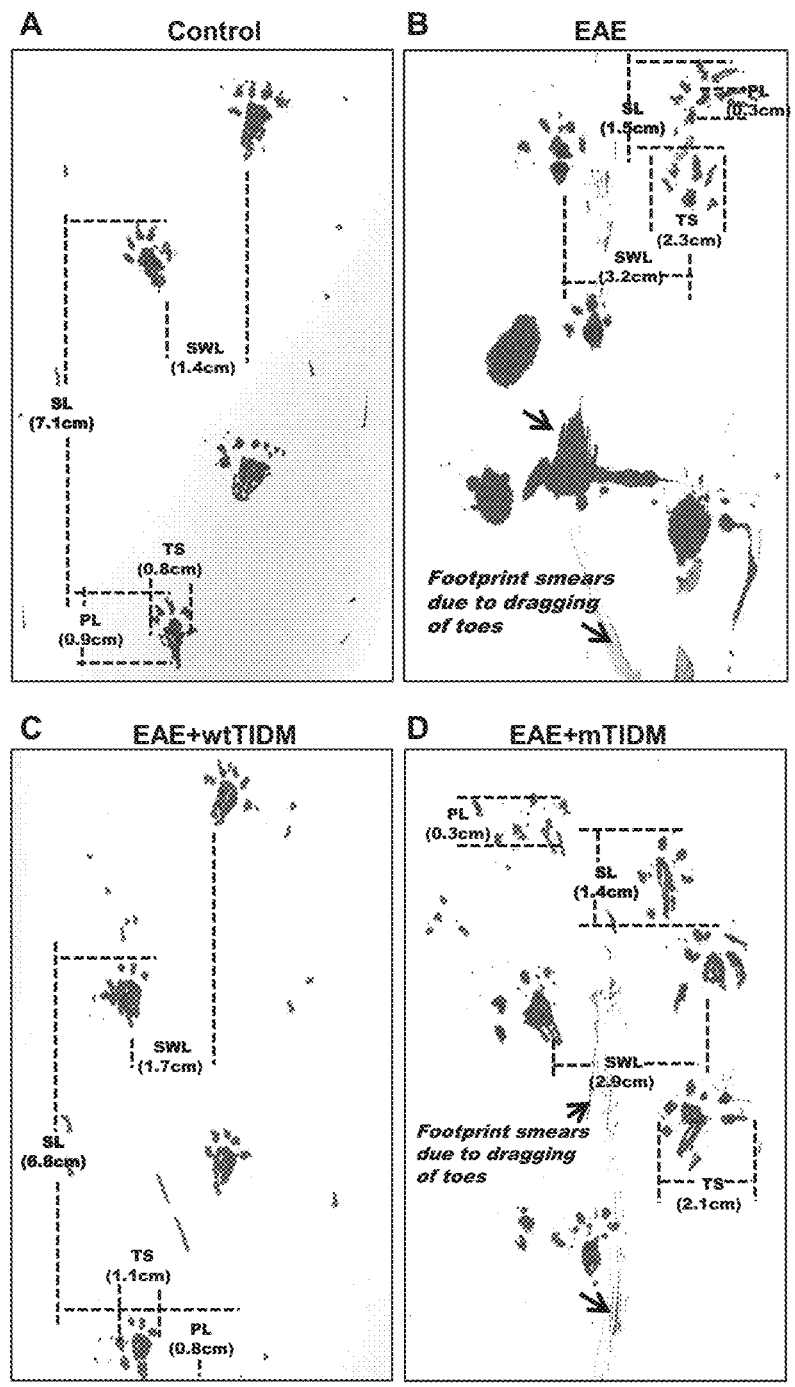
FIG. 25(A-D). Footprint analysis of EAE mice after treatment with wtTIDM and mTIDM peptides. On the walking track, we applied white paper strips and obtained the footprints of mice of different groups (A, control; B, EAE; C, EAE+wtTIDM; D, EAE+mTIDM) on paper using black ink. A total of 30-40 steps for each group were determined. Four different footprint measurements, viz., stride length (SL), print length (PL), sway length (SWL), and toe spread (TS) were calculated in centimeters from the recorded prints of mice. While SL refers the distance between the front edge of two consecutive prints of the same paw, SWL refers the distance between the paws perpendicular to the distance of travel and PL indicates the measurement of length of print area. On the other hand, TS refers the distance between the first and fifth digits of paw print. Six mice (n=6 per group) were used in two independent experiments.
Figure 26:
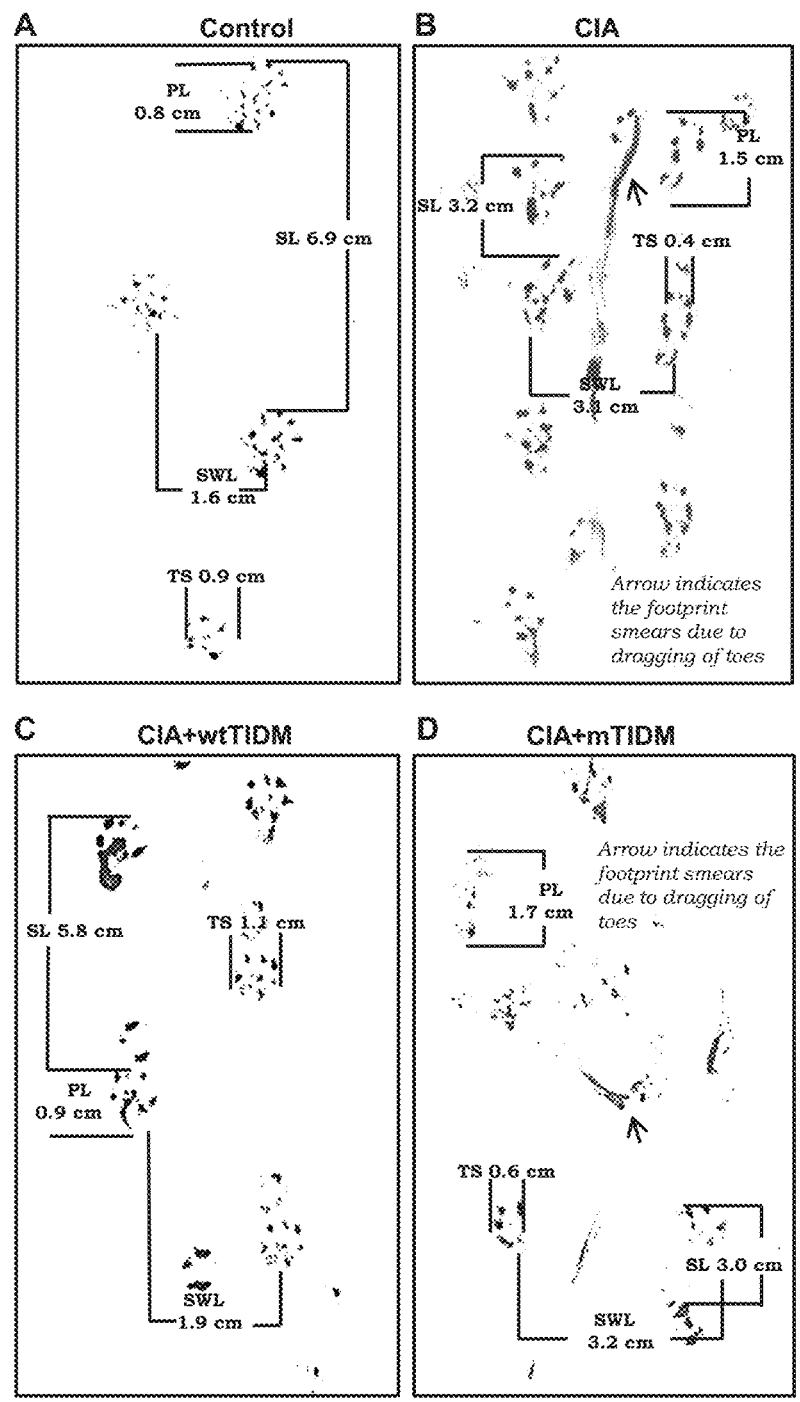
FIG. 26(A-D). Footprint analysis of mice with CIA after treatment with wtTIDM and mTIDM peptides. On the walking track, we applied white paper strips and obtained the footprints of mice of different groups (A, control; B, CIA; C, CIA+wtTIDM; D, CIA+mTIDM) on paper using black ink. A total of 30-40 steps for each group were determined. Four different footprint measurements (SL, PL, SWL, and TS) were calculated in centimeters from the recorded prints of mice. Six mice (n=6 per group) were used in two independent experiments.

Example 30—the wtTIDM, but not mTIDM, Peptide Suppresses the Disease Process of Experimental Allergic Encephalomyelitis (EAE) and Collagen-Induced Arthritis (CIA) in Mice Being an important member of the innate immune pathways, Myd88-dependent TLR2 signaling plays an important role in the pathogenesis of a wide variety of infectious and autoimmune disorders (31, 32). Therefore, the inventor examined whether the function of wtTIDM peptide was limited to only 5×FAD mice or other disease models as well. EAE is the widely-used animal model of multiple sclerosis (MS) and chronic form of EAE is modeled in male C57/BL6 mice upon immunization with MOG35-55. Similar to its effect in 5×FAD mice, intranasal treatment of EAE mice with wtTIDM peptide strongly inhibited the clinical symptoms of EAE (FIG. 7A). While comparing the means between groups with Dunnett's multiple comparison analyses, the inventor found that there was significant difference of means between EAE and EAE+wtTIDM (adjusted p<0.001). On the other hand, mTIDM peptide had no effect (FIG. 7A), suggesting the specificity of the effect. As expected, induction of EAE reduced locomotor activities in mice that are evident by heat-map analysis (FIG. 7B), distance traveled (FIG. 7C), rearing (FIG. 7D), velocity (FIG. 7E), and acceleration (FIG. 7F). Footprint analysis (FIG. 25) also indicated decrease in stride length (FIG. 7G) and point length (FIG. 7H) and increase in sway length (FIG. 7I) and toe spread (FIG. 7J) in EAE mice as compared to normal mice. The inventor also found dragging of toes frequently in EAE mice (FIG. 25). However, intranasal treatment by wtTIDM, but not mTIDM, peptide improved locomotor activities and normalized footprints in EAE mice (FIG. 7A-K & FIG. 25). CIA is a widely-used animal model of rheumatoid arthritis. Similar to EAE mice, wtTIDM, but not mTIDM, peptide also decreased clinical symptoms of CIA in mice (FIG. 7L). While comparing the means between groups with Dunnett's multiple comparison analyses, the inventor found that there was significant difference of means between CIA and CIA+wtTIDM. The wtTIDM peptide also enhanced locomotor activities (FIG. 7N-R), and improved footprint behavior (FIG. 7S-V & FIG. 26).

Example 31—Intranasal Administration of TLR2-Interacting Domain of MyD88 (TIDM) Peptide Reduces α-Synucleinopathy: Implications for Parkinson's Disease, Multiple System Atrophy and Dementia with Lewy Bodies The pathological findings in Parkinson's disease (PD) include a selective loss of dopaminergic neurons in the SNpc and the presence of intracytoplasmic aggregation of α-syn protein in the form of Lewy bodies in surviving neurons. In addition to PD, accumulation of α-syn is also an important pathological hallmark of dementia with Lewy bodies (DLB) and multiple system atrophy (MSA). Therefore, decreasing Lewy body pathology has therapeutic importance in PD, DLB and MSA. Microglial activation plays an important role in the pathogenesis of Lewy body diseases and it has been shown that fibrillar α-syn requires TLR2 for the activation of microglia. Recently, the inventor has demonstrated that peptide corresponding to the TLR2-interacting domain of MyD88 (TIDM) selectively inhibits the activation of TLR2. This study underlines the importance of TIDM peptide in reducing α-synucleinopathy. Intranasal administration of wild type (wt) TIDM peptide reduced microglial expression of inducible nitric oxide synthase (iNOS) in the nigra of A53T transgenic mice (FIG. 28A-B). Although wtTIDM peptide inhibited the expression of iNOS, we observed increase arginase-1 in the nigra of A53T mice after wtTIDM treatment (FIG. 29A-B), suggesting switching microglial activation from M1 to M2 mode by wtTIDM peptide. Daily intranasal treatment of A53T mice with wtTIDM peptide also led to reduction in oligomeric and monomeric α-syn (FIG. 30A-C) and suppression of α-syn inclusion bodies within tyrosine hydroxylase-positive dopaminergic neurons (FIG. 31A-D). We also observed decrease in microglial α-syn in the nigra of A53T mice after wtTIDM peptide treatment (FIG. 32A-B). Finally, wtTIDM peptide treatment improved locomotor activities of A53T mice (FIG. 33A-E). These results were specific as mutated TIDM peptide did not exhibit any such protective effect in A53T mice. Therefore, intranasal treatment of wtTIDM peptide may be beneficial for PD, MSA and DLB.

REFERENCES

1. Tanzi R E, and Bertram L. Twenty years of the Alzheimer's disease amyloid hypothesis: a genetic perspective. Cell. 2005; 120(4):545-55.
2. Hardy J, Duff K, Hardy K G, Perez-Tur J, and Hutton M. Genetic dissection of Alzheimer's disease and related dementias: amyloid and its relationship to tau. Nat Neurosci. 1998; 1(5):355-8.
3. Raichlen D A, and Alexander G E. Exercise, APOE genotype, and the evolution of the human lifespan. Trends Neurosci. 2014; 37(5):247-55.
4. Rapoport M, Dawson H N, Binder L I, Vitek M P, and Ferreira A. Tau is essential to beta-amyloid-induced neurotoxicity. Proc Natl Acad Sci USA. 2002; 99(9):6364-9.
5. Roberson E D, Scearce-Levie K, Palop J J, Yan F, Cheng I H, Wu T, et al. Reducing endogenous tau ameliorates amyloid beta-induced deficits in an Alzheimer's disease mouse model. Science. 2007; 316(5825):750-4.
6. Benilova I, Karran E, and De Strooper B. The toxic Abeta oligomer and Alzheimer's disease: an emperor in need of clothes. Nat Neurosci. 2012; 15(3):349-57.
7. Heppner F L, Ransohoff R M, and Becher B. Immune attack: the role of inflammation in Alzheimer disease. Nat Rev Neurosci. 2015; 16(6):358-72.
8. Xu H, Gelyana E, Rajsombath M, Yang T, Li S, and Selkoe D. Environmental Enrichment Potently Prevents Microglia-Mediated Neuroinflammation by Human Amyloid beta-Protein Oligomers. J Neurosci. 2016; 36(35):9041-56.
9. Nathan C, Calingasan N, Nezezon J, Ding A, Lucia M S, La Perle K, et al. Protection from Alzheimer's-like disease in the mouse by genetic ablation of inducible nitric oxide synthase. J Exp Med. 2005; 202(9):1163-9.
10. Jana A, and Pahan K. Fibrillar amyloid-beta-activated human astroglia kill primary human neurons via neutral sphingomyelinase: implications for Alzheimer's disease. J Neurosci. 2010; 30(38):12676-89.
11. Meda L, Cassatella M A, Szendrei G I, Otvos L, Jr., Baron P, Villalba M, et al. Activation of microglial cells by beta-amyloid protein and interferon-gamma. Nature. 1995; 374(6523):647-50.
12. Mrak R E, Sheng J G, and Griffin W S. Correlation of astrocytic S100 beta expression with dystrophic neurites in amyloid plaques of Alzheimer's disease. J Neuropathol Exp Neurol. 1996; 55(3):273-9.
13. Vlad S C, Miller D R, Kowall N W, and Felson D T. Protective effects of NSAIDs on the development of Alzheimer disease. Neurology. 2008; 70(19):1672-7.
14. Beutler B. Inferences, questions and possibilities in Toll-like receptor signalling. Nature. 2004; 430(6996):257-63.
15. O'Neill L A, Golenbock D, and Bowie A G. The history of Toll-like receptors—redefining innate immunity. Nat Rev Immunol. 2013; 13(6):453-60.
16. Rivest S. Regulation of innate immune responses in the brain. Nat Rev Immunol. 2009; 9(6):429-39.
17. Jana M, Palencia C A, and Pahan K. Fibrillar amyloid-beta peptides activate microglia via TLR2: implications for Alzheimer's disease. J Immunol. 2008; 181(10):7254-62.
18. Liu S, Liu Y, Hao W, Wolf L, Kiliaan A J, Penke B, et al. TLR2 is a primary receptor for Alzheimer's amyloid beta peptide to trigger neuroinflammatory activation. J Immunol. 2012; 188(3):1098-107.
19. Reed-Geaghan E G, Reed Q W, Cramer P E, and Landreth G E. Deletion of CD14 attenuates Alzheimer's disease pathology by influencing the brain's inflammatory milieu. J Neurosci. 2010; 30(46):15369-73.
20. Gay N J, Symmons M F, Gangloff M, and Bryant C E. Assembly and localization of Toll-like receptor signalling complexes. Nat Rev Immunol. 2014; 14(8):546-58.

21. Gonzalez-Scarano F, and Baltuch G. Microglia as mediators of inflammatory and degenerative diseases. Annu Rev Neurosci. 1999; 22:219-40.
22. Rangasamy S B, Corbett G T, Roy A, Modi K K, Bennett D A, Mufson E J, et al. Intranasal Delivery of NEMO-Binding Domain Peptide Prevents Memory Loss in a Mouse Model of Alzheimer's Disease. J Alzheimers Dis. 2015; 47(2):385-402.
23. Ghosh A, Roy A, Liu X, Kordower J H, Mufson E J, Hartley D M, et al. Selective inhibition of NF-kappaB activation prevents dopaminergic neuronal loss in a mouse model of Parkinson's disease. Proc Natl Acad Sci USA. 2007; 104(47):18754-9.
24. Mondal S, Roy A, Jana A, Ghosh S, Kordower J H, and Pahan K. Testing N F-kappaB-based therapy in hemiparkinsonian monkeys. J Neuroimmune Pharmacol. 2012; 7(3):544-56.
25. Saha R N, and Pahan K. Regulation of inducible nitric oxide synthase gene in glial cells. Antioxid Redox Signal. 2006; 8 (5-6):929-47.
26. Corbett G T, Gonzalez F J, and Pahan K. Activation of peroxisome proliferator-activated receptor alpha stimulates ADAM10-mediated proteolysis of APP. Proc Natl Acad Sci USA. 2015; 112(27):8445-50.
27. Oakley H, Cole S L, Logan S, Maus E, Shao P, Craft J, et al. Intraneuronal beta-amyloid aggregates, neurodegeneration, and neuron loss in transgenic mice with five familial Alzheimer's disease mutations: potential factors in amyloid plaque formation. J Neurosci. 2006; 26(40):10129-40.
28. Mondragon-Rodriguez S, Perry G, Luna-Munoz J, Acevedo-Aquino M C, and Williams S. Phosphorylation of tau protein at sites Ser (396-404) is one of the earliest events in Alzheimer's disease and Down syndrome. Neuropathol Appl Neurobiol. 2014; 40(2):121-35.
29. Regan P, Piers T, Yi J H, Kim D H, Huh S, Park S J, et al. Tau phosphorylation at serine 396 residue is required for hippocampal LTD. J Neurosci. 2015; 35(12):4804-12.
30. Kanno T, Tsuchiya A, and Nishizaki T. Hyperphosphorylation of Tau at Ser396 occurs in the much earlier stage than appearance of learning and memory disorders in 5xFAD mice. Behav Brain Res. 2014; 274:302-6.
31. Liu Y, Yin H, Zhao M, and Lu Q. TLR2 and TLR4 in autoimmune diseases: a comprehensive review. Clin Rev Allergy Immunol. 2014; 47(2):136-47.
32. Oliveira-Nascimento L, Massari P, and Wetzler L M. The Role of TLR2 in Infection and Immunity. Front Immunol. 2012; 3:79.
33. Reed-Geaghan E G, Savage J C, Hise A G, and Landreth G E. CD14 and toll-like receptors 2 and 4 are required for fibrillar A {beta}-stimulated microglial activation. J Neurosci. 2009; 29(38):11982-92.
34. Yu J T, Mou S M, Wang L Z, Mao C X, and Tan L. Toll-like receptor 2-196 to −174 del polymorphism influences the susceptibility of Han Chinese people to Alzheimer's disease. J Neuroinflammation. 2011; 8:136.
35. Zhang W, Wang L Z, Yu J T, Chi Z F, and Tan L. Increased expressions of TLR2 and TLR4 on peripheral blood mononuclear cells from patients with Alzheimer's disease. J Neurol Sci. 2012; 315 (1-2):67-71.
36. Balayssac S, Burlina F, Convert O, Bolbach G, Chassaing G, and Lequin O. Comparison of penetratin and other homeodomain-derived cell-penetrating peptides: interaction in a membrane-mimicking environment and cellular uptake efficiency. Biochemistry. 2006; 45(5):1408-20.
37. Borrelli A, Tornesello A L, Tornesello M L, and Buonaguro F M. Cell Penetrating Peptides as Molecular Carriers for Anti-Cancer Agents. Molecules. 2018; 23 (2).
38. Bera S, Kar R K, Mondal S, Pahan K, and Bhunia A. Structural Elucidation of the Cell-Penetrating Penetratin Peptide in Model Membranes at the Atomic Level: Probing Hydrophobic Interactions in the Blood-Brain Barrier. Biochemistry. 2016; 55(35):4982-96.
39. Richard K L, Filali M, Prefontaine P, and Rivest S. Toll-like receptor 2 acts as a natural innate immune receptor to clear amyloid beta 1-42 and delay the cognitive decline in a mouse model of Alzheimer's disease. J Neurosci. 2008; 28(22):5784-93.
40. Friis L M, Keelan M, and Taylor D E. *Campylobacter jejuni* drives MyD88-independent interleukin-6 secretion via Toll-like receptor 2. Infect Immun. 2009; 77(4):1553-60.
41. Gao Q, Qi L, Wu T, and Wang J. *Clostridium butyricum* activates TLR2-mediated MyD88-independent signaling pathway in HT-29 cells. Mol Cell Biochem. 2012; 361 (1-2):31-7.
42. Buggia-Prevot V, Sevalle J, Rossner S, and Checler F. NFkappaB-dependent control of BACE1 promoter transactivation by Abeta42. J Biol Chem. 2008; 283(15):10037-47.
43. Atri A. Effective pharmacological management of Alzheimer's disease. Am J Manag Care. 2011; 17 Suppl 13:S346-55.
44. Bennett D A, Schneider J A, Arvanitakis Z, Kelly J F, Aggarwal N T, Shah R C, et al. Neuropathology of older persons without cognitive impairment from two community-based studies. Neurology. 2006; 66(12):1837-44.
45. Bennett D A, Schneider J A, Arvanitakis Z, and Wilson R S. Overview and findings from the religious orders study. Curr Alzheimer Res. 2012; 9(6):628-45.
46. Bennett D A, Schneider J A, Bienias J L, Evans D A, and Wilson R S. Mild cognitive impairment is related to Alzheimer disease pathology and cerebral infarctions. Neurology. 2005; 64(5):834-41.
47. Wilson R S, Beckett L A, Barnes L L, Schneider J A, Bach J, Evans D A, et al. Individual differences in rates of change in cognitive abilities of older persons. Psychol Aging. 2002; 17(2):179-93.
48. Braak H, and Braak E. Neuropathological stageing of Alzheimer-related changes. Acta Neuropathol. 1991; 82(4):239-59.
49. Jana A, Modi K K, Roy A, Anderson J A, van Breemen R B, and Pahan K. Up-regulation of neurotrophic factors by cinnamon and its metabolite sodium benzoate: therapeutic implications for neurodegenerative disorders. J Neuroimmune Pharmacol. 2013; 8(3):739-55.
50. Corbett G T, Roy A, and Pahan K. Gemfibrozil, a lipid-lowering drug, upregulates IL-1 receptor antagonist in mouse cortical neurons: implications for neuronal self-defense. J Immunol. 189(2):1002-13.
51. Khasnavis S, and Pahan K. Sodium benzoate, a metabolite of cinnamon and a food additive, upregulates neuroprotective Parkinson disease protein DJ-1 in astrocytes and neurons. J Neuroimmune Pharmacol. 2012; 7(2):424-35.
52. Roy A, Jana M, Kundu M, Corbett G T, Rangaswamy S B, Mishra R K, et al. HMG-CoA Reductase Inhibitors Bind to PPARalpha to Upregulate Neurotrophin Expression in the Brain and Improve Memory in Mice. Cell Metab. 2015; 22(2):253-65.

53. Roy A, Kundu M, Jana M, Mishra R K, Yung Y, Luan C H, et al. Identification and characterization of PPARalpha ligands in the hippocampus. Nat Chem Biol. 2016; 12(12):1075-83.
54. Mondal S, Martinson J A, Ghosh S, Watson R, and Pahan K. Protection of Tregs, suppression of Th1 and Th17 cells, and amelioration of experimental allergic encephalomyelitis by a physically-modified saline. PLoS ONE. 2012; 7(12):000.
55. Mondal S, and Pahan K. Cinnamon ameliorates experimental allergic encephalomyelitis in mice via regulatory T cells: implications for multiple sclerosis therapy. PLoS One. 2015; 10 (1):e0116566.
56. Pike C J, Burdick D, Walencewicz A J, Glabe C G, and Cotman C W. Neurodegeneration induced by beta-amyloid peptides in vitro: the role of peptide assembly state. J Neurosci. 1993; 13(4):1676-87.
57. Roy A, Jana M, Corbett G T, Ramaswamy S, Kordower J H, Gonzalez F J, et al. Regulation of cyclic AMP response element binding and hippocampal plasticity-related genes by peroxisome proliferator-activated receptor alpha. Cell Rep. 2013; 4(4):724-
58. Mansuy I M, Mayford M, Jacob B, Kandel E R, and Bach M E. Restricted and regulated overexpression reveals calcineurin as a key component in the transition from short-term to long-term memory. Cell. 1998; 92(1):39-49.
59. Khasnavis S, Roy A, Ghosh S, Watson R, and Pahan K. Protection of dopaminergic neurons in a mouse model of Parkinson's disease by a physically-modified saline containing charge-stabilized nanobubbles. J Neuroimmune Pharmacol. 2013; 9(2):218-32.

TABLE S1

Table S1: Clinical and pathological characteristics of human samples

| Number of samples | NCI (n = 12) | MCI (n = 11) | AD (n = 10) |
|---|---|---|---|
| Age (years) at death | 82.18 ± 5.13 | 84.87 ± 6.23 | 88.73 ± 5.89 |
| Number of males | 4 | 7 | 5 |
| Number of females | 8 | 4 | 5 |
| Number of ApoE e4 allele | 4 | 2 | 5 |
| MMSE | 27.25 ± 2.77 | 25.95 ± 1.92 | 13.30 ± 5.27 |
| GCS | 0.44 ± 0.32 | 0.09 ± 0.27 | −1.13 ± 0.39 |
| PMI (hours) | 7.45 ± 6.36 | 5.15 ± 3.12 | 6.57 ± 3.33 |
| Distribution of Braak Scores | | | |
| No AD | 0 | 0 | 0 |
| I/II | 2 | 2 | 1 |
| III/IV | 10 | 7 | 5 |
| V/I | 0 | 2 | 4 |
| NIA Reagan | | | |
| No AD | 0 | 0 | 0 |
| Low | 5 | 3 | 1 |
| Intermediate | 7 | 7 | 6 |
| High | 0 | 1 | 3 |
| CERAD | | | |
| No AD | 5 | 3 | 0 |
| Possible | 0 | 0 | 0 |
| Probable | 5 | 6 | 6 |
| Definite | 2 | 2 | 4 |

NCI, No cognitive impairment;
MCI, mild cognitive impairment;
AD, Alzheimer's disease;
ApoE, apolipoprotein E;
MMSE, Mini-Mental State Examination;
GCS, global cognitive z score;
PMI, post-mortem interval;
NIA, National Institute on Aging;
CERAD, Consortium to Establish a Registry for Alzheimer's Disease

TABLE S2

Table S2: Correlations of TLR2, TLR4 and MyD88 with Cognitive Test Scores

| | NCI | MCI | AD | $p^a$ | Pairwise | MMSE | GCS | Braak |
|---|---|---|---|---|---|---|---|---|
| | | | | | | \multicolumn{3}{c}{$r^b$} | | |
| MyD88 | 6.38 ± 1.26 | 14.69 ± 4.41 | 45.66 ± 7.72 | <.001 | NCI, MCI < AD | −.538, p = .001 | −.475, p = .005 | .371, p = .033 |
| TLR2 | 24.75 ± 6.05 | 29.98 ± 11.44 | 69.37 ± 11.47 | .018 | NCI, MCI < AD | −.278, p = .117 | −.177, p = .326 | .463, p = .007 |
| TLR4 | 15.36 ± 3.82 | 14.61 ± 4.92 | 10.55 ± 1.61 | .620 | N/A | −.173, p = .336 | .047, p = .794 | −.012, p = .947 |

Pre-frontal cortext homogenates of NCI, MCI and AD were immunoblotted with antibodies against TLR2, TLR4 and MyD88. β-actin was used to normalize loading. Values represent mean ± SEM (range). Protein levels of TLR2, TLR4 and MyD88 were correlated with MMSE, GCS and Braak. AD, Alzheimer's disease; MCI, mild cognitive impairment; NCI, no cognitive impairment; MMSE, Mini-Mental State Examination; GCS, Global Cognitive z Score.
$^a$Kruskal-Wallis test corrected for multiple comparaisons; Spearman's Rank Order correlation (2-tailed), unadjusted

TABLE S3

Table S3. Antibodies, sources, applications, and dilutions used

| Antibody | Manufacturer | Catalog | Host | Application | Dilution/Amount |
|---|---|---|---|---|---|
| TLR2 | Millipore | 06-1119 | Rabbit | WB/IF | 1:1000/1:100 |
| TLR4 | Abcam | Ab13556 | Rabbit | WB/IF | 1:1000/1:150 |
| MyD88 | Millipore | AB16527 | Rabbit | WB | 1:1000 |
| MyD88 | Abcam | Ab2068 | Rabbit | IF | 1:150 |
| MyD88 | Santa Cruz | Sc11356 | Rabbit | IP | 2 μg/reaction |
| β-actin | Abcam | Ab6276 | Mouse | WB | 1:6000 |
| 6E10 | Covance | sig-39320 | Mouse | WB | 1:1000 |
| phosphorylated p65$^{S536}$ | Cell Signaling | 3031S | Rabbit | WB/IF | 1:1000 |
| 82E1 | IBL | 10323 | Mouse | IHC | 1:1000 |
| Iba-1 | Abcam | Ab5076 | Goat | IF | 1:500 |
| GFAP | Dako | Z0334 | Rabbit | WB/IF | 1:1000/1:2000 |
| NeuN | Minipore | NAB377 | Mouse | IF | 1:500 |

TABLE S3-continued

Table S3. Antibodies, sources, applications, and dilutions used

| Antibody | Manufacturer | Catalog | Host | Application | Dilution/Amount |
|---|---|---|---|---|---|
| iNOS | BD Bioscience | 610432 | Mouse | WB/IF | 1:200 |
| Cleaved caspase 3 | Santa Cruz | sc-7148 | Rabbit | WB | 1:100 |
| PSD95 | Abcam | Ab2723 | Mouse | WB | 1:1000 |
| NR2A | Cell Signaling | 4205S | Rabbit | WB | 1:250 |
| GluR1 | Cell Signaling | 13185S | Rabbit | WB | 1:250 |

WB, Western blot;
IP, immunoprecipitation;
IHC, immunohistochemistry;
IF, immunofluorescence

I claim:

1. A method for treating a disorder in a patient, the method comprising administering to the patient in need of such treatment a therapeutically effective amount of a composition comprising a peptide comprising a Toll-like Receptor 2 (TLR2)-interacting domain of myeloid differentiation primary response 88 (MyD88), wherein the TLR2-interating domain of MyD88 comprises the sequence PGAHQK (SEQ ID NO: 1), wherein the therapeutically effective amount is an amount that at least reduces TLR2-MyD88 signaling and wherein the disorder is a neurological disorder selected from the group consisting of Alzheimer's disease, Parkinson's disease, dementia with Lewy bodies, Huntington's disease and multiple system atrophy.

2. The method of claim 1, wherein the peptide comprising a TLR2-interacting domain of MyD88, further comprises Antennapedia homeodomain.

3. The method of claim 2, wherein the Antennapedia homeodomain is linked by the C-terminal of the Antennapedia homeodomain to the N-terminal of the sequence PGAHQK (SEQ ID NO: 1).

4. The method of claim 1, wherein the peptide comprising a TLR2-interacting domain of MyD88 is drqikwfqnrrmkwkkPGAHQK (SEQ ID NO: 2).

5. The method of claim 1, wherein the composition further comprises at least one pharmaceutically acceptable carrier.

6. The method of claim 1, wherein the composition is administered intranasally.

7. The method of claim 1, wherein the patient is a human patient.

\* \* \* \* \*

UNITED STATES PATENT AND TRADEMARK OFFICE
CERTIFICATE OF CORRECTION

PATENT NO. : 11,524,052 B2  
APPLICATION NO. : 16/966277  
DATED : December 13, 2022  
INVENTOR(S) : Kalipada Pahan Page 1 of 1

It is certified that error appears in the above-identified patent and that said Letters Patent is hereby corrected as shown below:

In the Claims

In Claim 4, Column 35, Line 3, replace --drqikwfqnrrmkwkkPGAHQK-- with --drqikiwfqnrrmkwkkPGAHQK--.

Signed and Sealed this  
Thirtieth Day of July, 2024

Katherine Kelly Vidal  
*Director of the United States Patent and Trademark Office*